US006384028B1

(12) United States Patent
Ohkubo et al.

(10) Patent No.: US 6,384,028 B1
(45) Date of Patent: *May 7, 2002

(54) N-ACYLPIPERIDINYLCARBONYLAMINO-CARBOXYLIC ACIDS AND THEIR USE AS GLYCOPROTEIN IIB/IIIA ANTAGONISTS AND FIBRINOGEN-BLOOD PLATELETS BINDING INHIBITORS

(75) Inventors: Mitsuru Ohkubo, Hyogo; Fumie Takahashi, Higashiosaka; Toshio Yamanaka, Osaka; Masayuki Kato, Kyoto, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,795

(22) PCT Filed: Mar. 14, 1996

(86) PCT No.: PCT/JP96/00643

§ 371 Date: Sep. 10, 1997

§ 102(e) Date: Sep. 10, 1997

(87) PCT Pub. No.: WO96/29309

PCT Pub. Date: Sep. 26, 1996

(30) Foreign Application Priority Data

Mar. 17, 1995 (GB) .............................. 9505437
Nov. 28, 1995 (GB) .............................. 9524266

(51) Int. Cl.[7] .................. C07D 211/36; C07D 217/26; A61K 31/445; A61P 7/02
(52) U.S. Cl. .................. 514/210.21; 514/307; 514/308; 514/316; 514/318; 514/326; 514/330; 546/140; 546/146; 546/187; 546/189; 546/192; 546/193; 546/194; 546/208

(58) Field of Search .................. 514/307, 308, 514/316, 318, 326, 330, 210.21; 546/140, 146, 187, 189, 192, 193, 194, 208

(56) References Cited

U.S. PATENT DOCUMENTS 5,273,982 A * 12/1993 Alig et al. .................. 514/315
5,770,575 A * 6/1998 Beavers et al. .................. 514/19

FOREIGN PATENT DOCUMENTS

| EP | 0 445 796 | * | 9/1991 |
| WO | WO 91/07976 | * | 6/1991 |
| WO | WO 95/08536 | * | 3/1995 |
| WO | WO 95/11228 | * | 4/1995 |
| WO | WO 95/25091 | * | 9/1995 |

OTHER PUBLICATIONS

Hoekstra et al., Design and Evaluation of Nonpeptide Fibrinogen gamma–Chain Based GPIIb/IIIa Antagonists, Journal of Medicinal Chemistry, vol.38, No. 10, pp. 1582–1592, May 1995.*

Hoekstra et al., Adamantane and Nipecotic Acid Derivatives as Novel beta–turn Mimics, Bioorganic & Medicinal Chemistry Letters, vol. 4, No. 11, pp. 1361–1364, Oct. 1994.*

* cited by examiner

*Primary Examiner*—Brenda Coleman
(74) *Attorney, Agent, or Firm*—Oblon, Spivak, McClelland, Maier & Neustadt, P.C.

(57) ABSTRACT

β-alanine compounds or a pharmaceutically acceptable salt thereof, which is useful as a glycoprotein IIB/IIIa antagonist, inhibitor of blood platelet aggregation and inhibitor of the binding of fibrinogen to blood platelet; a composition containing the same, a process for the preparation of the compound, and a process for the treatment of diseases caused by thrombus formation, for example, are provided.

14 Claims, No Drawings ved
N-ACYLPIPERIDINYLCARBONYLAMINO-CARBOXYLIC ACIDS AND THEIR USE AS GLYCOPROTEIN IIB/IIIA ANTAGONISTS AND FIBRINOGEN-BLOOD PLATELETS BINDING INHIBITORS This application is a national stage entry under 35 U.S.C. §371 of PCT/JP96/00643 filed Mar. 14, 1996, published in English.

TECHNICAL FIELD

The present invention relates to β-alanine derivative and a pharmaceutically acceptable salt thereof. More particularly, it relates to β-alanine derivative and a salt thereof which is glycoprotein IIb/IIIa antagonist, inhibitor of blood platelets aggregation and inhibitor of the binding of fibrinogen to blood platelets.

BACKGROUND ART

In European Patent Application No. 512,831 A1, there are disclosed fibrinogen receptor antagonists.

In European Patent Application No. 445,796 A2, there are disclosed inhibitor of blood platelets aggregation.

DISCLOSURE OF INVENTION

The present invention relates to β-alanine derivative and a salt thereof. More particularly, it relates to β-alanine derivative and a salt thereof which is glycoprotein IIb/IIIa antagonist and inhibitor of platelet aggregation, and useful as:

a drug for the prevention and/or the treatment of diseases caused by thrombus formation such as arterial thrombosis; arterial sclerosis; ischemic heart diseases [e.g. angina pectoris (e.g. stable angina pectoris, unstable angina pectoris including imminent infarction, etc.), myocardial infarction (e.g. acute myocardial infarction, etc.), coronary thrombosis, etc.]; ischemic brain diseases [e.g. cerebral infarction {e.g. cerebral thrombosis (e.g. acute cerebral thrombosis, etc.), cerebral embolism, etc.}, transient cerebral ischemia (e.g. transient ischemic attack, etc.), cerebrovascular spasm after cerebral hemorrhage (e.g. cerebrovascular spasm after subarachnoid hemorrhage, etc.), etc.]; pulmonary vascular diseases (e.g. pulmonary thrombosis, pulmonary embolism etc.); peripheral circulatory disorder [e.g. arteriosclerosis obliterans, thromboangiitis obliterans (i.e. Burger's disease), Raynaud's disease, complication of diabetes mellitus (e.g. diabetic angiopathy, diabetic neuropathy, etc.), phlebothrombosis (e.g. deep vein thrombosis, etc.), etc.] or the like;

a drug for the prevention and/or the treatment of restenosis and/or reocclusion such as restenosis and/or reocclusion after percutaneous transluminal coronary angioplasty (PTCA), restenosis and/or reocclusion after the administration of thrombolytic drug (e.g. tissue plasminogen activator (TPA), etc.) or the like;

a drug for the adjuvant therapy with thrombolytic drug (e.g. TPA, etc.) or anticoagulant (e.g. heparin, etc.);

a drug for the prevention and/or the treatment of the thrombus formation in case of vascular surgery, valve replacement, extracorporeal circulation [e.g. surgery (e.g. open heart surgery, pump-oxygenator, etc.) hemodialysis, etc.], transplantation, or the like;

a drug for the prevention and/or the treatment of disseminated intravascular coagulation (DIC), thrombotic thrombocytopenia, essential thrombocytosis, inflammation (e.g. nephritis, etc.), immune diseases, or the like;

a drug for inhibiting of metastasis; or the like.

The β-alanine derivative of the present invention is expected to be useful as an inhibitor of cell adhesion and so is expected to be useful as a drug for the prevention and/or the treatment of disseminated intravascular coagulation (DIC), thrombotic thrombocytopenia, essential thrombocytosis, inflammation (e.g. nephritis, etc.), immune diseases, or the like;

a drug for inhibiting of metastasis; or the like.

The object β-alanine derivative of the present invention can be shown by the following formula (I):

$$R^1\text{-}(A^1)_m\text{-}\underset{O}{\overset{\|}{C}}\text{-}N\bigcirc\text{-}\underset{O}{\overset{\|}{C}}\text{-}\underset{H}{N}\text{-}A^2\text{-}R^2 \quad (I)$$

wherein $R^1$ is piperidyl, piperidyl having amino protective group, tetrahydropyridyl, tetrahydropyridyl having amino protective group, azetidinyl, azetidinyl having amino protective group, tetrahydroisoquinolyl or tetrahydroisoquinolyl having amino protective group, $R^2$ is carboxy or protected carboxy, $A^1$ is lower alkylene, lower alkanyl-ylidene, lower alkenylene, cyclo(lower)alkylene or arylene, $A^2$ is lower alkylene which may have one or more suitable substituent(s) or arylene,

—N◯— is piperidinediyl or tetrahydroisoquinolinediyl, and m is an integer of 0 or 1, with proviso that when $R^1$ is piperidyl, $A^1$ is lower alkylene, and $A^2$ is lower alkylene which may have one or more suitable substituent(s) except 5 or 6-membered heteromonocyclic group containing 1 to 2 oxygen atom(s) and 1 to 3 nitrogen atom(s), which may have one or more lower alkyl; ar(lower)alkoxy(lower)alkyl; hydroxy(lower) alkyl; lower alkoxy(lower)alkyl; cyclo(lower)alkyl; aroylamino(lower)alkyl; lower alkanoylamino(lower) alkyl which may have halogen; lower alkanoylamino having halogen; and aroylamino having halo(lower) alkyl;

then $R^2$ is pentyloxycarbonyl, isopentyloxycarbonyl, isohexyloxycarbonyl, phenethyloxycarbonyl, aryloxycarbonyl or indanyloxycarbonyl, or a salt thereof.

The object compound (I) or a salt thereof can be prepared by the following processes.

Process 1

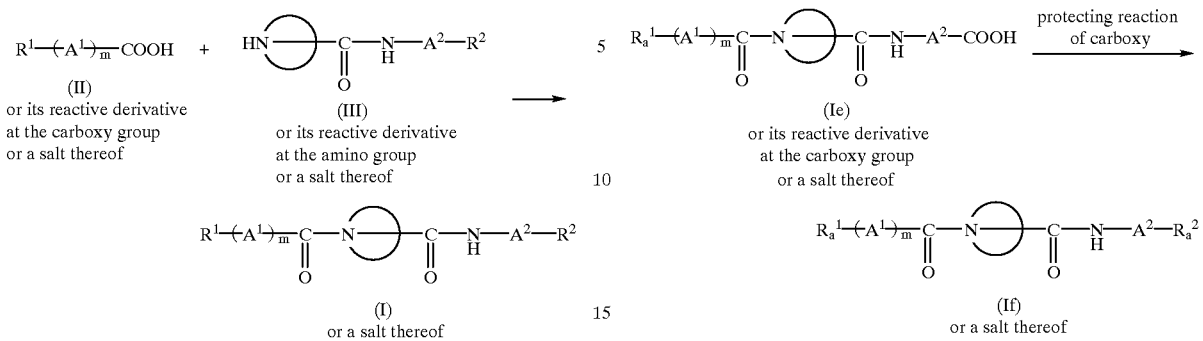

Process 2

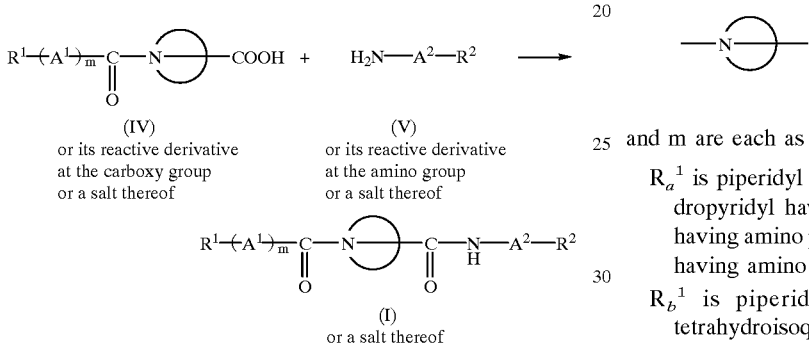

Process 3

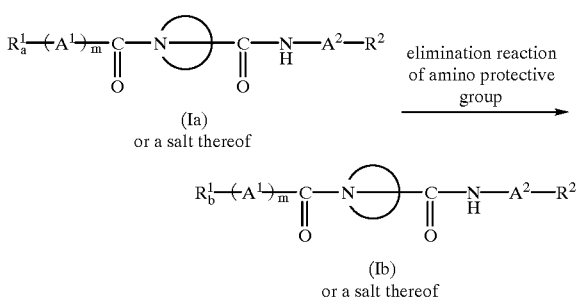

(Ia)
or a salt thereof

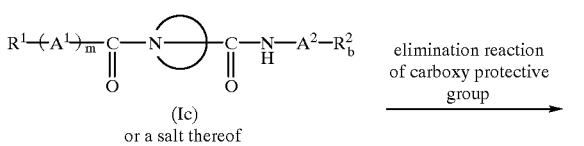

(Ib)
or a salt thereof

Process 4

Process 5 wherein $R^1$, $R^2$, $A^1$, $A^2$, and m are each as defined above, $R_a^1$ is piperidyl having amino protective group, tetrahydropyridyl having amino protective group, azetidinyl having amino protective group or tetrahydroisoquinolyl having amino protective group, $R_b^1$ is piperidyl, tetrahydropyridyl, azetidinyl or tetrahydroisoquinolyl, $R_a^2$ is protected carboxy, and is piperidyl or tetrahydroisoquinolyl.

The starting compound (IV) or a salt thereof is novel and can be prepared by the following schemes.

Process A

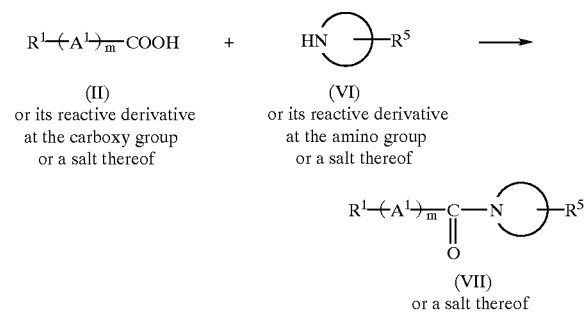

Process B

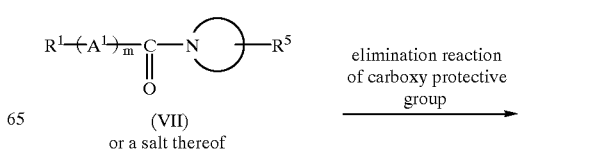

-continued

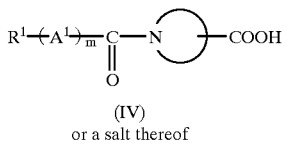

(IV)
or a salt thereof wherein $R^1$, $A^1$,

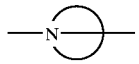

and m are each as defined above,
$R^5$ is protected carboxy, and

is piperidyl or tetrahydroisoquinolyl.

Among the starting compounds (II), (III), (V), (VI) and (VII), there are novel compounds. They can be prepared from the known compounds in a conventional manner in this field of the art or the similar manners to those disclosed in Preparations and/or Examples mentioned later in the present specification.

Suitable salts of the object compound (I) are pharmaceutically acceptable salts such as conventional non-toxic salts and include a metal salt such as an alkali metal salt [e.g. sodium salt, potassium salt, etc.] and an alkaline earth metal salt [e.g. calcium salt, magnesium salt, etc.] an ammonium salt, an organic base salt [e.g. trimethylamine salt, triethylamine salt, pyridine salt, picoline salt dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.] and the like.

In the above and subsequent descriptions of this specification, suitable examples of the various definitions are explained in detail as follows:

The term "lower" is intended to mean 1 to 6 carbon atom(s), unless otherwise indicated.

The term "higher" is used to intend a group having 7 to 20 carbon atoms, unless otherwise provided.

The preferable number of the "one or more" in the term "one or more suitable substituent(s)" may be 1 to 3.

Suitable "lower alkyl" may be straight or branched ones such as methyl, ethyl, isopropyl, propyl, butyl, isobutyl, sec-butyl, t-butyl, pentyl, isopentyl, hexyl, isohexyl or the like.

Suitable "protected carboxy" may be carboxy protected by a conventional protecting group such as an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, isopentyl ester, hexyl ester, isohexyl ester, 1-cyclopropylethyl ester, etc.] which may have suitable substituent(s), for example, lower alkanoyloxy (lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxyethyl ester, 2-propionyloxyethyl ester, hexanoyloxymethyl ester, etc.], lower-alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.];

higher alkyl ester [e.g. heptyl ester, octyl ester, 3,5-dimethyloctyl ester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];

lower alkenyl ester [e.g. ($C_2$–$C_6$)alkenyl ester (e.g. vinyl ester, allyl ester, etc.)];

lower alkynyl ester [e.g. ($C_2$–$C_6$)alkynyl ester (e.g. ethynyl ester, propynyl ester, etc.)];

ar(lower)alkyl ester which may have one or more suitable substituent(s) [e.g. phenyl(lower)alkyl ester which may have 1 to 4 lower alkoxy, halogen, nitro, hydroxy, lower alkyl, phenyl, or halo(lower)alkyl, (e.g. benzyl ester, 4-methoxybenzyl ester, 4-chlorobenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, 4-trifluoromethylbenzyl ester, etc.)];

aryl ester which may have one or more suitable substituent(s) [e.g. phenyl ester which may have 1 to 4 lower alkyl, or halogen, (e.g. phenyl ester, 4-chlorophenyl ester, tolyl ester, 4-tert-butylphenyl ester, xylyl ester, mesityl ester, cumenyl ester, etc.), indanyl ester, etc.];

cycloalkyloxycarbonyloxy(lower)alkyl ester which may have lower alkyl (e.g., cyclopentyloxycarbonyloxymethyl ester, cyclohexyloxycarbonyloxymethyl ester, cycloheptyloxycarbonyloxymethyl ester, 1-methylcyclohexyloxycarbonyloxymethyl ester, 1-(or 2-)-[cyclopentyloxycarbonyloxy]ethyl ester, 1-(or 2-)-[cyclohexyloxycarbonyloxy]ethyl ester, 1-(or 2-)-[cycloheptyloxycarbonyloxy]ethyl ester, etc.), etc.);

(5-(lower)alkyl-2-oxo-1,3-dioxol-4-yl)(lower)alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)methyl ester, 1-(or 2-)(5-methyl-2-oxo-1,3-dioxol-4-yl)ethyl ester, 1-(or 2-)(5-ethyl-2-oxo-1,3-dioxol-4-yl)ethyl ester, 1-(or 2-)(5-propyl-2-oxo-1,3-dioxol-4-yl)ethyl ester, etc.]; or the like, in which the preferred one may be lower alkyl ester, ar(lower)alkyl ester,. aryl ester which may have one or more suitable substituent(s) cycloalkyloxycarbonyloxy (lower)alkyl ester or lower alkanoyloxy(lower)alkyl ester, and the more preferred one may be methyl ester, ethyl ester, butyl ester, pentyl ester, isopentyl ester, isohexyl ester, phenethyl ester, phenyl ester, indanyl ester, pivaloyloxymethyl ester or 1-cyclohexyloxycarbonyloxyethyl ester.

Suitable "lower alkanyl-ylidene" may include straight or branched one such as methine, 1-ethanyl-2-ylidene, 1-propanyl-3-ylidene, 2-methyl-1-propanyl-3-ylidene, 7-pentanyl-5-ylidene, 1-hexanyl-6-ylidene and the like.

Suitable "lower alkylene" may include straight or branched one such as methylene, ethylene, trimethylene, tetramethylene, pentamethylene, hexamethylene, methylmethylene, 1-ethylethylene, 2-ethylpropylene, and the like, in which the preferred one may be ($C_1$–$C_4$)alkylene, and the more preferred one may be ethylene and propylene.

Suitable "lower alkenylene" may include straight or branched one having 2 to 6 carbon atom(s) such as vinylene, 1 or 2-propenylene, 1 or 2 or 3-butenylene, 1 or 2 or 3-pentenylene, 1 or 2 or 3-hexenylene, 1 or 2-methylvinylene, 1 or 2-ethylvinylene, 1 or 2 or 3-methylpropenylene, 1 or 2 or 3-ethylpropenylene, 1 or 2 or 3 or 4-methyl-1 or 2-butenylene, or the like, in which the preferred one may be ($C_2$–$C_4$)alkenylene, and the more preferred one may be vinylene, 1-propenylene, 1-methylvinylene and 2-methylvinylene.

Suitable "cyclo(lower)alkylene" may be cyclopropylene, cyclobutylene, cyclopentylene, cyclohexylene or the like, in which the preferred one may be cyclo($C_3$–$C_6$)alkylene, and the most preferred one may be cyclopropylene.

Suitable "arylene" may be phenylene, naphthylene, anthrylene or the like, in which the preferred one may be 1,2-phenylene, 1,3-phenylene and 1,4-phenylene.

Suitable "amino protective group" may include acyl group as explained below, a conventional protecting group such as ar(lower)alkyl which may have 1 to 3 suitable substituent(s) (e.g. benzyl, phenethyl, 1-phenylethyl, benzhydryl, trityl, etc.), [5-(lower)alkyl-2-oxo-1,3-dioxol-4-yl](lower)alkyl [e.g. (5-methyl-2-oxo-1,3-dioxol-4-yl) methyl, etc.] or the like; and the like.

Suitable "acyl group" and "acyl" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows:

aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

aromatic acyl such as aroyl (e.g., benzoyl, toluoyl, naphthoyl, etc.);

ar(lower)alkanoyl [e.g., phenyl($C_1$–$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$–$C_6$)alkanoyl (e.g., naphthylacetyl, naphthylpropanoyl, naphthylbutanoyl, etc), etc.];

ar(lower)alkenoyl [e.g., phenyl($C_3$–$C_6$)alkenoyl (e.g., phenylpropenoyl, phenylbutenoyl, phenylmethacryloyl, phenylpentenoyl, phenylhexenoyl, etc.), naphthyl($C_3$–$C_6$)alkenoyl (e.g., naphthylpropenoyl, naphthylbutenoyl, etc.), etc.];

ar(lower)alkoxycarbonyl [e.g., phenyl($C_1$–$C_6$) alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.);

arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.); or the like;

heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like; and the like.

Suitable "heterocyclic moiety" in the terms "heterocycliccarbonyl", "heterocyclic(lower)alkyl", "heterocyclic(lower)alkanoyl" and "heterocyclicglyoxyloyl" as mentioned above, and "heterocyclic group" mean saturated or unsaturated monocyclic or polycyclic heterocyclic group containing at least one hetero-atom such as an oxygen, sulfur, nitrogen atom and the like, in which the preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, dihydroquinolyl, isoquinolyl, indazolyl, quinoxalinyl, dihydroquinoxalinyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as mentioned above may have one to ten, same or different, suitable substituent(s) such as lower alkyl (e.g., methyl, ethyl, propyl, etc.);

lower alkoxy (e.g., methoxy, ethoxy, propoxy, etc.);

lower alkylthio (e.g., methylthio, ethylthio, etc.);

lower alkylamino (e.g., methylamino, ethylamino, propylamino, etc.);

cyclo(lower)alkyl [e.g. cyclo($C_3$–$C_6$)alkyl (e.g., cyclopentyl, cyclohexyl, etc.]);

cyclo(lower)alkenyl [e.g. cyclo($C_3$–$C_6$)alkenyl (e.g., cyclohexenyl, cyclohexadienyl, etc);

halogen (e.g., fluorine, chlorine, bromine, iodine); amino; amino protective group as mentioned above; hydroxy; protected hydroxy as mentioned below; cyano; nitro; carboxy; protected carboxy as mentioned above; sulfo; sulfamoyl; imino; oxo;

amino(lower)alkyl (e.g., aminomethyl, aminoethyl, etc.); carbamoyloxy; hydroxy(lower)alkyl (e.g., hydroxymethyl, 1 or 2-hydroxyethyl, 1 or 2 or 3-hydroxypropyl, etc.), or the like.

Suitable "protected hydroxy" may include acyl as mentioned above, phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

The more preferred example of "amino protective group" may be lower alkoxycarbonyl or ar(lower)alkoxycarbonyl and the most preferred one may be t-butoxycarbonyl or benzyloxycarbonyl.

Suitable "lower alkylene" in the term "lower alkylene which may have one or more suitable substituent(s)" can be referred to the ones as exemplified above.

Suitable example of "suitable substituent(s)" in the term "lower alkylene which may have one or more suitable substituent(s)" may include lower alkyl (e.g., methyl, ethyl, propyl, isopropyl, butyl, isobutyl, t-butyl, pentyl, neopentyl, t-pentyl, hexyl, etc.);

lower alkoxy (e.g., methoxy, ethoxy, propoxy, isopropoxy, isobutoxy, t-butoxy, pentyloxy, neopentyloxy, t-pentyloxy, hexyloxy, etc.);

lower alkenyl [e.g. ($C_2$–$C_6$)alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.)];

lower alkynyl [e.g. ($C_2$–$C_6$)alkynyl (e.g., ethynyl, 1-propynyl, propargyl, 1-methylpropargyl, 1-ethylpropargyl, 1 or 2 or 3-butynyl, 1 or 2 or 3 or 4-pentynyl, 1 or 2 or 3 or 4 or 5 hexynyl, etc.)];

mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.);

halogen (e.g., chlorine, bromine, fluorine, iodine);

carboxy; protected carboxy as mentioned above; hydroxy; protected hydroxy as mentioned above;

aryl (e.g., phenyl, naphthyl, etc.);

heterocyclic group as mentioned above [e.g. unsaturated 3 to 8-membered (more preferably 5 or 6-membered) heteromonocyclic group containing 1 to 2 oxygen atom(s) and 1 to 3 nitrogen atom(s) for example, oxazolyl, isoxazolyl, oxadiazolyl (e.g., 1,2,4-oxadiazolyl, 1,3,4-oxadiazolyl, 1,2,5-oxadiazolyl, etc.), unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.), in which said heteromonocyclic group as mentioned above may have one or more, same or different, suitable substituent(s) such as lower alkyl (e.g., methyl, ethyl, propyl, etc.), lower alkoxy (e.g., methoxy, ethoxy, propoxy, etc.), or the like];

ar(lower)alkyl such as phenyl(lower)alkyl (e.g., benzyl, phenethyl, phenylpropyl, etc.);

ar(lower)alkyl having one or more suitable substituents such as ar(lower)alkyl having one or more (preferably 1 to 4) lower alkoxy, halogen, cyano, halo(lower)alkyl, lower alkylene dioxy or the like;

carboxy(lower)alkyl; protected carboxy(lower)alkyl; nitro; amino;

protected amino, i.e. amino protected by aforesaid "amino protective group", preferably, acylamino, in which acyl moiety can be aforementioned "acyl", such as aliphatic acylamino such as lower or higher alkanoylamino which may have one or more suitable substituent(s) (e.g., formylamino, acetylamino, trifluoroacetylamino, propanoylamino, butanoylamino, 2-methylpropanoylamino, pentanoylamino, 2,2-dimethylpropanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, nonadecanoylamino, icosanoylamino, etc.), cyclo(lower)alkylcarbonylamino [e.g. cyclo($C_3$–$C_6$) alkylcarbonylamino (e.g. cyclopropylcarbonylamino, cyclobutylcarbonylamino, cyclopentylcarbonylamino, cyclohexylcarbonylamino, etc.)], lower or higher alkoxycarbonylamino (e.g., methoxycarbonylamino, ethoxycarbonylamino, t-butoxycarbonylamino, pentyloxycarbonylamino, heptyloxycarbonylamino, etc.), lower alkoxy(lower)alkanoylamino (e.g. methoxyacetylamino, 2- or 3-methoxypropionylamino, ethoxyacetylamino, 2- or 3-ethoxypropionylamino, etc.), lower alkynylcarbonylamino [e.g. ($C_2$–$C_6$) alkynylcarbonylamino (e.g. propargylcarbonylamino, 1-methylpropargylcarbonylamino, 1- or 2- or 3-butynylcarbonylamino, etc.), lower or higher alkylsulfonylamino (e.g., methylsulfonylamino, ethylsulfonylamino, propylsulfonylamino, n-butylsulfonylamino, sec-butylsulfonylamino, t-butylsulfonylamino, n-pentylsulfonylamino, neopentylsulfonylamino, hexylsulfonylamino, etc.), lower or higher alkoxysulfonylamino (e.g., methoxysulfonylamino, ethoxysulfonylamino, etc.), aroylamino which may have one or more (preferably 1 to 3) suitable substituent(s) (e.g. benzoylamino, toluoylamino, naphthoylamino, 2- or 3- or 4-hydroxybenzoylamino, 2- or 3- or 4-methoxybenzoylamino, 2- or 3- or 4-chlorobenzoylamino, 2- or 3- or 4-trifluorobenzoylamino, phenylbenzoylamino, etc.), ar(lower)alkanoylamino [e.g., phenyl($C_1$–$C_6$)alkanoylamino (e.g., phenylacetylamino, phenylpropanoylamino, phenylbutanoylamino, phenylisobutanoylamino, phenylpentanoylamino, phenylhexanoylamino, etc.), naphthyl(lower)alkanoylamino (e.g., naphthylacetylamino, naphthylpropanoylamino, naphthylbutanoylamino, etc.), etc.], ar(lower)alkenoylamino [e.g., phenyl($C_3$–$C_6$)alkenoylamino (e.g., phenylpropenoylamino, phenylbutenoylamino, phenylmethacryloylamino, phenylpentenoylamino, phenylhexenoylamino, etc.), naphthyl($C_3$–$C_6$)alkenoylamino (e.g., naphthylpropenoylamino, naphthylbutenoylamino, etc.), etc.], ar(lower)alkoxycarbonylamino [e.g., phenyl($C_1$–$C_6$)alkoxycarbonylamino (e.g. benzyloxycarbonylamino, phenethyloxycarbonylamino, etc.), etc.], aryloxycarbonylamino (e.g., phenoxycarbonylamino, naphthyloxycarbonylamino, etc.), aryloxy(lower)alkanoylamino (e.g., phenoxyacetylamino, phenoxypropionylamino, etc.), arylcarbamoylamino (e.g., phenylcarbamoylamino, etc.), arylthiocarbamoylamino (e.g., phenylthiocarbamoylamino, etc.), arylglyoxyloylamino (e.g., phenylglyoxyloylamino, naphthylglyoxyloylamino, etc.), arylsulfonylamino (e.g. phenylsulfonylamino, p-tolylsulfonylamino, etc.), or the like;

di(lower)alkylamino (e.g., dimethylamino, diethylamino, diisopropylamino, ethylmethylamino, isopropylmethylamino, ethylmethylamino, ethylpropylamino, etc.);

hydroxy(lower)alkyl; protected hydroxy(lower)alkyl; acyl as mentioned above; cyano; mercapto; oxo;

lower alkylthio(lower)alkyl (e.g. methylthiomethyl, ethylthiomethyl, propylthiomethyl, isopropylthiomethyl, butylthiomethyl, methylthioethyl, ethylthioethyl, etc.);

arylthio(lower)alkyl (e.g. phenylthiomethyl, phenylthioethyl, etc.);

arylsulfonyl(lower)alkyl (e.g. phenylsulfonylmethyl, phenylsulfonylethyl, p-tolylsulfonylmethyl, p-tolylsulfonylethyl, etc.);

lower alkylsulfonyl(lower)alkyl (e.g. methylsulfonylmethyl, ethylsulfonylmethyl, propylsulfonylmethyl, etc.);

acylamino(lower)alkyl which may have one or more suitable substituent(s), in which acyl moiety can be aforementioned "acyl" [e.g., arylsulfonylamino(lower)alkyl (e.g., phenylsulfonylaminomethyl, phenylsulfonylaminoethyl, p-tolylsulfonylaminomethyl, p-tolylsulfonylethyl, etc.), lower alkylsulfonylamino(lower)alkyl (e.g., methylsulfonylaminomethyl, ethylsulfonylaminomethyl, propylsulfonylaminomethyl, butylsulfonylaminomethyl, t-butylsulfonylaminomethyl, pentylsulfonylaminoethyl, etc.), lower alkanoylamino(lower)alkyl which may have one or more suitable substituent(s) (e.g., acetylaminomethyl, acetylaminoethyl, trifluoroacetylaminomethyl, trifluoroacetylaminoethyl, etc.), aroylamino(lower)alkyl (e.g., benzoylaminomethyl, benzoylaminoethyl, naphthoylaminomethyl, etc.), etc.];

lower alkylcarbonyl(lower)alkyl (e.g. methylcarbonylmethyl, ethylcarbonylmethyl, propylcarbonylmethyl, etc.);

aroyl(lower)alkyl (e.g. benzoylmethyl, naphthoylmethyl, toluoylmethyl, anisoylmethyl, etc.);

heterocyclic(lower)alkyl such as (lower)alkyl having heterocyclic group as exemplified above [e.g. ($C_1$–$C_6$)alkyl having unsaturated condensed heterocyclic group containing 1 to 4 nitrogen atom(s) (e.g. indolylethyl, isoindolylethyl, indolyinylmethyl, indolizinylethyl, benzimidazolylmethyl, quinolylethyl, dihydroquinolylmethyl, isoquinolylethyl, indazolylethyl, quinoxalinylethyl, dihydroquinoxalinylmethyl, benzotriazolylethyl, etc.)];

lower alkyl sulfamoyl(lower)alkyl (e.g. methylsulfamoylmethyl, ethylsulfamoylmethyl, n-propylsulfamoylmethyl, isopropylsulfamoylmethy, n-butylsulfamoylmethyl, t-butylsulfamoylmethyl, methylsulfamoylethyl, etc.);

arylsulfamoyl(lower)alkyl (e.g. phenylsulfamoylmethyl, tolylsulfamoylmethyl, phenylsulfamoylethyl, naphthylsulfamoylmethyl, etc.);

lower alkylcarbamoyl(lower)alkyl (e.g. methylcarbamoylmethyl, ethylcarbamoylmethyl, n-propylcarbamoylmethyl, isopropylcarbamoylmethyl, n-butylcarbamoylmethyl, t-butylcarbamoylmethyl, methylcarbamoylethyl, etc.);

arylcarbamoyl(lower)alkyl (e.g. phenylcarbamoylmethyl, tolylcarbamoylmethyl, phenylcarbamoylethyl, naphthylcarbamoylmethyl, etc.);

ar(lower)alkylcarbamoyl which may have one or more suitable substituent(s) [e.g. phenyl($C_1$–$C_6$)alkylcarbamoyl which may have 1 to 3 lower alkoxy (e.g. 2-methoxyphenethylcarbamoyl, 3-methoxyphenethylcarbamoyl, 4-methoxyphenethylcarbamoyl, etc.);

lower alkoxy(lower)alkyl (e.g., methoxymethyl, methoxyethyl, ethoxymethyl, ethoxyethyl, propoxyethyl, propoxyethyl, butoxybutyl, pentyloxymethyl, hexyloxyethyl, etc.);

cyclo(lower)alkyl (e.g., cyclopropyl, cyclobutyl, cyclopentyl, cyclohexyl, etc.);

ar(lower)alkoxy(lower)alkyl (e.g., benzyloxymethyl, benzyloxyethyl, benzyloxypropyl, benzyloxybutyl, benzyloxypentyl, benzyloxyhexyl, phenethyloxymethyl, phenethyloxyethyl, etc.) and the like, in which the more preferred "suitable substituent (s)" in the term "lower alkylene which may have one or more suitable substituent(s)" may be ($C_1$–$C_6$)alkyl; ($C_2$–$C_6$)alkynyl; phenyl; phenyl($C_1$–$C_6$)alkyl; ($C_1$–$C_6$)alkanoylamino; aroylamino; 5 or 6-membered heteromonocyclic group containing 1 to 2 oxygen atom(s) and 1 to 3 nitrogen atom(s) which may have lower alkyl;

5 or 6-membered heteromonocyclic group containing 1 to 4 nitrogen atom(s);

phenyl($C_1$–$C_6$)alkyl having 1 or 2 ($C_1$–$C_6$)alkoxy;

($C_1$–$C_6$)alkoxy($C_1$–$C_6$)alkyl;
cyclo($C_1$–$C_6$)alkyl; hydroxy($C_1$–$C_6$)alkyl;
phenyl($C_1$–$C_6$)alkoxy($C_1$–$C_6$)alkyl;
($C_1$–$C_6$)alkanoylamino($C_1$–$C_6$)alkyl having 1 to 3 halogen;
aroylamino having 1 to 3 halo(lower)alkyl;
($C_1$–$C_6$)alkanoylamino having 1 to 3 halo(lower)alkyl;
aroylamino having ($C_1$–$C_6$)alkoxy;
aroylamino($C_1$–$C_6$)alkyl; or ($C_1$–$C_6$)alkanoylamino($C_1$–$C_6$)alkyl;
and the most preferred one may be methyl, ethynyl, phenyl, phenethyl, acetylamino, benzoylamino, 3- or 4- or 5-methyl isoxazolyl, triazolyl, 4-methoxyphenethyl, 3,4-dimethoxyphenethyl, methoxymethyl, cyclopropyl, hydroxymethyl, benzyloxymethyl, trifluoroacetylaminomethyl, trifluorobenzoylamino, trifluoroacetylamino, methoxybenzoylamino, benzoylaminomethyl or acetylaminomethyl.

In the compound (I) as explained above, the preferred one is the following compound (I-A):

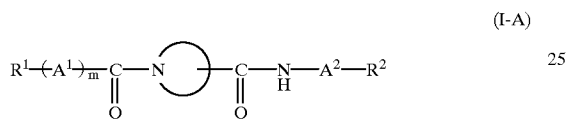

(I-A)

wherein
$R^1$ is piperidyl, piperidyl having amino protective group, tetrahydropyridyl, tetrahydropyridyl having amino protective group, azetidinyl, azetidinyl having amino protective group, tetrahydroisoquinolyl, or tetrahydroisoquinolyl having amino protective group,
$R^2$ is carboxy or protected carboxy,
$A^1$ is lower alkenylene,
$A^2$ is lower alkylene, lower alkylene which may have 1 to 3 suitable substituent(s) selected from the group consisting of lower alkyl, lower alkynyl, aryl, ar(lower)alkyl which may have 1 to 3 lower alkoxy, lower alkanoylamino which may have 1 to 3 halogen, aroylamino which may have 1 to 3 halo(lower)alkyl, heterocyclic group which may have 1 to 3 lower alkyl, lower alkoxy(lower)alkyl, cyclo(lower)alkyl, hydroxy(lower)alkyl, ar(lower)alkoxy(lower)alkyl and lower alkanoylamino(lower)alkyl which may have 1 to 3 halogen or arylene,

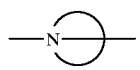

is piperidinediyl or tetrahydroisoquinolinediyl, and
m is an integer of 1,
and the more preferred one is the aforementioned compound (I-A), wherein
$R^1$ is piperidyl, piperidyl having amino protective group, tetrahydropyridyl, tetrahydropyridyl having amino protective group, azetidinyl, azetidinyl having amino protective group, tetrahydroisoquinolyl or tetrahydroisoquinolyl having amino protective group,
$R^2$ is carboxy or protected carboxy,
$A^1$ is lower alkenylene,
$A^2$ is lower alkylene, lower alkylene which has one suitable substituent selected from the group consisting of lower alkyl, lower alkynyl, aryl, ar(lower)alkyl which may have 1 or 2 lower alkoxy, lower alkanoylamino which may have 3 halogens, aroylamino which may have one tri-halo(lower)alkyl, 5 or 6-membered heteromonocyclic group containing 1 to 2 oxygen atom(s) which may have one lower alkyl, 5 or 6-membered heteromonocyclic group containing 1 to 4 nitrogen atom(s), lower alkoxy(lower)alkyl, cyclo(lower)alkyl, hydroxy(lower)alkyl, ar(lower)alkoxy(lower)alkyl and lower alkanoylamino(lower)alkyl which may have 3 halogens or phenylene,

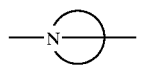

is piperidinediyl or tetrahydroisoquinolinediyl and
m is an integer of 1,
and the much more preferred one is the aforementioned compound (I-A), wherein
$R^1$ is piperidyl or tetrahydropyridyl,
$R^2$ is carboxy or protected carboxy,
$A^1$ is lower alkenylene,
$A^2$ is lower alkylene or lower alkylene which has one suitable substituent selected from the group consisting of lower alkyl, lower alkynyl, phenyl, phenyl(lower)alkyl which may have 1 or 2 lower alkoxy, lower alkanoylamino, benzoylamino which may have one tri-halo(lower)alkyl, isoxazolyl which has one lower alkyl, triazolyl and phenyl(lower)alkoxy(lower)alkyl,

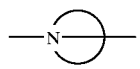

is piperidinediyl, and
m is an integer of 1,
and the most preferred one is the aforementioned compound (I-A), wherein
$R^1$ is 4-piperidyl or 4-tetrahydropyridyl,
$R^2$ is carboxy or protected carboxy,
$A^1$ is vinylene,
$A^2$ is lower alkylene or lower alkylene which has one substituent selected from the group consisting of methyl, ethynyl, phenyl, phenethyl, acetylamino, benzoylamino, isoxazolyl having methyl, triazolyl, methoxyphenethyl, dimethoxyphenethyl, benzyloxymethyl and trifluorobenzoylamino,

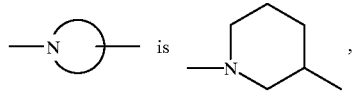

and
m is an integer of 1.

In the compound (I) as explained above, another preferred one is the following compound (I-B):

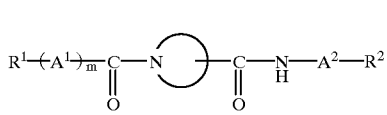
(I-B)

wherein
R¹ is piperidyl,
R² is pentyloxycarbonyl, isopentyloxycarbonyl, isohexyloxycarbonyl, phenethyloxycarbonyl, phenyloxycarbonyl or indanyloxycarbonyl,
A¹ is lower alkylene,
A² is lower alkylene which has one substituent selected from the group consisting of lower alkynyl and lower alkanoylamino,

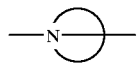

is piperidinediyl, and
m is an integer of 1,
and the much more preferred one is the aforementioned compound (I-B), wherein
R¹ is 4-piperidyl,
R² is pentyloxycarbonyl, isopentyloxycarbonyl, isohexyloxycarbonyl, phenethyloxycarbonyl, phenyloxycarbonyl or indanyloxycarbonyl,
A¹ is ethylene,
A² is lower alkylene which has one substituent selected from the group consisting of ethynyl and acetylamino,

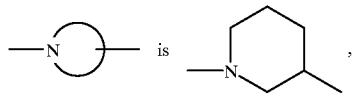

and
m is an integer of 1.

In the compound (I) as explained above, another preferred one is the following compound (I-C):

(I-C)

wherein
R¹ is piperidyl or piperidyl having amino protective group,
R² is carboxy or protected carboxy,
A¹ is lower alkylene,
A² is lower alkylene which has one substituent selected from the group consisting of 5 or 6-membered heteromonocyclic group containing 1 to 2 oxygen atom(s) and 1 to 3 nitrogen atom(s) having lower alkyl, phenyl (lower)alkoxy(lower)alkyl, hydroxy(lower)alkyl, lower alkoxy(lower)alkyl, cyclo(lower)alkyl, benzoylamino(lower)alkyl, lower alkanoylamino (lower)alkyl, tri-halo(lower)alkanoylamino, benzoylamino having tri-halo(lower)alkyl and tri-halo(lower) alkanoylamino(lower)alkyl or arylene,

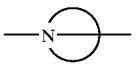

is piperidinediyl, and
m is an integer of 1,
and the more preferred one is the aforementioned compound (I-C), wherein
R¹ is piperidyl,
R² is carboxy,
A¹ is lower alkylene,
A² is lower alkylene which has one substituent selected from the group consisting of isoxazolyl having lower alkyl, tri-halo(lower)alkylbenzoylamino, benzoylamino(lower)alkyl, tri-halo(lower) alkanoylamino(lower)alkyl,

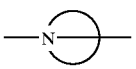

is piperidinediyl, and
m is an integer of 1,
and the most preferred one is the aforementioned compound (I-C), wherein
R¹ is 4-piperidyl,
R² is carboxy,
A¹ is lower alkylene,
A² is lower alkylene which has one substituent selected from the group consisting of isoxazolyl having methyl, trifluorobenzoylamino, benzoylaminomethyl and trifluoroacetylaminomethyl,

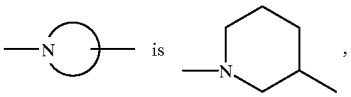

and
m is an integer of 1.

In the compound (I) as explained above, another preferred one is the following compound (I-D):

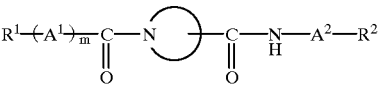
(I-D)

wherein
R¹ is tetrahydropyridyl or tetrahydropyridyl having amino protective group,
R² is carboxy or protected carboxy,
A¹ is lower alkylene,
A² is lower alkylene which has one substituent selected from the group consisting of lower alkynyl and 5 or 6-membered heteromonocyclic group containing 1 to 2 oxygen atom(s) and 1 to 3 nitrogen atom(s) having lower alkyl,

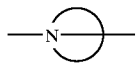

is piperidinediyl, and m is an integer of 1, and the more preferred one is the aforementioned compound (I-D), wherein
$R^1$ is tetrahydropyridyl,
$R^2$ is carboxy,
$A^1$ is lower alkylene,
$A^2$ is lower alkylene which has one substituent selected from the group consisting of lower alkynyl and isoxazolyl having lower alkyl,

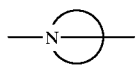

is piperidinediyl, and m is an integer of 1, and the most preferred one is the aforementioned compound (I-D), wherein
$R^1$ is 4-tetrahydropyridyl,
$R^2$ is carboxy,
$A^1$ is lower alkylene,
$A^2$ is lower alkylene which has one substituent selected from the group consisting of ethynyl and isoxazolyl having methyl,

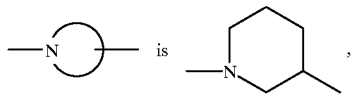

and m is an integer of 1.

The processes for preparing the object compound (I) of the present invention are explained in detail in the following.

Process 1

The object compound (I) or a salt thereof can be prepared by reacting a compound (II) or its reactive derivative at the carboxy group or a salt thereof with a compound (III) or its reactive derivative at the amino group or a salt thereof.

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl

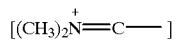

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivative can optionally be selected from them according to the kind of the compound (II) to be used.

Suitable salts of the compound (II) and its reactive derivative can be referred to the ones as exemplified for the compound (I).

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl) acetamide, bis(trimethylsilyl)urea or the like; a derivative formed by reaction of the compound (III) with phosphorus trichloride or phosgene, and the like.

Suitable salts of the compound (III) and its reactive derivative can be referred to the ones as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) in used in a free acid form or its salt form, the reaction is preferable carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkylphosphite; ethyl polyphosphate; isopropyl polyphosphate; phosphorous oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower) alkylbenzylamine, or the like.

The reaction temperature is not critical, and the reaction is usually carried out under cooling to warming.

Process 2

The object compound (I) or a salt thereof can be prepared by reacting a compound (IV) or its reactive derivative at the carboxy group or a salt thereof with a compound (V) or its reactive derivative at the amino group or a salt thereof.

This reaction can be carried out in a similar manner to that of Process 1 mentioned in the above, and therefore the reaction mode and reaction conditions [e.g. reactive derivative, solvent, reaction temperature, etc.] of this reaction are to be referred to those as explained in Process 1.

Process 3

The object compound (Ib) or a salt thereof can be prepared by subjecting a compound (Ia) or a salt thereof to elimination reaction of amino protective group.

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium, sulfate, palladium on barium carbonate, etc.], nickel catalysts [e.g. reduced nickel, nickel oxide, Raney nickel, etc.], cobalt catalysts (e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The present invention includes within the scope of the invention the case that protected carboxy in $R^2$ is transformed into carboxy.

Process 4

The object compound (Id) or a salt thereof can be prepared by subjecting a compound (Ic) or a salt thereof to elimination reaction of the carboxy protective group.

This reaction can be carried out in a similar manner to that of Process 3 mentioned in the above, and therefore the reaction mode and reaction conditions [e.g. base, acid, catalyst, solvent, reaction temperature, etc.] of this reaction are to be referred to those as explained in Process 3.

Process 5

The object compound (If) or a salt thereof can be prepared by subjecting the compound (Ie) or a salt thereof to protecting reaction of carboxy.

This reaction can be carried out according to a conventional manner such as the ones described in Examples or the similar manners thereto.

The processes for preparing the starting compound (IV) is explained in detail in the following.

Process A

The object compound (VII) or a salt thereof can be prepared by reacting a compound (II) or its reactive derivative at the carboxy group or a salt thereof with a compound (VI) or its reactive derivative at the amino group or a salt thereof.

This reaction can be carried out in a similar manner to that of Process 1 mentioned in the above, and therefore the reaction mode and reaction conditions [e.g. reactive derivative, solvent, reaction temperature, etc.] of this reaction are to be referred to those as explained in Process 1.

Process B

The object compound (IV) or a salt thereof can be prepared by subjecting a compound (VII) or a salt thereof to elimination reaction of the carboxy protective group.

This reaction can be carried out in a similar manner to that of Process 3 mentioned in the above, and therefore the reaction mode and reaction conditions [e.g. base, acid, catalyst, solvent, reaction temperature, etc.] of this reaction are to be referred to those as explained in Process 3.

The present invention includes within the scope of the invention the case that amino protective group in $R^1$ is transformed into amino.

When the object compound (I) obtained by the above-mentioned processes is in a free form, it can be converted into a salt form in a conventional manner. On the other hand, when the object compound (I) thus obtained is in a salt form, it can be converted into a free form or another salt form also in a conventional manner.

The compounds obtained by the above Processes 1 to 5 and A to B can be isolated and purified by a conventional method such as pulverization, recrystallization, column-chromatography, reprecipitation or the like.

It is to be noted that each of the object compound (I) may include one or more stereoisomer such as optical isomer(s) and geometrical isomer(s) due to asymmetric carbon atom(s)

and double bond(s) and all such isomers and mixture thereof are included within the scope of this invention.

The object compound (I) or a pharmaceutically acceptable salt thereof include solvated compound [e.g., enclosure compound (e.g., hydrate, etc.)].

The object compound (I) or a pharmaceutically acceptable salt thereof include both its crystal form and non-crystal form.

Now in order to show the utility of the object compound (I), some pharmacological test data of the representative compound (I) of the present invention are shown in the following.

Test 1: Effect on Platelet Aggregation Induced by Adenosine Diphosphate (ADP)

Test Compound (1) the compound of Example 25

Test Method

Platelet rich plasma (PRP) which contains $3 \times 10^8$ platelets/ml was prepared from human blood. To the 225 µl of PRP, 25 µl of drug solution* was added, and then stirred for 2 minutes at 37° C. To the solution 5 µl of ADP (final 2.5 µM) was added as an aggregation inducer. Aggregation was measured by using an aggregometer (NBS HEMA-TRACER 801). Activity of inhibitor (test compound) was expressed as $IC_{50}$ value i.e. dose required for complete inhibition of platelet aggregation.

Drug solution* - - - Test compound was dissolved in water.

Test Result

| Test Compound | $IC_{50}$ (µM) |
|---|---|
| (1) | 0.085 |

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used.

The object compound (I) or a pharmaceutically acceptable salt thereof is/are included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation including aerosols from metered dose inhalator, nebulizer or dry powder inhalator.

While the dosage of therapeutically effective amount of the object compound (I) varies from and also depends upon the age and condition of each individual patient to be treated, in the case of intravenous administration, a daily dose of 0.001–100 mg of the object compound (I) per kg weight of a human being or an animal, in the case of intramuscular administration, a daily dose of 0.001–100 mg of the object compound (I) per kg weight of a human being or an animal, in case of oral administration, a daily dose of 0.001–200 mg of the object compound (I) per kg weight of a human being or an animal in generally given for the prevention and/or the treatment of aforesaid diseases in a human being or an animal.

The following Preparations and Examples are given for the purpose of illustrating the present invention in more detail.

PREPARATION 1

To a solution of ethyl 3 azido-2(S)-aminopropionate hydrochloride (0.3 g) in dichloromethane (3 ml) was added triethylamine (0.47 ml) and benzoyl chloride (0.2 ml) under stirring at 0° C. After stirring at ambient temperature for 2 hours, the mixture was poured into water and extracted with dichloromethane. The extract was washed with water, saturated aq. $NaHCO_3$, water and brine, and dried over magnesium sulfate, and evaporated in vacuo. The residue was recrystallized from diethyl ether to give ethyl 3 azido-2(S)-(benzoylamino)propionate (0.35 g).

mp: 56° C.; IR (Nujol): 3260, 2090, 1730, 1640 $cm^{-1}$; NMR ($CDCl_3$, δ): 1.34 (3H, t, J=7.1 Hz), 3.88 (2H, qd, J=9.0 and 3.3 Hz), 4.32 (2H, d, J=7.1 Hz), 4.91–4.98 (1H, m), 6.96–7.04 (1H, m), 7.42–7.59 (3H, m), 7.81–7.86 (2H, m); MASS (m/z): 263 ($M^+$+1).

PREPARATION 2

A mixture of ethyl 3-azido-2(S)-(benzoylamino) propionate (0.35 g) and 10% Pd—C (0.07 g) in ethanol (4 ml) was hydrogenated at an atmospheric pressure for 2 hours. After the catalyst was removed by filtration, the filtrate was concentrated in vacuo to give ethyl 3-amino-2 (S)-(benzoylamino)propionate (0.25 g).

mp: 59° C.; IR (Nujol): 3320, 1730, 1630 $cm^{-1}$; NMR (DMSO-$d_6$, δ): 1.19 (3H, t, J=7.0 Hz), 2.93–2.97 (2H, m), 4.11 (2H, q, J=7.1 Hz), 4.36–4.45 (1H, m), 7.44–7.56 (3H, m), 7.87–7.92 (2H, m), 8.59 (1H, d, J=7.0 Hz); MASS (m/z): 237 ($M^+$+1).

PREPARATION 3 tert-butyldimethylsilyl chloride (1.42 g) was added to a mixture of 4(S)-ethynyl-2-azetidinone (0.78 g) in dichloromethane (10 ml) and ethyldiisopropylamine (2.14 ml) at room temperature. The reaction mixture was stirred overnight, then evaporated in vacuo. The residue was purified by column chromatography on silica gel eluting with n-hexane-ethyl acetate (9:1) to give 1-tert-butyldimethylsilyl-4(S)-ethynyl-2-azetidinone (1.4 g) as a colorless oil.

IR (Nujol): 3280, 1730 $cm^{-1}$; NMR ($CDCl_3$, δ): 0.28 (3H, s), 0.29 (3H, s), 0.98 (9H, s), 2.45 (1H, d, J=2.0 Hz), 3.10 (3H, dd, J=3.0 and 15.1 Hz), 3.40 (3H, dd, J=5.7 and 15.1 Hz), 4.10–4.15 (1H, m); MASS (m/z): 210 ($M^+$+1).

PREPARATION 4

A solution of phenylisocyanate (0.93 ml) in benzene (5 ml) was added to a mixture of 1-tert-butyldimethylsilyl-4

(S)-ethynyl-2-azetidinone (1.0 g) in benzene (10 ml), nitroethane (0.35 ml), and triethylamine (0.1 ml) in benzene (5 ml) at room temperature. The reaction mixture was refluxed for 8 hours, then evaporated in vacuo. The residue was purified by column chromatography on silica gel eluting with n-hexane-ethyl acetate (9:1) to give 1-tert-butyldimethylsilyl-4(S)-(3-methyl-5-isoxazolyl)-2-azetidinone (0.96 g) as a colorless oil.

IR (Film): 3120, 1740, 1605 cm$^{-1}$; NMR (CDCl$_3$, δ): 0.05 (3H, s), 0.77 (3H, s), 0.91 (9H, s), 2.31 (3H, s), 3.22 (3H, dd, J=3.0 and 15.3 Hz), 3.51 (3H, dd, J=5.8 and 15.3 Hz), 4.66 (3H, dd, J=3.0 and 5.8 Hz), 6.11 (1H, s); MASS (m/z): 267 (M$^+$+1).

PREPARATION 5

A solution of 1-tert-butyldimethylsilyl-4(S)-(3-methyl-5-isoxazolyl)-2-azetidinone (0.9 g) in EtOH (10 ml) was added HCl (16.9 mmol)/EtOH (4.2 ml) at room temperature at 0° C. The reaction mixture was stirred at room temperature for 2 hours, then evaporated in vacuo. The residue was recrystallized from diethyl ether to give 3(S)-(3-methyl-5-isoxazolyl)-β-alanine ethyl ester hydrochloride (0.67 g) as a white solid.

IR (Nujol): 3400, 2000, 1715, 1605 cm$^{-1}$; NMR (DMSO-d$_6$, δ): 1.61 (3H, t, J=7.2 Hz), 2.25 (3H, s), 3.03–2.98 (2H, m), 4.08 (2H, d, J=7.2 Hz), 4.80–4.88 (1H, m), 6.60 (1H, s), 9.14 (2H, br); MASS (m/z): 199 (M$^+$ free+1).

PREPARATION 6

To a mixture of ethyl (R)-nipecotinate (1.86 g), 3-[1-(tert-butoxycarbonyl)-4-piperidyl]-(E)-acrylic acid (3.2 g) and 1-hydroxybenzotriazole (1.60 g) in dimethylformamide (20 ml) was added 1-ethyl-3-(3-dimethylaminopropyl) carbodiimide (2.16 ml) at 0° C. The reaction mixture was stirred overnight at room temperature, and then poured into water. The whole was extracted with ethyl acetate, washed with aqueous saturated NaHCO$_3$, water, and brine, dried over MgSO$_4$, and evaporated in vacuo, subsequently. The residue was purified by column chromatography on silica gel eluting with CHCl$_3$-MeOH (99:1) to give ethyl (R)-1-[3-(1-tert-butoxycarbonyl-4-piperidyl)-(E)-acryloyl]-3-piperidinecarboxylate as a colorless oil (4.46 g).

IR (Film): 3450, 2940, 2860, 1725, 1680, 1620 cm$^{-1}$; NMR (CDCl$_3$, δ): 1.27 (3H, t, J=7.1 Hz), 1.26–1.46 (2H, m), 1.46 (9H, s), 1.52–1.82 (8H, m), 2.02–2.14 (1H, m), 2.21–2.36 (2H, m), 2.44–2.56 (1H, m), 2.69–2.83 (2H, m), 3.02–3.10 (1H, m), 4.08–4.17 (2H, m), 4.15 (2H, q, J=7.1 Hz), 6.27 (1H, d, J=15.1 Hz), 6.81 (1H, dd, J=6.7 and 15.1 Hz).

PREPARATION 7

A solution of LiOH (0.32 g) in H$_2$O (20 ml) was added to a solution of ethyl (R)-1-[3-(1-tert-butoxycarbonyl-4-piperidyl)-(E)-acryloyl]-3-piperidinecarboxylate (4.46 g) in tetrahydrofuran (20 ml)-EtOH (20 ml) at 0° C. The reaction mixture was stirred for 3 hours at the same condition, and the solvent was evaporated in vacuo. The residue was resolved in ethyl acetate-water, and acidified with 10% aq. KHSO$_4$. The whole was washed with water, brine, dried over MgSO$_4$, and evaporated in vacuo, subsequently. The residue was recrystallized from diethyl ether to give (R)-1-[3-(1-tert-butoxycarbonyl-4-piperidyl)-(E)-acryloyl]-3-piperidinecarboxylic acid as a white solid (3.07 g).

mp: 128–129° C.; IR (Film): 1720, 1680, 1660 cm$^{-1}$; NMR (DMSO-d$_6$, δ): 1.08–1.31 (2H, m), 1.39 (9H, s), 1.65–1.70 (5H, m), 1.84–1.99 (1H, m), 2.24–2.41 (2H, m), 2.74–2.82 (2H, m), 3.04 (1H, m), 3.32–3.46 (2H, m), 3.85–3.98 (3H, m), 6.43 (1H, d, J=15.8 Hz), 6.60 (1H, d, J=5.4 and 15.8 Hz), 12.4 (1H, s); MASS (m/z): 367 (M$^+$+1).

PREPARATION 8

A mixture of 1-tert-butyldimethylsilyl-4(S)-ethynyl-2-azetidinone (3.0 g) and trimethylsilylazide (15 ml) was heated at 80° C. for 20 hours. The reaction mixture was allowed to room temperature and evaporated in vacuo. The residue was purified by column chromatography on silica gel eluting with n-hexane ethyl acetate=(1:1) to give 1-tert-butyldimethylsilyl-4(S)-(2H-1,2,3-triazol-4-yl)-2-azetidinone (0.3 g, 8.3%) as a pale yellow solid.

IR (Nujol): 3180, 3050, 1710 cm$^{-1}$; NMR (CDCl$_3$, δ): 0.35 (3H, s), 0.19 (3H, s), 0.85 (9H, s), 3.20 (1H, dd, J=2.9 and 15.5 Hz), 3.58 (1H, dd, J=5.7 and 15.5 Hz), 4.86 (1H, dd, J=2.9 and 5.7 Hz), 7.75 (1H, s); MASS (m/z): 253 (M$^+$).

PREPARATION 9

1-tert-Butyldimethylsilyl-4(S)-(2H-1,2,3-triazol-4-yl)-2-azetidinone (0.3 g) was added to 6N HCl/EtOH (10 ml). The mixture was stirred for 1 hour, and then evaporated in vacuo. The crystalline solid was washed with diethyl ether to give 3(S)-(2H-1,2,3-triazol-4-yl)-β-alanine ethyl ester hydrochloride (0.25 g, 94.4%) as a white solid.

NMR (CDCl$_3$, δ): 1.04 (3H, t, J=7.1 Hz), 3.11 (2H, d, J=7.0 Hz), 4.97 (1H, t, J=7.0 Hz), 7.93 (1H, s); MASS (m/z): 184 (M$^+$+1).

PREPARATION 10

To a solution of trimethylsulfoxonium iodide (1.16 g, 5.25 mmol) in dimethylsulfoxide (10 ml) was added sodium hydride (60% dispersion in oil, 210 mg, 5.25 mmol) under 0° C., and the solution was stirred at room temperature for 10 minutes. To the resulting mixture was added a solution of 3-(1-tert-butoxycarbonyl-4-piperidyl)-(E)-acrylic acid methyl ester (1.37 g, 5.09 mmol) was added dropwise under 0° C., and it was stirred for 1 hour at room temperature and for 2 hours at 50° C. After cooling to 0° C., saturated aqueous ammonium chloride was added to quench the reaction. The mixture was extracted with diethyl ether 50 ml×2), and the organic phase was washed with brine, dried over MgSO$_4$, filtered and evaporated in vacuo. The residue was purified by column chromatography (n-hexane/ethyl acetate=7/1) to give 2-(1-tert-butoxycarbonyl-4-piperidyl)-(1R*,2S*)-cyclopropane-1-carboxylic acid methyl ester.

IR (Neat): 1730, 1690 cm$^{-1}$; NMR (CDCl$_3$, δ): 0.70–1.00 (2H, m), 1.10–1.50 (5H, m), 1.45 (9H, s), 1.60–2.00 (2H, m), 2.50–2.75 (2H, m), 3.66 (3H, s), 3.90–4.20 (2H, m); MASS (m/z): 184 (M$^+$+1-Boc).

The following compounds [Preparations 11 to 21] were obtained according to a similar manner to that of Preparation 6.

PREPARATION 11

Ethyl (R)-1-[3-(1-tert-butoxycarbonyl-1,2,3,6-tetrahydro-4-pyridyl)-(E)-acryloyl]-3-piperidinecarboxylate IR (Film): 1730, 1690, 1640, 1620, 1600 cm$^{-1}$; NMR (CDCl$_3$, δ): 1.26 (3H, t, J=7.1 Hz), 1.47 (9H, s), 1.66–1.78 (2H, m), 2.02–2.17 (2H, m), 2.30 (2H, br), 2.42–2.56 (1H, br), 2.85–3.18 (2H, br), 3.54–3.59 (2H, m), 3.84–3.95 (2H, br), 4.07 (2H, br), 4.15 (2H, d, J=7.1 Hz), 6.01 (1H, br), 6.21–6.45 (1H, m), 7.28 (1H, d, J=15.0 Hz).

PREPARATION 12

Ethyl (R)-1-[3-(1-tert-butoxycarbonyl- 4-piperidyl)-(Z)-acryloyl]-3-piperidinecarboxylate IR (Film): 1720, 1690, 1630, 1615 cm$^{-1}$; NMR (CDCl$_3$, δ): 1.17–1.38 (2H, m), 1.26 (3H, t, J=7.2 Hz), 1.46 (9H, s), 1.65–1.77 (4H, m), 2.04–2.11 (1H, m), 2.42–2.52 (1H, m), 2.70–3.45 (5H, m), 3.76–3.91 (3H, m), 4.04–4.60 (5H, m), 3.94–4.24 (2H, m), 5.64–5.77 (1H, m), 5.96, 6.04 (total 1H, d, J=11.6 Hz).

PREPARATION 13

Ethyl (S)-1-[3-(1-tert-butoxycarbonyl-4-piperidyl)-(E)-acryloyl]-3-piperidinecarboxylate IR (Film): 2910, 1850, 1720, 1680, 1650, 1600 cm$^{-1}$; NMR (CDCl$_3$, δ): 1.26 (3H, t, J=7.1 Hz), 1.30–1.63 (3H, m), 1.46 (9H, s), 1.69–1.88 (4H, m), 2.03–2.14 (1H, m), 2.21–2.39 (1H, m), 2.42–2.54 (5H, m), 2.70–2.82 (2H, m), 3.03–3.14 (5H, m), 3.35–3.54 (1H, m), 3.83–3.95 (1H, m), 4.08–4.75 (5H, m), 6.30 (1H, d, J=15.2 Hz), 6.81 (1H, dd, J=15.2 and 6.7 Hz); MASS (m/z): 395 (M$^+$+1).

PREPARATION 14

Ethyl (R)-1-[3-(1-tert-butoxycarbonyl-3-azetidinyl)-(E)-acryloyl]-3-piperidinecarboxylate IR (Neat): 1700 cm$^{-1}$; NMR (CDCl$_3$, δ): 1.26 (3H, t, J=7.1 Hz), 1.43 (9H, 3), 1.50–2.20 (4H, m), 2.20–3.20 (3H, m), 3.20–3.60 (1H, m), 3.65–4.05 (1H, m), 4.05–4.25 (3H, m), 4.40–4.75 (2H, br), 6.20–6.45 (1H, m), 6.98 (1H, dd, J=15.0 and 8.2 Hz); MASS (m/z): 367 (M$^+$+1).

PREPARATION 15

Ethyl (R)-1-[4-(1-tert-butoxycarbonyl- 3-azetidinyl)-(E)-2-butenoyl]-3-piperidinecarboxylate IR (Neat): 1690, 1650, 1620 cm$^{-1}$; NMR (CDCl$_3$, δ): 1.27 (3H, t, J=7.1 Hz), 1.44 (9H, s), 1.45–1.95 (5H, m), 1.95–2.20 (1H, m), 2.35–2.75 (3H, m), 3.00–3.25 (1H, m), 3.35–4.25 (8H, m), 6.20–6.40 (1H, m), 6.67–6.82 (1H, m); MASS (m/z): 381 (M$^+$+1).

PREPARATION 16

Ethyl (R)-1-[(2-tert-butoxycarbonyl-1,2,3,4-tetrahydroisoquinolin-6-yl)carbonyl]-3-piperidinecarboxylate IR (Nujol): 1720, 1690, 1630 cm$^{-1}$; NMR (CDCl$_3$, δ): 1.20–1.30 (3H, m), 1.49 (9H, m), 1.60–1.90 (3H, m), 2.05–2.20 (1H, m), 2.35–2.70 (1H, m), 2.75–2.95 (2H, m), 2.95–3.45 (4H, m), 3.65 (2H, t, J=5.9 Hz), 4.05–4.25 (2H, m), 4.58 (2H, s), 7.10–7.27 (3H, m); MASS (m/z): 417 (M$^+$+1).

PREPARATION 17

Ethyl (R)-1-[3-(1-tert-butoxycarbonyl-4-piperidyl)-(E)-methacryloyl]-3-piperidinecarboxylate

PREPARATION 18

Ethyl (R)-1-[2-[1-tert-butoxycarbonyl-4-piperidyl]-(1R*,2S*)-cyclopropan-1-yl-carbonyl]-3-piperidinecarboxylate IR (Neat): 1730, 1680, 1630 cm$^{-1}$; NMR (CDCl$_3$, δ): 0.55–1.05 (2H, m), 1.05–1.35 (7H, m), 1.46 (9H, s), 1.50–1.95 (4H, m), 1.95–2.35 (1H, m), 2.35–3.65 (6H, m), 3.90–4.35 (6H, m), 4.45–4.85 (1H, m); MASS (m/z): 409 (M$^+$+1).

PREPARATION 19

Ethyl (R)-1-[3-(1-tert-butoxycarbonyl-4-piperidyl)-3-methyl-(E)-acryloyl]-3-piperidinecarboxylate IR (Neat): 1730, 1690, 1630 cm$^{-1}$; NMR (CDCl$_3$, δ): 1.25–1.60 (2H, m), 1.26 (3H, t, J=7.1 Hz), 1.46 (9H, s), 1.60–1.80 (4H, m), 1.83 (3H, s), 1.90–2.20 (3H, m), 2.30–2.55 (1H, m), 2.70 (2H, t, J=11.9 Hz), 2.80–3.40 (2H, m), 3.60–3.95 (1H, m), 4.00–4.35 (4H, m), 4.45–4.75 (1H, m), 5.78 (1H, d, J=13.6 Hz); MASS (m/z): 409 (M$^+$+1).

PREPARATION 20

Ethyl (R)-1-[4-(1-tert-butoxycarbonyl-3-piperidyl)-2-butenoyl]-3-piperidinecarboxylate IR (Neat): 1730, 1680 cm$^{-1}$; NMR (CDCl$_3$, δ): 0.95–3.30 (16H, m), 1.45 (9H, s), 3.30–4.25 (8H, m), 4.50–4.80 (1H, m), 6.15–6.45 (1H, m), 6.75–6.90 (1H, m); MASS (m/z): 409 (M$^+$+1).

PREPARATION 21

Ethyl (R)-1-[3-(1-tert-butoxycarbonyl-1,2,3,6-tetrahydro-4-pyridyl)propanoyl]-3-piperidinecarboxylate IR (Film): 1730, 1690, 1640 cm$^{-1}$; NMR (CDCl$_3$, δ): 1.15–1.31 (3H, t, J=7.0 Hz), 1.46 (9H, s), 1.67–1.77 (3H, m), 2.04–2.07 (3H, m), 2.33–2.50 (5H, m), 2.98–3.11 (2H, m), 3.36–3.51 (2H, m), 3.76–3.85 (3H, m), 4.02–4.21 (3H, m), 5.38 (1H, br);

The following compounds [Preparation 22 to 33] were obtained according to a similar manner to that of Preparation 7.

PREPARATION 22

(R)-1-[3-(1-tert-Butoxycarbonyl-1,2,3,6-tetrahydro-4-pyridyl)-(E)-acryloyl]-3-piperidinecarboxylic Acid IR (Film): 1730, 1690, 1640, 1620, 1600 cm$^{-1}$; NMR (CDCl$_3$, δ): 1.47 (9H, s), 1.78 (2H, br), 2.09 (1H, br), 2.29 (2H, br), 2.55 (1H, br), 3.20 (2H, br), 3.54–3.60 (2H, m), 3.95 (2H, br), 4.07–4.11 (2H, m), 6.01 (1H, br), 6.28 (1H, br), 7.28 (1H, d, J=15.0 Hz).

PREPARATION 23

(R)-1-[3-(1-tert-Butoxycarbonyl-4-piperidyl)-(Z)-acryloyl]-3-piperidinecarboxylic Acid

PREPARATION 24

(S)-1-[3-(1-tert-Butoxycarbonyl-4-piperidyl)-(E)-acryloyl]-3-piperidinecarboxylic Acid IR (Nujol): 1705, 1680, 1660 cm$^{-1}$; NMR (DMSO-d$_6$, δ): 1.08–1.31 (2H, m), 1.39 (9H, s), 1.39–1.74 (6H, m), 1.89–2.01 (1H, m), 2.24–2.44 (1H, m), 2.70–2.89 (2H, m), 2.97–3.12 (1H, m), 3.29–3.48 (1H, m), 3.80–4.01, 4.36–4.49 (total 4H, m), 6.43 (1H, d, J=15.5 Hz), 6.60 (1H, dd, J=15.5 and 5.5 Hz), 12.39 (1H, br); MASS (m/z): 367 (M$^+$+1).

PREPARATION 25

(R)-1-[3-(1-tert-Butoxycarbonyl-3-azetidinyl)-(E)-acryloyl]-3-piperidinecarboxylic Acid IR (Neat): 1700 cm$^{-1}$; NMR (CDCl$_3$, δ): 1.43 (9H, s), 1.45–2.20 (3H, m), 2.20–2.85 (3H, m), 2.85–3.50 (2H, m), 3.60–4.20 (6H, m), 5.40–6.10 (1H, br), 6.20–6.50 (1H, m), 6.80–7.10 (1H, m).

PREPARATION 26

(R)-1-[4-(1-tert-Butoxycarbonyl-3-azetidinyl)-(E)-2-enoyl]-3-piperidinecarboxylic Acid IR (Neat): 1710, 1690 cm$^{-1}$; NMR (CDCl$_3$, δ): 1.44 (9H, s), 1.45–2.20 (3H, m), 2.40–2.80 (4H, m), 2.90–3.95 (8H, m), 4.03 (2H, t, J=8.5 Hz), 6.15–6.50 (1H, m), 6.70–6.84 (1H, m); MASS (m/z): 353 (M$^+$+1).

PREPARATION 27

(R)-1-[(2-tert-Butoxycarbonyl-1,2,3,4-tetrahydrosoquinolin-6-yl)carbonyl]-3-piperidinecarboxylic Acid NMR (CDCl$_3$, δ): 1.35–1.90 (5H, m), 1.49 (9H, s), 2.00–2.25 (1H, m), 2.35–2.70 (1H, m), 2.84 (2H, t, J=5.8 Hz), 2.95–3.40 (2H, m), 3.65 (2H, t, J=5.8 Hz), 4.58 (2H, s), 5.10–5.80 (1H, br), 7.00–7.25.(3H, m); MASS (m/z): 389 (M$^+$+1).

PREPARATION 28

(R)-1-[3-(1-tert-Butoxycarbonyl-4-piperidyl)-(E)-methacryloyl]-3-piperidinecarboxylic Acid NMR (CDCl$_3$, δ): 1.15–1.45 (2H, m), 1.46 (9H, s), 1.50–1.95 (6H, m), 1.86 (3H, d, J=2.2 Hz), 2.00–2.10 (1H, m), 2.30–2.65 (2H, m), 2.65–2.95 (2H, m), 2.95–3.35 (2H, m), 3.80–4.25 (3H, m), 4.90–5.80 (1H, br), 5.34 (1H, d, J=7.7 Hz); MASS (m/z): 281 (M$^+$+1-Boc).

PREPARATION 29

2-(1-tert-Butoxycarbonyl-4-piperidyl)-(1R*,2S*)-cyclopropane-1-carboxylic Acid

IR (Neat): 1680 cm$^{-1}$; NMR (CDCl$_3$, δ): 0.75–1.00 (2H, m), 1.15–1.60 (5H, m), 1.46 (9H, s), 1.60–1.80 (2H, m), 2.50–2.75 (2H, m), 3.90–4.25 (2H, m); MASS (m/z): 170 (M$^+$+1-Boc).

PREPARATION 30

(R)-1-[2-(1-tert-Butoxycarbonyl-4-piperidyl)-(1R*,2S*)-cyclopropan-1-yl-carbonyl-3-piperidinecarboxylic Acid IR (Neat): 1670 cm$^{-1}$; NMR (CDCl$_3$, δ): 0.60–2.35 (11H, m), 1.45 (9H, s), 2.35–4.25 (10H, m), 6.15–7.20 (1H, br); MASS (m/z): 381 (M$^+$+1).

PREPARATION 31

(R)-1-[3-(1-tert-Butoxycarbonyl-4-piperidyl)-3-methyl-(E)-acryloyl]-3-piperidinecarboxylic Acid IR (Neat): 1730, 1690 cm$^{-1}$; NMR (CDCl$_3$, δ): 1.25–1.60 (2H, m), 1.46 (9H, s), 1.60–1.95 (4H, m), 1.83 (3H, s), 1.95–2.20 (2H, m), 2.35–2.60 (1H, m), 2.60–2.80 (2H, m), 2.90–3.25 (2H, m), 3.25–3.55 (1H, m), 3.65–4.35 (3H, m), 4.40–4.65 (1H, m), 5.78 (1H, d, J=13.9 Hz), 5.85–6.70 (1H, br); MASS (m/z): 381 (M$^+$+1).

PREPARATION 32

(R)-1-[4-(1-tert-Butoxycarbonyl-3-piperidyl)-2-butenoyl]-3-piperidinecarboxylic Acid NMR (CDCl$_3$, δ): 1.00–4.20 (21H, m), 1.45 (9H, s), 6.20–6.40 (1H, m), 6.65–6.88 (1H, m); MASS (m/z): 381 (M$^+$+1).

PREPARATION 33

(R)-1-[3-(1-tert-Butoxycarbonyl-1,2,3,6-tetrahydro-4-pyridyl)propanoyl]-3-piperidinecarboxylic Acid IR (Film): 1720, 1690 cm$^{-1}$;

The following compound was obtained according to a similar manner to that of Preparation 6.

PREPARATION 34

Methyl 2-[3-[1-(tert-butoxycarbonyl)-4-piperidyl ]-(E)-acryloyl]-1,2,3,4-tetrahydroisoquinoline-4-carboxylate NMR (CDCl$_3$, δ): 1.30–1.50 (2H, m), 1.46 (9H, s), 1.65–1.85 (2H, m), 2.20–2.50 (1H, m), 2.78 (2H, t-like), 3.50–4.00 (2H, m), 3.70 (3H, s), 4.00–4.30 (2H, m), 4.40–4.65 (2H, m), 5.00–5.25 (1H, m), 6.25–6.60 (1H, m), 6.88 (1H, dd, J=15.3 and 6.6 Hz), 7.10–7.40 (4H, m); MASS (m/z): 429 (M$^+$+1).

The following compound was obtained according to a similar manner to that of Preparation 7.

PREPARATION 35

2-[3-[1-(tert-Butoxycarbonyl)-4-piperidyl]-(E)-acryloyl]-1,2,3,4-tetrahydroisoquinoline-4-carboxylic Acid

EXAMPLE 1

To a mixture of (R)-1-[3-(1-tert-butoxycarbonyl-4-piperidyl)-(E)-acryloyl]-3-piperidinecarboxylic acid (1 g), 3(S)-ethynyl-β-alanine ethyl ester hydrochloride (0.48 g) and 1-hydroxybenzotriazole (0.37 g) in dimethylformamide (10 ml) was added 1-ethyl-3-(3-dimethylaminopropyl)carbodiimide (0.5 ml) at 0° C. The reaction mixture was stirred overnight at room temperature, and then poured into water. The whole was extracted with ethyl acetate, washed with aqueous saturated NaHCO$_3$, water, and brine, dried over MgSO$_4$, and evaporated in vacuo, subsequently. The residue was purified by column chromatography on silica gel eluting with CHCl$_3$-MeOH (99:1) to give N-[(R)-1-[3-(1-tert-butoxycarbonyl-4-piperidyl)-(E)-acryloyl]-3-piperidylcarbonyl]-3(S)-ethynyl-β-alanine ethyl ester as a pale yellow oil (1.34 g).

IR (Film): 3250, 2910, 2850, 1720, 1650, 1600 cm$^{-1}$; NMR (CDCl$_3$, δ): 1.28 (3H, t, J=7.1 Hz), 1.25–1.57 (2H, m), 1.46 (9H, s), 1.70–1.80 (3H, m), 1.92–2.10 (2H, m), 2.24–2.40 (2H, m), 2.28 (1H, d, J=2.3 Hz), 2.70–2.85 (4H, m), 3.22–3.41 (2H, m), 3.65–3.80 (1H, m), 4.07–4.25 (4H, m), 4.18 (2H, q, J=7.1 Hz), 5.05–5.17 (1H, m), 6.22 (1H, d, J=15.1 Hz), 6.83 (1H, dd, J=7.1 and 15.1 Hz), 7.02–7.18 (1H, m); MASS (m/z): 490 (M$^+$+1).

The following compounds [Examples 2 to 7] were obtained according to a similar manner to that of Example

EXAMPLE 2

N-[(R)-1-[3-(1-tert-butoxycarbonyl-4-piperidyl)propionyl]-3-piperidylcarbonyl]-3(S)-(3-methyl-5-isoxazolyl)-β-alanine Ethyl Ester IR (Film): 3360, 1730, 1640 cm$^{-1}$; NMR (CDCl$_3$, δ): 1.09–1.25 (3H, m), 1.26 (3H, t, J=7.2 Hz), 1.45 (9H, s), 1.53–1.71 (6H, m), 1.91–1.95 (2H, m), 2.26 (3H, s), 2.39–2.46 (3H, m), 2.61–2.72 (2H, m), 2.87–2.93 (1H, m), 3.10 (1H, br), 3.36–3.50 (2H, m), 3.78 (1H, br), 3.96–4.07

(3H, m), 4.12 (2H, d, J=7.2 Hz), 5.57–5.78 (1H, m), 5.99 (1H, s); MASS (m/z): 549 (M+ free+1).

EXAMPLE 3

N-[(R)-1-[3-(1-tert-butoxycarbonyl-4-piperidyl)-(E)-acryloyl]-3-piperidylcarbonyl]-3-phenyl-β-alanine Methyl Ester IR (Film): 3000, 2930, 2860, 1740, 1670, 1650, 1600 cm$^{-1}$; NMR (CDCl$_3$, δ): 1.24–1.56 (5H, m), 1.46 (9H, s), 1.68–1.90 (4H, m), 2.03–2.51 (3H, m), 2.69–2.90 (4H, m), 3.40–3.60 (1H, m), 3.60, 3.63 (total 3H, s), 3.70–3.88 (1H, m), 4.06–4.20 (2H, m), 5.37–5.47 (1H, m), 6.15–6.28 (1H, m), 6.78 (1H, dd, J=15.2 and 6.5 Hz), 7.26–7.51 (6H, m); MASS (m/z): 528 (M$^+$+1).

EXAMPLE 4

N-[(R)-1-[3-(1-tert-butoxycarbonyl-4-piperidyl)-(E)-acryloyl]-3-piperidylcarbonyl]-2(S)-(acetylamino)-β-alanine Ethyl Ester IR (Film): 2975, 2930, 2860 cm$^{-1}$; NMR (CDCl$_3$, δ): 1.28 (3H, t, J=7.1 Hz), 1.25–1.60 (6H, m), 1.46 (9H, s), 1.69–1.81 (2H, m), 2.07 (3H, s), 2.21–2.52 (3H, m), 2.70–2.84 (2H, m), 3.33–3.73 (4H, m), 3.95–4.27 (6H, m), 4.64–4.72 (1H, m), 6.27 (1H, d, J=15.3 Hz), 6.82 (1H, dd, J=15.3 and 6.7 Hz), 7.01–7.27 (1H, m); MASS (m/z): 523 (M$^+$+1).

EXAMPLE 5

N-[(R)-1-[3-(1-tert-butoxycarbonyl-4-piperidyl)-(E)-acryloyl]-3-piperidylcarbonyl]-3(R)-methyl-β-alanine Methyl Ester IR (Film): 3060, 2970, 2930, 2850, 1725, 1645, 1600 cm$^{-1}$; NMR (CDCl$_3$, δ): 1.22 (3H, t, J=6.8 Hz), 1.28–1.60 (4H, m), 1.46 (9H, s), 1.68–1.80 (3H, m), 1.86–2.03 (2H, m), 2.23–2.40 (3H, m), 2.50 (2H, d, J=5.5 Hz), 2.70–2.84 (2H, m), 3.32–3.56 (2H, m), 3.68 (3H, s), 4.00–4.19 (3H, m), 4.30–4.42 (1H, m), 6.25 (1H, d, J=15.2 Hz), 6.82 (1H, dd, J=6.7, and 15.2 Hz); MASS (m/z): 466 (M$^+$+1).

EXAMPLE 6

N-[(R)-1-[3-(1-tert-butoxycarbonyl-4-piperidyl)-(E)-acryloyl]-3-piperidylcarbonyl]-3(R)-phenethyl-β-alanine Ethyl Ester IR (Film): 2960, 2920, 2850, 1720, 1670, 1650 cm$^{-1}$; NMR (CDCl$_3$, δ): 1.25 (3H, t, J=7.1 Hz), 1.30–1.59 (2H, m), 1.46 (9H, s), 1.66–2.16 (8H, m), 2.22–2.40 (2H, m), 2.48–2.83 (6H, m), 3.24–3.68 (3H, m), 4.01–4.37 (6H, m), 6.23 (1H, d, J=15.2 Hz), 6.81 (1H, dd, J=6.6 and 15.2 Hz), 7.13–7.32 (6H, m); MASS (m/z): 570 (M$^+$+1).

EXAMPLE 7

N-[(R)-1-[3-(1-tert-butoxycarbonyl-4-piperidyl)-(E)-acryloyl]-3-piperidylcarbonyl]-2(S)-benzoylamino-β-alanine Ethyl Ester IR (Film): 2980, 2930, 2860, 1740, 1670, 1655, 1600 cm$^{-1}$; NMR (CDCl$_3$, δ): 1.11–1.33 (2H, m), 1.30 (3H, t, J=7.1 Hz), 1.46 (9H, s), 1.46–1.83 (6H, m), 2.09–2.55 (3H, m), 2.63–2.78 (2H, m), 3.26–3.72 (4H, m), 4.00–4.24 (5H, m), 4.82–4.90 (1H, m), 6.18 (1H, d, J=15.1 Hz), 6.67 (1H, dd, J=6.3 and 15.1 Hz), 7.33–7.65 (4H, m), 7.79–8.00 (3H, m); MASS (m/z): 585 (M$^+$+1).

EXAMPLE 8

A solution of LiOH (79 mg) in H$_2$O (10 ml) was added to a solution of N-[(R)-1-[3-(1-tert-butoxycarbonyl-4-piperidyl)-(E)-acryloyl]-3-piperidylcarbonyl]- 3(S)-ethynyl-β-alanine ethyl ester (1.34 g) in tetrahydrofuran (10 ml)-EtOH (10 ml) at 0° C. The reaction mixture was stirred for 3 hours at the same condition, and the solvent was evaporated in vacuo. The residue was resolved in ethyl acetate-water, and acidified with 10% aq. KHSO$_4$. The whole was washed with water, brine, dried over MgSO$_4$, and evaporated in vacuo to give N-[(R)-1-[3-(1-tert-butoxycarbonyl-4-piperidyl)-(E)-acryloyl]-3-piperidylcarbonyl]-3(S)-ethynyl-β-alanine (1.23 g).

IR (Film): 3270, 2920, 2850, 1720, 1650, 1600 cm$^{-1}$; NMR (DMSO-d$_6$, δ): 1.12–1.35 (3H, m), 1.39 (9H, s), 1.50–1.80 (5H, m), 2.14–2.38 (2H, m), 2.56–3.20 (6H, m), 3.90–4.01 (4H, m), 4.17–4.38 (1H, m), 4.77–4.87 (1H, m), 6.42 (1H, d, J=15.1 Hz), 6.60 (1H, dd, J=6.4 and 15.1 Hz), 8.43 (1H, d, J=8.2 Hz), 12.4 (1H, br); MASS (m/z): 462 (M$^+$+1).

The following compounds [Examples 9 to 13] were obtained according to a similar manner to that of Example 8.

EXAMPLE 9

N-[(R)-1-[3-(1-tert-butoxycarbonyl-4-piperidyl)-(E)-acryloyl]-3-piperidylcarbonyl]-2(S)-acetylamino-β-alanine IR (Film): 2930, 1720, 1650 cm$^{-1}$; NMR (DMSO-d$_6$, δ): 1.11–1.32 (3H, m), 1.39 (9H, m), 1.39–1.99 (7H, m), 1.91 (3H, m), 2.12–2.40 (1H, m), 2.51–2.86 (3H, m), 3.32–3.57 (2H, m), 3.89–4.06 (3H, m), 4.23–4.45 (2H, m), 6.39–6.67 (2H, m), 7.95–8.12 (2H, m); MASS (m/z): 495 (M$^+$+1).

EXAMPLE 10

N-[(R)-1-[3-(1-tert-butoxycarbonyl-4-piperidyl)-(E)-acryloyl]-3-piperidylcarbonyl]-3(R)-methyl-β-alanine IR (Film): 2950, 2850, 1705, 1650, 1600 cm$^{-1}$; NMR (DMSO-d$_6$, δ): 1.06 (3H, d, J=6.6 Hz), 1.17–1.31 (2H, m), 1.39 (9H, s), 1.51–1.85 (5H, m), 2.07–2.40 (4H, m), 2.58–3.13 (5H, m), 3.91–4.40 (5H, m), 6.42 (1H, d, J=15.1 Hz), 6.60 (1H, dd, J=6.4 and 15.1 Hz), 7.83 (1H, d, J=7.9 Hz), 12.10–12.20 (1H, br); MASS (m/z): 452 (M$^+$+1).

EXAMPLE 11

N-[(R)-1-[3-(1-tert-butoxycarbonyl-4-piperidyl)-(E)-acryloyl]-3-piperidylcarbonyl]-3(R)-phenethyl-β-alanine IR (Film): 2920, 2850, 1710, 1645 cm$^{-1}$; NMR (DMSO-d$_6$, δ): 1.11–1.32 (4H, m), 1.39 (9H, s), 1.60–1.89 (6H, m), 2.15–2.35 (2H, m), 2.38 (2H, d, J=6.8 Hz), 2.55–3.21 (6H, m), 3.89–4.03 (4H, m), 4.20–4.40 (1H, m), 6.43 (1H, d, J=15.1 Hz), 6.61 (1H, dd, J=6.3 and 15.1 Hz), 7.15–7.30 (5H, m), 7.87 (1H, d, J=8.4 Hz), 12.10 (1H, s); MASS (m/z): 542 (M$^+$+1).

EXAMPLE 12

N-[(R)-1-[3-(1-tert-butoxycarbonyl-4-piperidyl)-(E)-acryloyl]-3-piperidylcarbonyl]-2(S)-benzoylamino-β-alanine IR (Film): 2930, 1725, 1635, 1600 cm$^{-1}$; NMR (DMSO-d$_6$, δ): 1.13–1.30 (2H, m), 1.39 (9H, s), 1.49–1.86 (6H, m), 2.16–2.36 (2H, m), 2.60–3.17 (4H, m), 3.38–3.69 (2H, m), 3.87–4.01 (3H, m), 4.19–4.59 (2H, m), 6.33–6.44 (1H, m), 6.59 (1H, dd, J=6.4 and 15.0 Hz), 7.45–7.56 (3H, m), 7.83–7.87 (2H, m), 8.13–8.22 (1H, m), 8.58–8.64 (1H, m); MASS (m/z): 557 (M$^+$+1).

EXAMPLE 13

N-[(R)-1-[3-(1-tert-butoxycarbonyl-4-piperidyl)-(E)-acryloyl]-3-piperidylcarbonyl]-3-phenyl-β-alanine IR (Film): 3000, 2960, 2930, 2855, 1715, 1650 cm$^{-1}$; NMR (DMSO-d$_6$, δ): 1.09–1.39 (2H, m), 1.39 (9H, s), 1.48–1.91 (6H, m), 2.14–2.37 (2H, m), 2.57–2.83 (6H, m), 3.87–4.01 (3H, m), 4.15–4.43 (1H, m), 5.18 (1H, q, J=7.6 Hz), 6.34–6.66 (2H, m), 7.19–7.31 (5H, m), 8.41 (1H, d, J=8.4 Hz), 12.17–12.26 (1H, br); MASS (m/z): 514 (M$^+$+1).

EXAMPLE 14

To a mixture of N-[(R)-1-[3-(1-tert-butoxycarbonyl-4-piperidyl)propionyl]-3-piperidylcarbonyl]-3(S)-ethynyl-β-alanine (0.5 g), 4-methyl-1-pentanol 0.15 ml) and N,N-dimethylaminopyridine (13 mg) in dichloromethane (5 ml) was added 1-ethyl-3-(3-dimethylaminopropyl)carbodiimide hydrochloride (0.23 g) at 0° C. After stirring at an ambient temperature overnight, the solution was evaporated in vacuo. The residue was poured into water and extracted with ethyl acetate. The extract was washed with saturated aqueous sodium hydrogen carbonate, water and brine, dried over magnesium sulfate, and evaporated in vacuo, subsequently. The residue was purified by column chromatography on silica gel eluting with CHCl$_3$:MeOH (100:1) to give N-[(R)-1-[3-(1-tert-butoxycarbonyl-4-piperidyl)propionyl]-3-piperidylcarbonyl]-3(S)-ethynyl-β-alanine isohexyl ester (0.59 g) as an oil.

IR (Film): 2930, 2860, 1735, 1680, 1630 cm$^{-1}$; NMR (CDCl$_3$, δ): 0.89 (6H, d, J=6.6 Hz), 0.97–1.29 (5H, m), 1.45 (9H, s), 1.50–2.15 (11H, m), 2.27 (1H, d, J=2.2 Hz), 2.36 (3H, t, J=7.8 Hz), 2.62–2.72 (5H, m), 3.29–3.40 (2H, m), 3.51 (1H, m), 4.10 (2H, t, J=6.8 Hz), 4.03–4.20 (2H, m), 5.04–5.16 (1H, m), 6.77 and 7.01 (total 1H, d, J=8.6 Hz); MASS (m/z): 548 (M$^+$+1).

The following compounds [Examples 15 to 18] were obtained according to a similar manner to that of Example 4.

EXAMPLE 15

N-[(R)-1-[3-(1-tert-butoxycarbonyl-4-piperidyl)-propionyl]-3-piperidylcarbonyl]-3(S)-ethynyl-β-alanine Isopentyl Ester IR (Film): 3000, 2940, 2860, 1730, 1660, 1620 cm$^{-1}$; NMR (CDCl$_3$, δ): 0.93 (6H, d, J=6.5 Hz), 1.02–1.21 (2H, m), 1.45 (9H, s), 1.49–1.72 (9H, m), 1.91–2.12 (2H, m), 2.27 (1H, d, J=2.2 Hz), 2.32–2.40 (3H, m), 2.60–2.77 (4H, m), 3.20–3.65 (3H, m), 4.04–4.11 (4H, m), 4.15 (2H, t, J=6.7 Hz), 5.03–5.16 (1H, m), 6.71, 7.01 (total 1H, d, J=8.4 Hz); MASS (m/z): 534 (M$^+$+1).

EXAMPLE 16

N-[(R)-1-[3-(1-tert-butoxycarbonyl-4-piperidyl)-propionyl]-3-piperidylcarbonyl]-3(S)-ethynyl-β-alanine Phenethyl Ester IR (Film): 2920, 2850, 1725, 1660, 1630 cm$^{-1}$; NMR (CDCl$_3$, δ): 1.01–1.20 (2H, m), 1.36–2.00 (14H, m), 1.57 (9H, s), 2.25 (1H, d, J=2.2 Hz), 2.31–2.41 (2H, m), 2.59–2.75 (5H, m), 2.97 (2H, t, J=6.8 Hz), 4.02–4.14 (2H, m), 4.29–4.40 (2H, m), 7.17–7.32 (6H, m); MASS (m/z): 468 (M$^+$-Boc+1).

EXAMPLE 17

N-[(R)-1-[3-(1-tert-butoxycarbonyl- 4-piperidyl)-propionyl]-3-piperidylcarbonyl]-3(S)-ethynyl-β-alanine Phenyl Ester IR (Film): 3000, 2930, 2855, 1750, 1660, 1620 cm$^{-1}$; NMR (CDCl$_3$, δ): 0.97–1.19 (2H, m), 1.45 (9H, s), 1.31–2.13 (1H, m), 2.29–2.40 (3H, m), 2.36 (1H, d, J=2.0 Hz), 2.68–2.73 (2H, m), 2.92–3.02 (2H, m), 3.24–3.72 (2H, m), 3.82–3.91 (1H, m), 4.02–4.12 (2H, m), 5.20–5.31 (1H, m), 7.12 (2H, d, J=8.1 Hz), 7.18–7.26 (1H, m), 7.35–7.42 (2H, m); MASS (m/z): 540 (M$^+$+1).

EXAMPLE 18

N-[(R)-1-[3-(1-tert-butoxycarbonyl-4-piperidyl)-propionyl]-3-piperidylcarbonyl]-3(S)-ethynyl-β-alanine 5-Indanyl Ester IR (Film): 2930, 2850, 1750, 1660, 1640 cm$^{-1}$; NMR (CDCl$_3$, δ): 0.97–1.18 (2H, m), 1.45 (9H, s), 1.45–1.94 (11H, m), 2.09 (2H, d, J=7.4 Hz), 2.30–2.37 (3H, m), 2.36 (1H, d, J=2.3 Hz), 2.59–2.72 (2H, m), 2.84–2.94 (6H, m), 3.23–3.69 (2H, m), 3.86–3.95 (1H, m), 4.01–4.11 (2H, m), 5.19–5.31 (1H, m), 6.82–6.87 (1H, m), 6.95 (1H, s), 7.19 (1H, d, J=8.0 Hz); MASS (m/z): 580 (M$^+$+1).

EXAMPLE 19

To a solution of N-[(R)-1-[3-(1-tert-butoxycarbonyl-4-piperidyl)-(E)-acryloyl]-3-piperidylcarbonyl]-3(R)-methyl-β-alanine (0.97 g) in ethyl acetate (10 ml) was added 4N HCl in ethyl acetate (5.37 ml) at room temperature, and the reaction mixture was stirred for 2 hours. The resulting precipitates were collected by filtration to give N-[(R)-1-[3-(1-tert-butoxycarbonyl-4-piperidyl)-(E)-acryloyl]-3-piperidylcarbonyl]- 3(R)-methyl-β-alanine hydrochloride (0.83 g).

IR (KBr pellet): 2945, 2870, 1726, 1657 cm$^{-1}$; NMR (DMSO-d$_6$, δ): 1.06 (3H, d, J=6.5 Hz), 1.21–1.39 (1H, m), 1.47–1.91 (7H, m), 2.10–2.48 (4H, m), 2.58–3.14 (4H, m), 3.20–3.29 (2H, m), 3.87–4.12 (2H, m), 4.15–4.42 (1H, m), 6.45 (1H, d, J=15.2 Hz), 6.58 (1H, dd, J=5.4 and 15.2 Hz), 7.86–7.95 (1H, m), 8.84–8.98 (1H, br), 9.10–9.21 (1H, br); MASS (m/z): 352 (M$^+$ free+1).

EXAMPLE 20

To a solution of N-[(R)-1-[3-(1-tert-butoxycarbonyl-4-piperidyl)-(E)-acryloyl]-3-piperidylcarbonyl]-3(S)-ethynyl-β-alanine (1.23 g) in ethyl acetate (12 ml) was added 4N HCl in ethyl acetate (6.66 ml) at room temperature, and the reaction mixture was stirred for 2 hours. The precipitates were filtered, washed with diethyl ether and purified by preparative HPLC eluting with 0.1% trifluoroacetic acid-CH$_3$CN (9:1), then the fractions containing the object compound were concentrated in vacuo. The residue was resolved in water, neutralized with 1N aq. NaOH, desalted by using the resin of HP-20 eluting with isopropanol-H$_2$O (1:1), freeze-dried to give N-[(R)-1-[3-(4-piperidyl)-(E)-acryloyl]-3-piperidylcarbonyl]-3(S)-ethynyl-β-alanine as a white powder (0.7 g).

IR (Film): 3200, 1660, 1580 cm$^{-1}$; NMR (DMSO-d$_6$, δ): 1.19–1.41 (2H, m), 1.59–1.88 (5H, m), 2.14–2.32 (4H, m), 2.51–2.76 (4H, m), 2.89–3.17 (4H, m), 3.89–4.42 (2H, m), 4.60–4.71 (1H, m), 6.36 (1H, d, J=15.1 Hz), 6.57 (1H, dd, J=6.4 and 15.1 Hz), 8.85 (1H, br); MASS (m/z): 362 (M$^+$+1). Elemental Analysis Calcd. for $C_{19}H_{27}N_3O_4 \cdot 1.1H_2O$: C, 59.86, H, 7.72, N, 11.02; Found: C, 59.70, H, 7.63, N, 10.91.

The following compounds [Examples 21 and 22] were obtained according to a similar manner to that of Example 20.

EXAMPLE 21

N-[(R)-1-[3-(4-Piperidyl)propionyl]-3-piperidylcarbonyl]-3(S)-ethynyl-β-alanine Isohexyl Ester IR (KBr pellet): 2953, 2936, 2868, 1736, 1657, 1650, 1620 cm$^{-1}$; NMR (DMSO-d$_6$, δ): 0.86 (6H, d, J=6.6 Hz), 0.97–1.64 (18H, m), 2.24–2.69 (6H, m), 2.88–3.12 (2H, m), 3.20–3.28 (1H, m), 3.78–3.83 (2H, m), 4.01 (2H, t, J=6.6 Hz), 4.11–4.35 (1H, m), 4.80–4.92 (1H, m), 8.40–8.49 (1H, m); MASS (m/z): 448 (M$^+$+1). Elemental Analysis Calcd. for $C_{25}H_{41}N_3O_4 \cdot H_2O$: C, 64.49, H, 9.31, N, 9.02; Found: C, 64.52, H, 9.32, N, 9.04.

EXAMPLE 22

N-[(R)-1-[3-(4-Piperidyl)propionyl]-3-piperidylcarbonyl]-3(S)-ethynyl-β-alanine Isopentyl Ester IR (KBr pellet): 3037, 2953, 2934, 2868, 1736, 1641, 1626 cm$^{-1}$; NMR (DMSO-d$_6$, δ): 0.88 (6H, d, J=6.5 Hz), 0.97–1.77 (15H, m), 2.14–2.68 (6H, m), 2.87–3.12 (3H, m), 3.20–3.24 (1H, m), 3.68–3.84 (2H, m), 4.06 (2H, t, J=6.7 Hz), 4.13–4.34 (2H, m), 4.78–4.92 (1H, m), 8.40–8.51 (1H, m); MASS (m/z): 434 (M$^+$+1).

EXAMPLE 23

To a solution of N-[(R)-(-E3-(1-tert-butoxycarbonyl-4-piperidyl)propionyl]-3-piperidylcarbonyl]-3(S)-ethynyl-β-alanine phenethyl ester (0.53 g) in ethyl acetate (5 ml) was added 4N HCl in ethyl acetate (2.33 ml) at room temperature, and the reaction mixture was stirred for 2 hours. The resulting precipitates were collected by filtration to give N-[(R)-1-[3-(4-piperidyl)propionyl]-3-piperidylcarbonyl]-3(S)-ethynyl-β-alanine phenethyl ester hydrochloride (0.46 g).

IR (KBr pellet): 3028, 2945, 2864, 2804, 1736, 1651 cm$^{-1}$; NMR (DMSO-d$_6$, δ): 1.21–1.75 (11H, m), 2.30–2.35 (2H, m), 2.61–3.10 (8H, m), 2.88 (3H, t, J=6.8 Hz), 3.17–3.29 (2H, m), 3.66–3.84 (1H, m), 4.24 (2H, d, J=7.0 Hz), 4.69–4.92 (1H, m), 7.20–7.35 (5H, m), 8.45–8.55 (1H, m), 8.46–8.65 (9H, br), 8.81–8.93 ((H, br); MASS (m/z): 468 (M$^+$ free+1).

The following compounds [Examples 24 to 29] were obtained according to a similar manner to that of Example 23.

EXAMPLE 24

N-[(R)-1-[3-(4-Piperidyl)-(E)-acryloyl]-3-piperidylcarbonyl]-3-phenyl-β-alanine Hydrochloride IR (Nujol): 1725, 1645 cm$^{-1}$; NMR (DMSO-d$_6$, δ): 1.16–1.91 (7H, m), 2.20–2.50 (4H, m), 2.60–3.00 (5H, n), 3.19–3.31 (3H, m), 4.15–4.46 (1H, m), 5.18 (1H, q, J=7.7 Hz), 6.44 (1H, d, J=15.3 Hz), 6.59 (pH, dd, J=15.3 and 5.2 Hz), 7.19–7.32 (5H, m), 8.47–8.60 (1H, m), 8.91–9.05 (1H, br), 9.18–9.30 (1H, br); MASS (m/z): 414 (M$^+$ free+1).

EXAMPLE 25

N-[(R)-1-[3-(4-Piperidyl)-(E)-acryloyl]-3-piperidylcarbonyl]-3(R)-phenethyl-β-alanine Hydrochloride IR (KBr pellet): 3061, 3026, 2949, 2860, 1724, 1653 cm$^{-1}$; NMR (DMSO-d$_6$, δ): 1.26–1.42 (1H, m), 1.49–1.85 (9H, m), 2.15–3.05 (1H, m), 3.18–3.31 (2H, m), 3.89–4.08 (2H, m), 4.20–4.42 (1H, m), 6.46 (1H, d, J=15.2 Hz), 6.59 (1H, dd, J=5.3 and 15.2 Hz), 7.16–7.30 (5H, m), 7.89–8.00 (2H, m), 8.88–9.00 (2H, br), 9.15–9.26 (1H, br); MASS (m/z): 442 (M$^+$ free+1).; [α]=-28.8° (C=1.0, MeOH); Elemental Analysis Calcd. for $C_{25}H_{35}N_3O_4 \cdot HCl \cdot 3.5H_2O$: C, 56.50, H, 8.01, N, 7.77; Found: C, 56.56, H, 7.77, N, 7.57.

EXAMPLE 26

N-[(R)-1-[3-(4-Piperidyl)-(E)-acryloyl]-3-piperidylcarbonyl]-2(S)-acetylamino-β-alanine Hydrochloride IR (KBr pellet): 307 6, 2953, 2864, 1728, 1657 cm$^{-1}$; NMR (DMSO-d$_6$, δ): 1.21–1.99 (10H, m), 1.85 (3H, s), 2.11–2.51 (2H, m), 2.57–3.11 (2H, m), 3.18–3.32 (2H, m), 3.35–3.48 (1H, m), 3.90–4.07 (1H, m), 4.17–4.45 (3H, m), 6.40–6.65 (2H, m), 8.07–8.27 (2H, m), 8.73–8.89 (1H, br), 9.00–9.13 (1H, br); MASS (m/z): 395 (M$^+$ free+1).; [α]=-29.2° (C=1.0, MeOH).

EXAMPLE 27

N-[(R)-1-[3-(4-Piperidyl)-(E)-acryloyl]-3-piperidylcarbonyl]-2(S)-benzoylamino-β-alanine Hydrochloride IR (KBr pellet): 2970, 2868, 1728, 1655, 1603 cm$^{-1}$; NMR (DMSO-d$_6$, δ): 1.14–1.99 (9H, m), 2.14–2.50 (2H, m), 2.57–3.11 (3H, m), 3.17–3.26 (2H, m), 3.37–3.50 (2H, m), 3.86–4.57 (3H, m), 6.43 (1H, d, J=15.4 Hz), 6.57 (1H, dd, J=15.4 and 5.5 Hz), 7.45–7.56 (3H, m), 7.89 (2H, d, J=6.6 Hz), 8.21–8.37 (1H, m), 8.62–8.86 (2H, m), 9.00–9.12 (1H, br); MASS (m/z): 457 (M$^+$ free+1).; [α]=-45.3° (C=1.0, MeOH).

EXAMPLE 28

N-[(R)-1-[3-(4-Piperidyl)propionyl]-3-piperidylcarbonyl]-3(S)-ethynyl-β-alanine Phenyl Ester IR (KBr pellet): 3043, 2953, 2862, 1755, 1653, 1616 cm$^{-1}$; NMR (DMSO-d$_6$, δ): 1.21–1.91 (12H, m), 2.06–2.38 (2H, m), 2.55–3.11 (7H, m), 3.13–3.28 (2H, m), 3.35–3.39 (1H, m), 3.67–3.85 (1H, m), 4.95–5.08 (1H, m), 7.11–7.44 (5H, m), 8.69 (1H, dd, J=16.1 and 8.3 Hz), 8.59–8.73 (1H, br), 8.88–9.00 (1H, br); MASS (m/z): 440 (M$^+$ free+1).

EXAMPLE 29

N-[(R)-1-[3-(4-Piperidyl)propionyl]-3-piperidylcarbonyl]-3(S)-ethynyl-β-alanine 5-indanyl Ester IR (KBr pellet): 2945, 2862, 2812, 1755, 1653, 1616 cm$^{-1}$; NMR (DMSO-d$_6$, δ): 1.22–1.86 (9H, m), 1.98–2.22

(2H, m), 2.27–2.40 (2H, m), 2.59–2.85 (11H, m), 3.15–3.26 (2H, m), 3.35–3.40 (1H, m), 3.69–3.85 (1H, m), 4.10–4.37 (1H, m), 4.92–5.04 (1H, m), 6.80–6.85 (2H, m), 6.94 (1H, s) 7.23 (2H, d, J=7.9 Hz), 8.40–8.52 (1H, m), 8.60–8.68 (1H, m), 8.63–8.80 (1H, br); MASS (m/z): 480 (M$^+$ free+1).

EXAMPLE 30

To the solution of N-[(R)-1-[3-(1-tert-butoxycarbonyl-4-piperidyl)propionyl]-3-piperidylcarbonyl]-3(S)-(3-methyl-5-isoxazolyl)-β-alanine ethyl ester (0.8 g) in MeOH (10 ml) was added 1N aqueous NaOH (2.3 ml) at 0° C. The reaction mixture was stirred at room temperature for 2 hours, and then the solvent was removed in vacuo. The residue was dissolved in ethyl acetate-water, and acidified with 10% aqueous KHSO$_4$. The organic layer was separated and evaporated in vacuo. The residue was dissolved in ethyl acetate (8 ml), and then a solution of 4N HCl in ethyl acetate (4 ml) was added. The whole was stirred at room temperature for 2 hours, and then the solvent was removed in vacuo. The residue was powdered from diethyl ether to give N-[(R)-1-[3-(4-piperidyl)propionyl]-3-piperidylcarbonyl]-3(S)-(3-methyl-5-isoxazolyl)-β-alanine hydrochloride (0.46 g) as a white solid.

IR (KBr pellet): 3446, 2931, 1734, 1652, 1608 cm$^{-1}$; NMR (D$_2$O, δ): 1.35–1.78 (8H, m), 1.93–2.00 (3H, s), 2.26 (3H, s), 2.45–2.53 (3H, m), 2.80–3.25 (6H, m), 3.39–3.45 (2H, m), 3.77–3.83 (1H, m), 4.08–4.22 (1H, m), 5.44–5.51 (1H, m), 6.24 (1H, d, J=2.2 Hz); MASS (m/z): 421 (M$^+$ free+1).

EXAMPLE 31

To a mixture of (R)-1-[3-(1-tert-butoxycarbonyl-4-piperidyl)-(E)-acryloyl]-3-piperidinecarboxylic acid (2 g) and β-alanine ethyl ester hydrochloride (0.84 g) and 1-hydroxybenzotriazole (0.74 g) in dimethylformamide (20 ml) was added 1-ethyl-3-(3-dimethylaminopropyl) carbodiimide (1 ml) at 0° C. The reaction mixture was stirred overnight at room temperature, and then poured into water. The whole was extracted with ethyl acetate, washed with aqueous saturated NaHCO$_3$, water, and brine, dried over MgSO$_4$, and evaporated in vacuo, subsequently. The residue was purified by column chromatography on silica gel eluting with CHCl$_3$-MeOH (99:1) to give N-[(R)-1-[3-(1-tert-butoxycarbonyl-4-piperidyl)-(E)-acryloyl]-3-piperidylcarbonyl]-β-alanine ethyl ester as a colorless oil (2.54 g).

IR (Film): 2960, 2930, 2850, 1725, 1650, 1600 cm$^{-1}$; NMR (CDCl$_3$, δ): 1.27 (3H, t, J=7.1 Hz), 1.31–1.40 (2H, m), 1.46 (9H, S), 1.63–1.78 (2H, m), 1.69–1.97 (6H, m), 2.20–2.37 (2H, m), 2.52 (2H, t, J=6.1 Hz), 2.69–2.83 (2H, m), 3.28 (1H, dd, J=13.5 and 9.5 Hz), 3.47–3.56 (2H, m), 4.07–4.17 (3H, m), 4.16 (2H, q, J=7.1 Hz), 6.23 (1H, d, J=15.1 Hz), 6.45–6.64 (1H, m), 6.81 (1H, dd, J=15.1 and 6.7 Hz); MASS (m/z): 466 (M$^+$+1).

EXAMPLE 32

A solution of LiOH (0.18 g) in water (10 ml) was added to a solution of N-[(R)-1-[3-(1-tert-butoxycarbonyl-4-piperidyl)-(E)-acryloyl]-3-piperidylcarbonyl]-β-alanine ethyl ester (1.74 g) in the mixture of tetrahydrofuran (10 ml) and ethanol (10 ml) at 0° C. The reaction mixture was stirred for overnight at room temperature, and the solvent was evaporated in vacuo. The residue was resolved in ethyl acetate-water, and acidified with 10% aqueous KHSO$_4$. The whole was washed with water, brine, dried over MgSO$_4$, and evaporated in vacuo to give N-[(R)-1-[3-(1-tert-butoxycarbonyl-4-piperidyl)-(E)-acryloyl]-3-piperidylcarbonyl]-β-alanine as a colorless oil (1.64 g).

IR (Film): 2930, 2855, 1720, 1625 cm$^{-1}$; NMR (DMSO-d$_6$, δ): 1.14–1.31 (2H, m), 1.39 (9H, s), 1.50–1.85 (6H, m), 2.11–2.31 (2H, m), 2.37 (2H, t, J=6.8 Hz), 2.56–3.29 (7H, m), 3.90–4.01 (2H, m), 4.17–4.43 (1H, m), 6.43 (1H, d, J=15.2 Hz), 6.60 (1H, dd, J=15.2 and 6.3 Hz), 7.99 (1H, t, J=5.4 Hz), 12.13 (1H, br); MASS (m/z): 438 (M$^+$+1).

EXAMPLE 33

To a solution of N-[(R)-1-[3-(1-tert-butoxycarbonyl-4-piperidyl)-(E)-acryloyl]-3-piperidylcarbonyl]-β-alanine ethyl ester (0.8 g) in ethyl acetate (8 ml) was added 4N HCl in ethyl acetate (4.3 ml) at 0° C., and the reaction mixture was stirred for 2 hours at room temperature. The reaction mixture was concentrated in vacuo, and resolved in water, neutralized with saturated aqueous NaHCO$_3$, desalted by using the resin of HP-20 eluting with isopropanol-H$_2$O (1:1), then freeze-dried to give N-[(R)-1-[3-(4-piperidyl)-(E)-acryloyl]-3-piperidylcarbonyl]-β-alanine ethyl ester (458 mg).

IR (KBr pellet): 3406, 2993, 2945, 2856, 2821, 2735, 1730, 1655 cm$^{-1}$; NMR (D$_2$O, δ): 1.27 (3H, t, J=7.1 Hz), 1.46–1.88 (6H, m), 1.92–2.07 (3H, m), 2.39–2.57 (2H, m), 2.60 (2H, t, J=6.2 Hz), 2.96–3.30 (4H, m), 3.39–3.49 (4H, m), 3.95–4.38 (2H, m), 4.17 (2H, q, J=7.1 Hz), 6.48 (1H, d, J=15.7 Hz), 6.60–6.73 (1H, m); MASS (m/z): 366 (M$^+$+1).

EXAMPLE 34

To a solution of N-[(R)-1-[3-(1-tert-butoxycarbonyl-4-piperidyl)-(E)-acryloyl]-3-piperidylcarbonyl]-β-alanine (1.64 g) in ethyl acetate (16 ml) was added 4N HCl in ethyl acetate (9.37 ml) at 0° C., and the reaction mixture was stirred for 2 hours at room temperature. The precipitates were filtered, washed with ether and resolved in water, neutralized with saturated aqueous NaHCO$_3$, desalted by using the resin of HP-20 eluting with isopropanol-H$_2$O (1:1), then freeze-dried to give N-[(R)-1-[3-(4-piperidyl)-(E)-acryloyl]-3-piperidylcarbonyl]-β-alanine as a white powder (690 mg).

IR (KBr pellet): 3392, 3074, 2943, 2862, 2746, 2522, 1652 cm$^{-1}$; NMR (D$_2$O, δ): 1.42–2.09 (9H, m), 2.39 (2H, t, J=6.8 Hz), 2.43–2.70 (2H, m), 2.94–3.16 (3H, m), 3.20–3.51 (5H, m) 3.97–4.38 (2H, m), 6.47 (1H, d, J=15.5 Hz), 6.59–6.72 (1H, m); MASS (m/z): 339 (M$^+$+1); [α]$_D^{20}$=−43.17° (C=1.0, MeOH).

EXAMPLE 35

To a mixture of 3(R)-(3,4-dimethoxyphenethyl)-β-alanine methyl ester (0.87 g), (R)-1-[3-(1-tert-butoxycarbonyl-4-piperidyl)-(E)-acryloyl]-3-piperidinecarboxylic acid (1.19 g) and 1-hydroxybenztriazole (0.44 g) in dimethylformamide (9 ml) was added 1-ethyl-3-(3-dimethylaminopropyl) carbodiimide (0.59 ml) at 0° C. The reaction mixture was stirred overnight at room temperature, and then poured into water. The whole was extracted with ethyl acetate, washed with aqueous saturated NaHCO$_3$, water, and brine, dried over MgSO$_4$, and evaporated in vacuo, subsequently. The residue was purified by column chromatography on silica gel eluting with ethyl acetate: n-hexane=(5:1) to give N-[(R)-1-[3-(1-tert-butoxycarbonyl-4-piperidyl)-(E)-acryloyl]-3-piperidylcarbonyl]-3(R)-(3,4-dimethoxyphenethyl)-β-alanine methyl ester as a colorless oil (1.83 g).

IR (Film): 2980, 2930, 2850, 1730, 1650, 1600 cm$^{-1}$; NMR (CDCl$_3$, δ): 1.26–1.40 (2H, m), 1.46 (9H, s), 1.68–1.91 (7H, m), 2.22–2.40 (3H, m), 2.49–2.82 (6H, m), 3.35–3.69 (2H, m), 3.65 (3H, s), 3.85 (3H, s), 3.87 (3H, s), 3.94–4.17 (3H, m), 4.26–4.37 (1H, m), 6.18–6.36 (2H, m), 6.72–6.86 (5H, m); MASS (m/z): 616 (M$^+$+1).

The following compounds [Examples 36 to 64] were obtained according to a similar manner to that of Example 35.

EXAMPLE 36

N-[(R)-1-[3-(1-tert-Butoxycarbonyl-1,2,3,6-tetrahydro-4-pyridyl)-(E)-acryloyl]-3-piperidylcarbonyl]-3(3)-ethynyl-β-alanine Ethyl Ester IR (Film): 3260, 1730, 1690, 1640, 1620 cm$^{-1}$; NMR (CDCl$_3$, δ): 1.24–1.31 (3H, m), 1.47 (9H, s), 1.50–1.55 (2H, br), 1.88–2.04 (2H, m), 2.27 (1H, d, J=2.4 Hz), 2.35 (3H, br), 2.68–2.71 (2H, m), 3.40 (2H, br), 3.54–3.60 (2H, m), 3.65–3.75 (1H, m), 4.07–4.18 (6H, m), 5.09 (1H, br), 6.03 (1H, br), 7.28 (1H, d, J=15.0 Hz);

EXAMPLE 37

N-[(R)-1-[3-(1-tert-Butoxycarbonyl-4-piperidyl)-(Z)-acryloyl]-3-piperidylcarbonyl]-3(S)-ethynyl-β-alanine Ethyl Ester IR (Film): 3250, 1720, 1690, 1640, 1600 cm$^{-1}$; NMR (CDCl$_3$, δ): 1.26 (3H, t, J=7.2 Hz), 1.20–1.46 (2H, m), 1.46 (9H, s), 1.65–1.77 (4H, m), 1.90–2.13 (3H, m), 2.29 (1H, d, J=2.4 Hz), 2.35 (1H, br), 2.73–2.91 (5H, m), 3.18–3.30 (2H, m), 3.67–3.94 (1H, m), 3.94–4.24 (2H, m), 4.18 (2H, t, J=7.2 Hz), 5.09–5.11 (1H, m), 5.67–5.77 (1H, m), 5.93–6.04 (1H, m); MASS (m/z): 490 (M$^+$+1).

EXAMPLE 38

N-[(R)-1-[3-(1-tert-Butoxycarbonyl-4-piperidyl)-(E)-acryloyl]-3-piperidylcarbonyl]-3(S)-(3-methyl-5-isoxazolyl)-β-alanine Ethyl Ester IR (Film): 3420, 3250, 1730, 1670, 1660, 1590 cm$^{-1}$; NMR (CDCl$_3$, δ): 1.20–1.29 (6H, m), 1.46 (9H, s), 1.71–1.77 (4H, m), 1.90 (1H, br), 2.26 (3H, s), 2.30–2.45 (2H, m), 2.70–2.90 (4H, m), 3.39–3.65 (2H, m), 4.06–4.17 (6H, m), 5.54–5.58 (1H, m), 6.00 (1H, s), 6.23 (1H, d, J=15.5 Hz), 6.82 (1H, dd, J=6.6 and 15.5 Hz).

EXAMPLE 39

N-[(R)-1-[3-(1-tert-Butoxycarbonyl-4-piperidyl)-(E)-acryloyl]-3-piperidylcarbonyl-3(R)-(4-methoxyphenethyl)-β-alanine Methyl Ester IR (Film): 2930, 2840, 1725, 1680, 1660, 1600 cm$^{-1}$; NMR (CDCl$_3$, δ): 1.30–1.40 (2H, m), 1.46 (9H, s), 1.44–1.95 (8H, m), 2.19–2.39 (3H, m), 2.48–2.84 (6H, m), 3.32–3.70 (5H, m), 3.78 (3H, s), 3.97–4.35 (4H, m), 6.16–6.35, 6.74–6.86 (total 2H, m), 6.78 (3H, q, J=6.9 Hz), 7.09 (2H, d, J=8.5 Hz); MASS (m/z): 586 (M$^+$+1).

EXAMPLE 40

N-[(R)-1-[3-(1-tert-Butoxycarbonyl-4-piperidyl)-(E)-acryloyl]-3-piperidylcarbonyl]-3(S)-methoxymethyl-β-alanine Methyl Ester IR (Film): 2955, 2850, 1720, 1640, 1600 cm$^{-1}$; NMR (CDCl$_3$, δ): 1.15–1.77 (9H, m), 1.46 (9H, s), 1.89–2.07 (2H, m), 2.23–2.38 (2H, m), 2.59 (2H, d, J=6.1 Hz), 2.70–2.81 (3H, m), 3.20–3.51 (2H, m), 3.34 (3H, s), 3.96–4.29 (3H, m), 4.36–4.50 (1H, m), 3.68 (3H, m), 6.23 (1H, d, J=15.3 Hz), 6.82 (1H, dd, J=15.3 and 6.7 Hz); MASS (m/z): 496 (M$^+$+1).

EXAMPLE 41

N-[(R)-1-[3-(1-tert-Butoxycarbonyl-4-piperidyl)-(E)-acryloyl]-3-piperidylcarbonyl]-3-ethynyl-β-alanine Ethyl Ester IR (Film): 3250, 2960, 2920, 2850, 1710, 1650, 1600 cm$^{-1}$; NMR (CDCl$_3$, δ): 1.14–1.61 (6H, m), 1.46 (9H, s), 1.69–1.80 (3H, m), 1.90–2.05 (2H, m), 2.23–2.40 (2H, m), 2.28 (1H, d, J=2.4 Hz), 2.61–2.81 (4H, m), 3.27–3.38 (2H, m), 3.65–3.80 (1H, m), 4.07–4.24 (5H, m), 5.04–5.17 (1H, m), 6.24 (1H, d, J=15.0 Hz), 6.82 (1H, dd, J=15.0 and 6.7 Hz), 7.03–7.23 (1H, m); MASS (m/z): 490 (M$^+$+1).

EXAMPLE 42

N-[(S)-1-[3-(1-tert-Butoxycarbonyl-4-piperidyl)-(E)-acryloyl]-3-piperidylcarbonyl]-3-ethynyl-β-alanine Ethyl Ester IR (Film): 2960, 2925, 2850, 1715, 1650, 1600 cm$^{-1}$; NMR (CDCl$_3$, δ): 1.28 (3H, t, J=7.1 Hz), 1.22–1.60 (4H, m), 1.46 (9H, s), 1.69–1.77 (4H, m), 1.89–2.05 (1H, m), 2.23–2.40 (2H, m), 2.28 (1H, d, J=2.4 Hz), 2.69–2.82 (4H, m), 3.25–3.43 (2H, m), 3.65–3.78 (1H, m), 4.10–4.20 (4H, m), 5.04–5.15 (1H, m), 6.30 (1H, d, J=15.2 Hz), 6.82 (1H, dd, J=15.2 and 6.6 Hz), 6.61–6.77, 7.05–7.15 (total 1H, m); MASS (m/z): 490 (M$^+$+1).

EXAMPLE 43

N-[1-[3-(1-tert-Butoxycarbonyl-4-piperidyl)-(E)-acryloyl]-4-piperidylcarbonyl]-3(S)-ethynyl-β-alanine Ethyl Ester IR (Film): 3030, 2970, 2825, 2850, 1730, 1645, 1600 cm$^{-1}$; NMR (CDCl$_3$, δ): 1.29 (3H, t, J=7.1 Hz), 1.25–1.50 (2H, m), 1.46 (9H, s), 1.57–1.79 (3H, m), 1.84–1.96 (2H, m), 2.20–2.44 (2H, m), 2.28 (1H, d, J=2.4 Hz), 2.68–2.82 (6H, m), 2.99–3.15 (1H, m), 3.95–4.24 (5H, m), 4.54–4.68 (1H, m), 5.06–5.16 (1H, m), 6.22 (1H, d, J=15.2 Hz), 6.60 (1H, d, J=8.7 Hz), 6.80 (1H, dd, J=15.2 and 6.7 Hz); MASS (m/z): 490 (M$^+$+1).

EXAMPLE 44

N-[(R)-1-[3-(1-tert-Butoxycarbonyl-4-piperidyl)-(E)-acryloyl]-3-piperidylcarbonyl]-3(S)-trifluoroacetylaminomethyl-β-alanine tert-butyl Ester

EXAMPLE 45

N-[(R)-1-[3-(1-tert-Butoxycarbonyl-4-piperidyl)-(E)-acryloyl]-3-piperidylcarbonyl]-2(S)-(4-trifluoromethylbenzoylamino)-β-alanine Ethyl Ester IR (Nujol): 1730 cm$^{-1}$; NMR (CDCl$_3$, δ): 1.05–1.40 (2H, m), 1.29 (3H, t, J=7.3 Hz), 1.45 (9H, s), 1.45–1.75 (4H, m), 2.05–2.45 (2H, m), 2.45–2.85 (3H, m), 3.20–3.60 (3H, m), 3.60–3.95 (2H, m), 3.95–4.30 (6H, m), 4.75–4.95 (1H, m), 6.18 (1H, d, J=15.3 Hz), 6.64 (1H, dd, J=15.3 and 6.4 Hz), 7.72 (3H, d-like), 7.85–8.25 (3H, m); MASS (m/z): 653 (M$^+$+1).

EXAMPLE 46

N-[(R)-1-[3-(1-tert-Butoxycarbonyl-4-piperidyl)-(E)-acryloyl]-3-piperidylcarbonyl]-2(S)-trifluoroacetylamino-β-alanine Ethyl Ester NMR (CDCl$_3$, δ): 1.20–1.40 (2H, m), 1.26 (3H, t, J=7.2 Hz), 1.50–1.95 (6H, m), 2.10–2.45 (2H, m), 2.45–2.90 (3H, m), 3.20–3.55 (2H, m), 3.55–3.90 (1H, m), 3.95–4.45 (7H, m), 4.60–4.80 (1H, m), 6.21 (1H, d, J=15.3 Hz), 6.81 (1H, dd, J=15.2 and 6.6 Hz), 8.30–8.55 (1H, br); MASS (m/z): 577 (M$^+$+1).

EXAMPLE 47

N-[(R)-1-[3-(1-tert-Butoxycarbonyl-3-azetidinyl)-(E)-acryloyl]-3-piperidylcarbonyl]-3(S)-ethynyl-β-alanine Ethyl Ester IR (Neat): 1660 cm$^{-1}$; NMR (CDCl$_3$, δ): 1.29 (3H, t, J=7.1 Hz), 1.35–1.60 (1H, m), 1.44 (9H, s), 1.60–2.15 (2H, m), 2.15–2.45 (2H, m), 2.50–2.85 (3H, m), 3.10–3.50 (3H, m), 3.55–4.05 (5H, m), 4.05–4.30 (5H, m), 5.00–5.20 (1H, m), 6.20–6.40 (1H, m), 6.60–6.85 (1H, br), 7.00 (1H, dd, J=15.0 and 8.2 Hz); MASS (m/z): 462 (M$^+$+1).

EXAMPLE 48

N-[(R)-1-[4-(1-tert-Butoxycarbonyl-3-azetidinyl)-(E)-2-butenoyl]-3-piperidylcarbonyl]-3(S)-ethynyl-β-alanine Ethyl Ester NMR (CDCl$_3$, δ): 1.28 (3H, t, J=7.1 Hz), 1.35–2.00 (7H, m), 1.43 (9H, s), 2.20–2.85 (6H, m), 2.28 (1H, d, J=2.4 Hz), 3.05–3.85 (4H, m), 4.02 (2H, t, J=8.5 Hz), 4.10–4.23 (2H, m), 5.05–5.15 (1H, m), 6.15–6.40 (1H, m), 6.68–6.83 (1H, m), 6.85–7.15 (1H, m); MASS (m/z): 476 (M$^+$+1).

EXAMPLE 49

N-[(R)-1-[(2-tert-Butoxycarbonyl-1,2,3,4-tetrahydroisoquinolin-6-yl)carbonyl]-3-piperidylcarbonyl]-3(S)-ethynyl-β-alanine Ethyl Ester IR (Nujol): 1670 cm$^{-1}$; NMR (CDCl$_3$, δ): 1.28 (3H, t, J=7.1 Hz), 1.35–2.15 (6H, m), 1.49 (9H, s), 2.29 (1H, d, J=2.3 Hz), 2.35–3.00 (5H, m), 3.00–3.60 (2H, m), 3.65 (2H, t, J=5.8 Hz), 4.05–4.40 (1H, m), 4.18 (2H, q, J=7.1 Hz), 4.58 (2H, s), 5.00–5.25 (1H, m), 7.05–7.25 (3H, m); MASS (m/z): 512 (M$^+$+1).

EXAMPLE 50

N-[(R)-1-[3-(1-tert-Butoxycarbonyl- 4-piperidyl)-(E)-methacryloyl]-3-piperidylcarbonyl]-3(S)-ethynyl-β-alanine Ethyl Ester IR (Neat): 1730, 1660 cm$^{-1}$; NMR (CDCl$_3$, δ): 1.15–1.55 (2H, m), 1.29 (3H, t, J=7.1 Hz), 1.46 (9H, s), 1.55–1.80 (5H, m), 1.80–2.05 (2H, m), 1.87 (3H, d, J=1.4 Hz), 2.20–2.55 (2H, m), 2.28 (3H, d, J=2.4 Hz), 2.55–2.90 (4H, m), 3.00–3.50 (1H, m), 3.50–3.95 (1H, m), 4.00–4.20 (2H, m), 4.19 (2H, q, J=7.1 Hz), 5.00–5.20 (1H, m), 5.33 (1H, d, J=9.1 Hz);

EXAMPLE 51

N-[(R)-1-[3-(1-tert-Butoxycarbonyl-4-piperidyl)-(E)-acryloyl]-3-piperidylcarbonyl]-3,3-dimethyl-β-alanine Ethyl Ester NMR (CDCl$_3$, δ): 1.26 (3H, t, J=7.1 Hz), 1.25–1.40 (2H, m), 1.41 (3H, s), 1.33 (3H, s), 1.41 (9H, s), 1.50–1.75 (5H, m), 1.80–2.05 (2H, m), 2.10–2.40 (2H, m), 2.60–2.85 (4H, m), 3.10–3.35 (2H, m), 3.60–3.90 (1H, m), 4.00–4.35 (2H, m), 4.13 (2H, q, J=7.1 Hz), 6.05–6.45 (2H, m), 6.81 (1H, dd, J=15.3 and 6.7 Hz); MASS (m/z): 494 (M$^+$+1).

EXAMPLE 52

N-[(R)-1-[2-[1-tert-Butoxycarbonyl-4-piperidyl]-(1R*,2S*)-cyclopropan-1-yl]carbonyl]-3-piperidylcarbonyl]-3(S)-ethynyl-β-alanine Ethyl Ester IR (Neat): 1730, 1660 cm$^{-1}$; NMR (CDCl$_3$, δ): 0.60–1.05 (3H, m), 1.05–1.40 (9H, m), 1.45 (9H, s), 1.50–1.85 (8H, m), 1.85–2.20 (2H, m), 2.20–2.50 (2H, m), 2.50–2.90 (4H, m), 3.15–3.55 (2H, m), 3.60–4.30 (6H, m), 5.00–5.20 (1H, m); MASS (m/z): 504 (M$^+$+1).

EXAMPLE 53

N-[(R)-1-[3-(1-tert-Butoxycarbonyl-4-piperidyl)-3-methyl-(E)-acryloyl]-3-piperidylcarbonyl]-3(S)-ethynyl-β-alanine Ethyl Ester IR (Neat): 1740, 1670, 1610 cm$^{-1}$; NMR (CDCl$_3$, δ): 1.29 (3H, t, J=7.1 Hz), 1.30–1.55 (2H, m), 1.46 (9H, s), 1.55–1.80 (2H, m), 1.84 (3H, s), 1.85–2.25 (2H, m), 2.25–2.45 (1H, m), 2.26 (1H, d, J=2.4 Hz), 2.55–2.85 (5H, m), 3.05–3.40 (2H, m), 3.50–3.80 (1H, m), 4.05–4.35 (4H, m), 5.00–5.20 (1H, m), 5.70–5.90 (1H, m).

EXAMPLE 54

N-[(R)-1-[4-(1-tert-Butoxycarbonyl-3-piperidyl)-(E)-2-butenoyl]-3-piperidylcarbonyl]-3(S)-ethynyl-β-alanine Ethyl Ester IR (Neat): 1730, 1680, 1660 cm$^{-1}$; NMR (CDCl$_3$, δ): 1.00–2.40 (12H, m), 1.28 (3H, m), 1.45 (9H, s), 2.40–2.90 (5H, m), 3.05–3.45 (3H, m), 3.50–4.30 (4H, m), 4.18 (2H, q, J=7.1 Hz), 5.00–5.20 (1H, m), 6.27 (1H, d, J=15.0 Hz), 6.65–7.00 (1H, m); MASS (m/z): 504 (M$^+$+1).

EXAMPLE 55

N-[(R)-1-[3-(1-tert-Butoxycarbonyl-4-piperidyl)-(E)-acryloyl]-3-piperidylcarbonyl]-β-alanine 1-(cyclohexyloxycarbonyloxy)ethyl Ester IR (Film): 2930, 2850, 1750, 1650, 1600 cm$^{-1}$; NMR (CDCl$_3$, δ): 1.26–1.58 (15H, m), 1.51 (9H, s), 1.69–1.81 (6H, m), 1.89–2.00 (4H, m), 2.20–2.38 (2H, m), 2.55 (2H, t, J=6.0 Hz), 2.70–2.84 (2H, m), 3.20–3.34 (1H, m), 3.44–3.61 (2H, m), 4.07–4.17 (2H, m), 4.57–4.91 (1H, m), 6.25 (1H, d, J=15.3 Hz), 6.69–6.79 (1H, m), 6.81 (1H, dd, J=15.3 and 6.7 Hz); MASS (m/z): 608 (M$^+$+1).

EXAMPLE 56

Methyl 3-[(R)-1-[3-(1-tert-butoxycarbonyl-4-piperidyl)-(E)-acryloyl]-3-piperidylcarbonyl]aminobenzoate IR (Film): 3070, 3000, 2940, 2850, 1710, 1680, 1650, 1600 cm$^{-1}$; NMR (CDCl$_3$, δ): 1.29–1.47 (2H, m), 1.45 (9H, s), 1.57–2.00 (5H, m), 2.21–2.40 (2H, m), 2.59–2.84 (3H, m), 3.54–3.61 (2H, m), 3.90 (3H, s), 3.90–3.96 (2H, m), 4.05–4.17 (2H, m), 6.24 (1H, d, J=15.3 Hz), 6.90 (1H, dd, J=15.1 and 6.4 Hz), 7.38 (1H, t, J=8.0 Hz), 7.75–7.86 (2H, m), 8.27 (1H, s), 9.25 (1H, s); MASS (m/z): 500 (M$^+$+1).

EXAMPLE 57

Ethyl 4-[(R)-1-[3-(1-tert-butoxycarbonyl-4-piperidyl)-(E)-acryloyl]-3-piperidylcarbonyl]aminobenzoate IR (Film): 3100, 2980, 2930, 2850, 1700, 1660, 1600 cm$^{-1}$; NMR (CDCl$_3$, δ): 1.26–1.46 (2H, m), 1.39 (3H, t, J=7.1 Hz), 1.46 (9H, s), 1.57–1.79 (5H, m), 2.21–2.45 (2H, m), 2.66–2.84 (3H, m), 3.48–3.80 (3H, m), 4.06–4.23 (3H, m), 4.36 (2H, q, J=7.1 Hz), 6.23 (1H, d, J=14.4 Hz), 6.84–6.95 (1H, m), 7.73 (2H, d, J=8.6 Hz), 8.00 (2H, d, J=8.6 Hz), 9.36 (1H, s); MASS (m/z): 514 (M$^+$+1).

EXAMPLE 58

Methyl 2-[(R)-1-[3-(1-tert-butoxycarbonyl-4-piperidyl)-(E)-acryloyl]-3-piperidylcarbonyl]aminobenzoate IR (Film): 2960, 2925, 2850, 1720, 1650, 1600 cm$^{-1}$; NMR (CDCl$_3$, δ): 1.26–1.46 (2H, m), 1.46 (9H, s), 1.70–1.91 (6H, m), 2.13–2.37 (2H, m), 2.45–2.60 (1H, m), 2.68–2.84 (2H, m), 2.90–3.46 (2H, m), 3.94 (3H, s), 4.04–4.19 (3H, m), 6.34 (1H, d, J=15.2 Hz), 6.84 (1H, dd, J=15.2 and 2.6 Hz), 7.05–7.14 (total 1H, m), 7.51–7.60 (1H, m), 8.03–8.07 (1H, m), 8.69 (1H, d, J=8.5 Hz), 11.19–11.34 (1H, m); MASS (m/z): 500 (M$^+$+1).

EXAMPLE 59

Methyl 3-[(R)-1-[3-(1-tert-butoxycarbonyl-4-piperidyl)propanoyl]-3-piperidylcarbonyl]aminobenzoate IR (Film): 2930, 1715, 1660, 1610 cm$^{-1}$; NMR (CDCl$_3$, δ): 0.97–1.19 (2H, m.), 1.45 (9H, s), 1.52–1.95 (9H, m), 2.27–2.45 (3H, m), 2.53–2.74 (3H, m), 3.38–3.59 (1H, m), 3.70–3.80 (1H, m), 3.91 (3H, s), 4.00–4.12 (3H, m), 7.38 (1H, t, J=7.9 Hz), 7.75–7.84 (2H, m), 8.26 (1H, s), 8.89 (1H, s); MASS (m/z): 402 (M$^+$-Boc+1).

EXAMPLE 60

Ethyl 4-[(R)-1-[3-(1-tert-butoxycarbonyl-4-piperidyl)propanoyl]-3-piperidylcarbonyl]aminobenzoate IR (Film): 2960, 2930, 2850, 1680, 1600 cm$^{-1}$; NMR (CDCl$_3$, δ): 0.98–1.18 (2H, m), 1.38 (3H, t, J=7.1 Hz), 1.44 (9H, s), 1.51–1.97 (8H, m), 2.25–2.45 (3H, m), 2.53–2.69 (3H, m), 3.46–3.54 (2H, m), 3.76–3.84 (1H, m), 3.93–4.10 (3H, m), 4.35 (2H, q, J=7.1 Hz), 7.70 (2H, d, J=8.7 Hz), 7.99 (2H, d, J=8.7 Hz), 9.20 (1H, s); MASS (m/z): 416(M$^+$-Boc+1).

EXAMPLE 61

Methyl 2-[(R)-1-[3-(1-tert-butoxycarbonyl-4-piperidyl)propanoyl]-3-piperidylcarbonyl]aminobenzoate IR (Film): 3260, 2960, 2920, 2850, 1715, 1670, 1620, 1610 cm$^{-1}$; NMR (CDCl$_3$, δ): 1.02–1.22 (2H, m), 1.45 (9H, s), 1.57–1.93 (7H, m), 2.37–3.40 (9H, m), 3.94 (3H, s), 4.00–4.15 (3H, m), 4.39–4.89 (1H, m), 7.05–7.17 (1H, m), 7.51–7.60 (1H, m), 8.01–8.10 (1H, m), 8.67–8.72 (1H, m), 11.18–11.33 (1H, m); MASS (m/z): 502 (M$^+$-Boc+1).

EXAMPLE 62

N-[(R)-1-[3-(1-tert-Butoxycarbonyl-4-piperidyl)propanoyl]-3-piperidylcarbonyl]-3(S)-methoxymethyl-β-alanine Methyl Ester IR (Film): 2910, 2850, 1725, 1670, 1620 cm$^{-1}$; NMR (CDCl$_3$, δ): 1.03–1.26 (2H, m), 1.45 (9H, s), 1.37–2.07 (6H, m), 2.20–2.42 (4H, m), 2.54–2.73 (6H, m), 3.19–3.48 (5H, m), 3.34 (3H, s), 3.67 (3H, s), 4.03–4.16 (3H, m), 4.33–4.49 (1H, m), 6.31–6.67 (1H, m); MASS (m/z): 498 (M$^+$+1).

EXAMPLE 63

N-[(R)-1-[3-(1-tert-Butoxycarbonyl-1,2,3,6-tetrahydro-4-pyridyl)propanoyl]-3-piperidylcarbonyl]-3(S)-ethynyl-β-alanine Ethyl Ester IR (Film): 3260, 1730, 1600 (br) cm$^{-1}$; NMR (CDCl$_3$, δ): 1.25–1.32 (4H, m), 1.46 (9H, s), 1.70–1.75 (4H, br), 1.99–2.05 (4H, m), 2.27 (1H, d, J=2.4 Hz), 2.35–2.41 (4H, br), 2.67–2.71 (2H, m), 3.28–3.31 (2H, m), 3.46–3.52 (2H, m), 3.85 (2H, br), 4.07–4.19 (2H, m), 5.09 (1H, br), 5.38 (1H, br).

EXAMPLE 64

N-[(R)-1-[3-(1-tert-Butoxycarbonyl-1,2,3,6-tetrahydro-4-pyridyl)propanoyl]-3-piperidylcarbonyl]-3(S)-(3-methyl-5-isoxazolyl)-β-alanine Ethyl Ester IR (Film): 3260, 1720, 1650 (br) cm$^{-1}$; NMR (CDCl$_3$, δ): 1.21–1.30 (4H, m), 1.46 (9H, s), 1.55–2.07 (6H, m), 2.62 (3H, s), 2.20–2.50 (4H, m), 2.88–2.96 (2H, m), 3.22–3.52 (4H, m), 3.85 (1H, br), 3.98 (1H, br), 4.13 (3H, q, J=7.1 Hz), 5.38 (1H, br), 5.51–5.61 (1H, m), 5.99 (1H, br); MASS (m/z): 447 (M$^+$+1-Boc)

EXAMPLE 65

To a solution of N-tert-butoxycarbonyl-2-hydroxymethyl-β-alanine ethyl ester (0.5 g) in ethyl acetate (5 ml) was added 4N HCl in ethyl acetate (5.05 ml) at 0° C., and the reaction mixture was stirred for 2 hours at room temperature. The reaction mixture was concentrated in vacuo. The residue, (R)-1-[3-(1-tert-butoxycarbonyl-4-piperidyl)-(E)-acryloyl]-3-piperidinecarboxylic acid (0.74 g) and 1-hydroxybenztriazole (0.27 g) was dissolved in dimethylformamide (5 ml), and 1-ethyl-3-(3-dimethylaminopropyl)carbodiimide (0.55 ml) was added under stirring at 0° C. After stirring at ambient temperature for overnight, the mixture was poured into water. The whole was extracted with ethyl acetate, washed with aqueous saturated NaHCO$_3$, water, and brine, dried over MgSO$_4$, and evaporated in vacuo, subsequently. The residue was purified by column chromatography on silica gel eluting with CHCl$_3$:MeOH= (99:1) to give N-[(R)-1-[3-(1-tert-butoxycarbonyl-4-piperidyl)-(E)-acryloyl]-3-piperidylcarbonyl]-2-hydroxymethyl-β-alanine ethyl ester as a colorless oil (0.37 g, 36.9%).

IR (Film): 2970, 2930, 2850, 1720, 1645, 1600 cm$^{-1}$; NMR (CDCl$_3$, δ): 1.28 (3H, t, J=7.1 Hz), 1.32–1.46 (2H, m), 1.46 (9H, s), 1.53–2.14 (8H, m), 2.23–2.48 (2H, m), 2.70–2.81 (3H, m), 3.34–3.85 (5H, m), 3.99–4.19 (3H, m), 4.17 (2H, q, J=7.1 Hz), 6.23 (1H, d, J=15.1 Hz), 6.82 (1H, dd, J=15.2 and 6.7 Hz), 6.88–7.01 (1H, m); MASS (m/z): 496 (M$^+$+1).

The following compounds [Examples 66 to 72] were obtained according to a similar manner to that of Example 65.

EXAMPLE 66

N-[(R)-1-[3-(1-tert-Butoxycarbonyl-4-piperidyl)-(E)-acryloyl]-3-piperidylcarbonyl]-2-benzyloxymethyl-β-alanine Ethyl Ester IR (Film): 2980, 2940, 2870, 1730, 1680, 1660 cm$^{-1}$; NMR (CDCl$_3$, δ): 1.26 (3H, t, J=7.1 Hz), 1.25–1.46 (5H, m), 1.46 (9H, s), 1.63–1.91 (4H, m), 2.16–2.35 (2H, m), 2.68–2.88 (3H, m), 3.13–3.24 (1H, m), 3.52–3.80 (5H, m), 4.05–4.19 (3H, m), 4.17 (2H, q, J=7.1 Hz), 4.50 (2H, s), 6.23 (1H, d, J=15.2 Hz), 6.44–6.53 (1H, m), 6.80 (1H, dd, J=15.2 and 6.7 Hz), 7.27–7.35 (5H, m); MASS (m/z): 586 (M$^+$+1).

EXAMPLE 67

N-[(R)-1-[3-(1-tert-Butoxycarbonyl-4-piperidyl)-benzoyl]-3-piperidylcarbonyl]-3(S)-ethynyl-β-alanine Ethyl Ester IR (Film): 3000, 2970, 2860, 1725, 1670, 1620 cm$^{-1}$; NMR (CDCl$_3$, δ): 1.28 (3H, t, J=7.1 Hz), 1.20–1.31 (1H, m), 1.48 (9H, s), 1.40–2.04 (11H, m), 2.28 (1H, d, J=2.3 Hz), 2.34–2.89 (6H, m), 4.11–4.31 (5H, m), 5.06–5.16 (1H, m), 7.21–7.54 (4H, m); MASS (m/z): 540 (M$^+$+1).

EXAMPLE 68

N-[(R)-1-[4-(1-tert-Butoxycarbonyl-4-piperidyl)-benzoyl]-3-piperidylcarbonyl]-3(S)-ethynyl-β-alanine Ethyl Ester IR (Film): 3400, 2960, 2925, 2850, 1730, 1665, 1615 cm$^{-1}$; NMR (CDCl$_3$, δ): 1.26 (3H, t, J=7.1 Hz), 1.48 (9H, s), 1.57–2.04 (11H, m), 2.28 (1H, d, J=2.4 Hz), 2.36–2.86 (6H, m), 7.12 (2H, q, J=7.1 Hz), 4.20–4.28 (3H, m), 5.07–5.17 (1H, m), 7.23 (2H, d, J=8.2 Hz), 7.27 (1H, s), 7.35 (2H, d, J=8.2 Hz); MASS (m/z): 540 (M$^+$+1).

EXAMPLE 69

N-[(R)-1-[3-(1-tert-Butoxycarbonyl-4-piperidyl)-propanoyl]-3-piperidylcarbonyl]-2-benzyloxymethyl-β-alanine Ethyl Ester IR (Film): 2980, 2930, 2860, 1735, 1660, 1635 cm$^{-1}$; NMR (CDCl$_3$, δ): 1.01–1.20 (2H, m), 1.26 (3H, t, J=7.1 Hz), 1.35–1.73 (10H, m), 1.45 (9H, s), 1.79–1.91 (1H, m), 2.30–2.40 (2H, m), 2.60–2.73 (2H, m), 2.81–2.94 (2H, m), 3.06–3.23 (1H, m), 3.54–3.64 (3H, m), 3.68–3.79 (2H, m), 4.01–4.12 (3H, m), 4.17 (2H, q, J=7.1 Hz), 4.51 (2H, s), 7.26–7.36 (5H, m); MASS (m/z): 588 (M$^+$+1).

EXAMPLE 70

N-[(R)-1-[3-(1-tert-Butoxycarbonyl-4-piperidyl)-propanoyl]-3-piperidylcarbonyl]-2-hydroxymethyl-β-alanine Ethyl Ester IR (Film): 2970, 2930, 2855, 1710, 1660, 1620 cm$^{-1}$; NMR (CDCl$_3$, δ): 1.01–1.26 (2H, m), 1.28 (3H, t, J=7.1 Hz), 1.45 (9H, s), 1.53–1.78 (6H, m), 1.85–2.13 (3H, m), 2.32–2.40 (4H, m), 2.60–2.79 (3H, m), 3.24–3.96 (8H, m), 4.02–4.15 (2H, m), 4.17 (2H, q, J=7.1 Hz), 6.29–6.40, 6.77–6.88 (total 1H, m); MASS (m/z): 498 (M$^+$+1).

EXAMPLE 71

N-[(R)-1-[3-(1-tert-Butoxycarbonyl-4-piperidyl)-propanoyl]-3-piperidylcarbonyl]-2-benzoylaminomethyl-β-alanine Ethyl Ester IR (Film): 3070, 2975, 2930, 2850, 1725, 1640 cm$^{-1}$; NMR (CDCl$_3$, δ): 1.00–1.33 (3H, m), 1.30 (3H, t, J=7.1 Hz), 1.45 (9H, s), 1.52–1.83 (7H, m), 1.90–2.12 (2H, m), 2.53–2.44 (3H, m), 2.60–2.73 (2H, m), 2.83–2.95 (1H, m), 3.12–3.41 (3H, m), 4.02–4.14 (6H, m), 4.20 (2H, q, J=7.1 Hz), 6.92–7.04 (1H, m), 7.42–7.57 (4H, m), 7.83–7.86 (2H, m); MASS (m/z): 601 (M$^+$+1).

EXAMPLE 72

N-[(R)-1-[3-(1-tert-Butoxycarbonyl-4-piperidyl)-propanoyl]-3-piperidylcarbonyl]-2-acetylaminomethyl-β-alanine Ethyl Ester IR (Film): 2920, 2850, 1720, 1650 cm$^{-1}$; NMR (CDCl$_3$, δ): 1.01–1.21 (2H, m), 1.28 (3H, t, J=7.1 Hz), 1.45 (9H, s), 1.37–1.98 (11H, m), 2.02 (3H, s), 2.27–2.43 (3H, m), 2.62–2.84 (3H, m), 3.05–3.36 (3H, m), 3.73–4.23 (8H, m), 6.89–7.04 (1H, m); MASS (m/z): 539 (M$^+$+1).

EXAMPLE 73

A mixture of N-benzyl-3-cyclopropyl-β-alanine (1.35 g), 10% Pd—C (0.27 g) and ammonium formate (1.72 g) in ethanol (15 ml) was hydrogenated at atmospheric pressure for 2 hours. After the catalyst was removed by filtration, the filtrate was concentrated in vacuo. The residue, (R)-1-[3-(1-tert-butoxycarbonyl-4-piperidyl)-(E)-acryloyl]-3-piperidinecarboxylic acid (2 g) and 1-hydroxybenztriazole (0.74 g) was dissolved in dimethylformamide (20 ml), and 1-ethyl-3-(3-dimethylaminopropyl)carbodiimide (1 ml) was added under stirring at 0° C. After stirring at ambient temperature for overnight, the mixture was poured into water. The whole was extracted with ethyl acetate, washed with aqueous saturated NaHCO$_3$, water, and brine, and dried over MgSO$_4$, and evaporated in vacuo, subsequently. The residue was purified by column chromatography on silica gel eluting with n-hexane:AcOEt=(1:2) to give N-[(R)-1-[3-(1-tert-butoxycarbonyl-4-piperidyl)-(E)-acryloyl]-3-piperidylcarbonyl]-3-cyclopropyl-β-alanine methyl ester as a colorless oil (2.58 g, 93.5%).

IR (Film): 3300, 3080, 2980, 2930, 2960, 1725, 1650, 1600 cm$^{-1}$; NMR (CDCl$_3$, δ): 0.20–0.57 (4H, m), 0.92–1.09 (1H, m), 1.22–1.57 (8H, m), 1.46 (9H, s), 1.69–1.81 (3H, m), 1.85–2.05 (1H, m), 2.21–2.39 (2H, m), 2.57–2.83 (4H, m), 3.25–3.73 (3H, m), 4.07–4.18 (5H, m), 6.23 (1H, d, J=15.3 Hz), 6.82 (1H, dd, J=15.3 and 6.6 Hz), 6.79–6.93 (1H, m); MASS (m/z): 506 (M$^+$+1).

The following compound was obtained according to a similar manner to that of Example 73.

EXAMPLE 74

N-[(R)-1-[3-(1-tert-Butoxycarbonyl-4-piperidyl)-propanoyl]-3-piperidylcarbonyl)-3-cyclopropyl-β-alanine Ethyl Ester IR (Film): 2980, 2920, 2850, 1715, 1650, 1620 cm$^{-1}$; NMR (CDCl$_3$, δ): 0.20–0.57 (4H, m), 0.96–1.20 (2H, m), 1.23–1.31 (4H, m), 1.40–1.74 (9H, m), 1.45 (9H, s), 1.89–2.41 (4H, m), 2.56–2.75 (4H, m), 3.20–3.39 (1H, m), 3.49–3.65 (2H, m), 3.85–4.20 (5H, m), 6.50–6.84 (1H, m); MASS (m/z): 508 (M$^+$+1).

EXAMPLE 75

A solution of LiOH (0.11 g) in H$_2$O (10 ml) was added to a solution of N-[(R)-1-[3-(1-tert-butoxycarbonyl-4-piperidyl)-(E)-acryloyl]-3-piperidylcarbonyl]-3(R)-(3,4-dimethoxyphenethyl)-β-alanine methyl ester (1.83 g) in tetrahydrofuran (10 ml)-EtOH (10 ml) at 0° C. The reaction mixture was stirred for 3 hours at room temperature, and the solvent was evaporated in vacuo. The residue was resolved in ethyl acetate-water, and acidified with 10% aq. KHSO$_4$. The whole was washed with water and brine, dried over MgSO$_4$, and evaporated in vacuo to give N-[(R)-1-[3-(1-tert-butoxycarbonyl-4-piperidyl)-(E)-acryloyl]-3- piperidylcarbonyl]-3(R)-(3,4-dimethoxyphenethyl)-β-alanine as a colorless oil (1.33 g, 74.4%).

IR (Film): 2980, 2930, 2850, 1720, 1645 cm$^{-1}$; NMR (DMSO$_3$, δ): 1.18–1.33 (2H, m), 1.39 (9H, s), 1.64–1.91 (8H, m), 2.17–2.46 (5H, m), 2.57–3.19 (4H, m), 3.70 (3H, s), 3.73 (3H, s), 3.90–4.08 (5H, m), 4.17–4.46 (1H, m), 6.43 (1H, d, J=15.1 Hz), 6.61 (1H, dd, J=15.1 and 6.4 Hz), 6.45–6.85 (3H, m), 7.83 (1H, d, J=8.4 Hz), 12.09 (1H, s); MASS (m/z): 602 (M$^+$+1).

The following compounds [Examples 76 to 102] were obtained according to a similar manner to that of Example 75.

EXAMPLE 76

N-[(R)-1-[3-(1-tert-Butoxycarbonyl-4-piperidyl)-(E)-acryloyl]-3-piperidylcarbonyl]-3(R)-(4-methoxyphenethyl)-β-alanine IR (Film): 2950, 2890, 2820, 1690, 1630 cm$^{-1}$; NMR (DMSO-d$_6$, δ): 1.18–1.47 (4H, m), 1.39 (9H, s), 1.60–1.95 (8H, m), 2.11–2.44 (5H, m), 2.57–2.84 (3H, m), 3.71 (3H, s), 3.90–4.08 (4H, m), 4.21–4.44 (1H, m), 6.43 (1H, d, J=15.2 Hz), 6.66 (1H, dd, J=15.2 and 6.4 Hz), 6.82 (2H, d, J=8.6 Hz), 7.07 (2H, d, J=8.6 Hz), 7.83 (1H, d, J=8.4 Hz), 12.08 (1H, br); MASS (m/z): 572 (M$^+$+1).

EXAMPLE 77

N-[(R)-1-[3-(1-tert-Butoxycarbonyl-4-piperidyl)-(E)-acryloyl]-3-piperidylcarbonyl]-3(S)-methoxymethyl-β-alanine IR (Film): 3000, 2955, 2900, 1720, 1660 cm$^{-1}$; NMR (DMSO-d$_6$, δ): 1.06–1.33 (2H, m), 1.39 (9H, s), 1.55–1.83 (7H, m), 2.15–2.41 (6H, m), 2.64–2.84 (2H, m), 3.23 (3H, s), 3.77–3.97 (4H, m), 4.11–4.40 (2H, m), 6.42 (1H, d, J=15.2 Hz), 6.55–6.66 (1H, m), 7.84–7.93 (1H, m); MASS (m/z): 482 (M$^+$+1).

EXAMPLE 78

N-[(R)-1-[3-(1-tert-Butoxycarbonyl-4-piperidyl)-(E)-acryloyl]-3-piperidylcarbonyl]-3-cyclopropyl-β-alanine IR (Film): 3280, 2980, 2920, 2850, 1700, 1640 cm$^{-1}$; NMR (DMSO-d$_6$, δ): 0.08–0.43 (2H, m), 1.17–1.32 (2H, m), 1.29–1.85 (13H, m), 1.29 (9H, s), 2.11–2.45 (3H, m), 2.59–3.04 (2H, m), 3.51–3.70 (1H, m), 3.90–4.08 (3H, m), 6.43 (1H, d, J=15.2 Hz), 6.60 (1H, dd, J=15.2 and 6.5 Hz), 7.82 (1H, d,J=8.4 Hz), 12.08 (1H, br); MASS (m/z): 478 (M$^+$+1).

EXAMPLE 79

N-[(R)-1-[3-(1-tert-Butoxycarbonyl-4-piperidyl)-(E)-acryloyl]-3-piperidylcarbonyl]-2-hydroxymethyl-β-alanine IR (Film): 3300, 2930, 2870, 1720, 1650, 1600 cm$^{-1}$; NMR (DMSO-d$_6$, δ): 1.08–1.44 (6H, m), 1.39 (9H, s), 1.50–1.87 (5H, m), 2.11–2.40 (2H, m), 2.57–3.25 (5H, m), 3.53 (2H, d, J=5.7 Hz), 3.90–4.01 (3H, m), 4.18–4.42 (1H, m), 6.40–6.68 (2H, m), 7.95–8.00 (1H, m); MASS (m/z): 468 (M$^+$+1).

EXAMPLE 80

N-[(R)-1-[3-(1-tert-Butoxycarbonyl-4-piperidyl)-(E)-acryloyl]-3-piperidylcarbonyl]-3-ethynyl-β-alanine IR (Film): 3270, 2925, 2855, 1720, 1650, 1600 cm$^{-1}$; NMR (DMSO-d$_6$, δ): 1.17–1.32 (2H, m), 1.37 (9H, s), 1.39–1.86 (7H, m), 2.11–2.40 (2H, m), 2.55–3.11 (6H, m), 3.21 (1H, d, J=2.3 Hz), 3.90–3.98 (2H, m), 4.13–4.45 (1H, m), 4.75–4.88 (1H, m), 6.42 (1H, d, J=15.3 Hz), 6.60 (1H, dd, J=15.3 and 6.3 Hz), 8.43 (1H, d, J=8.0 Hz); MASS (m/z): 462 (M$^+$+1).

EXAMPLE 81

N-[(S)-1-[3-(1-tert-Butoxycarbonyl-4-piperidyl)-(E)-acryloyl]-3-piperidylcarbonyl]-3-ethynyl-β-alanine IR (Film): 3260, 2925, 2850, 1720, 1645 cm$^{-1}$; NMR (DMSO-d$_6$, δ): 1.17–1.32 (2H, m), 1.39 (9H, s), 1.39–1.85 (6H, m), 2.10–2.40 (2H, m), 2.55–2.83 (6H, m), 3.21 (1H, d, J=2.3 Hz), 3.91–4.01 (3H, m), 4.14–4.44 (1H, m), 4.76–4.89 (1H, m), 6.42 (1H, d, J=15.2 Hz), 6.55–6.64 (1H, m), 8.42 (1H, d, J=8.2 Hz); MASS (m/z): 462 (M$^+$+1).

EXAMPLE 82

N-[1-[3-(1-tert-Butoxycarbonyl-4-piperidyl)-(E)-acryloyl]-4-piperidylcarbonyl]-3(S)-ethynyl-β-alanine IR (Film): 3220, 2925, 2880, 1715, 1645, 1600 cm$^{-1}$; NMR (DMSO-d$_6$, δ): 1.10–1.51 (4H, m), 1.39 (9H, s), 1.65–1.71 (4H, m), 2.23–2.43 (2H, m), 2.57 (2H, d, J=7.3 Hz), 2.65–2.87 (3H, m), 2.93–3.10 (1H, m), 3.19 (1H, d, J=2.3 Hz), 3.91–4.13 (3H, m), 4.28–4.41 (1H, m), 4.75–4.89 (1H, m), 6.42 (1H, d, J=15.2 Hz), 6.61 (1H, dd, J=15.2 and 6.4 Hz), 8.32 (1H, d, J=8.2 Hz); MASS (m/z): 462 (M$^+$+1).

EXAMPLE 83

N-[(R)-1-[3-(1-tert-Butoxycarbonyl-3-azetidinyl)-(E)-acryloyl]-3-piperidylcarbonyl]-3(S)-ethynyl-β-alanine NMR (CDCl$_3$, δ): 1.44 (9H, s), 1.45–2.20 (4H, m), 2.20–2.55 (2H, m), 2.55–2.90 (3H, m), 3.05–3.40 (3H, m), 3.40–4.05 (4H, m), 4.20–4.70 (1H, m), 5.00–5.20 (1H, m), 6.20–6.45 (1H, m), 6.60–7.20 (2H, m), 7.35–7.65 (1H, m); MASS (m/z): 334 (M$^+$+1-Boc).

EXAMPLE 84

N-[(R)-1-[3-(1-tert-Butoxycarbonyl-4-piperidyl)-(E)-methacryloyl]-3-piperidylcarbonyl]-3-(S)-ethynyl-β-alanine IR (Neat): 1730, 1650 cm$^{-1}$; NMR (CDCl$_3$, δ): 1.10–1.40 (2H, m), 1.40–2.20 (7H, m), 1.49 (9H, s), 1.84 (3H, d, J=1.4 Hz), 2.27 (1H, d, J=2.4 Hz), 2.35–3.20 (7H, m), 3.85–4.20 (3H, m), 4.45–4.85 (1H, m), 4.95–5.15 (1H, m), 5.15–5.30 (1H, m).

EXAMPLE 85

N-[(R)-1-[3-(1-tert-Butoxycarbonyl-4-piperidyl)-(E)-acryloyl]-3-piperidylcarbonyl]-3,3-dimethyl-β-alanine IR (Film): 1730, 1650 cm$^{-1}$; NMR (CDCl$_3$, δ): 1.39 (6H, s), 1.46 (9H, s), 1.50–2.45 (11H, m), 2.45–3.05 (4H, m), 3.05–3.40 (1H, m), 3.60–4.70 (6H, m), 6.10–6.60 (1H, m), 6.60–6.95 (1H, m).

EXAMPLE 86

N-[(R)-1-[2-(1-tert-Butoxycarbonyl-4-piperidyl)-(1R*,2S*)-cyclopropan-1-yl-carbonyl]-3-piperidylcarbonyl]-(3S)-ethynyl-β-alanine IR (Neat): 1720, 1650 cm$^{-1}$; NMR (CDCl$_3$, δ): 0.50–1.35 (6H, m), 1.35–2.20 (10H, m), 1.45 (9H, s), 2.20–2.45 (2H, m), 2.45–3.10 (4H, m), 3.10–4.60 (7H, m), 4.95–5.20 (1H, m), 6.45–6.95 (1H, br); MASS (m/z): 476 (M⁺+1).

EXAMPLE 87

N-[(R)-1-[3-(1-tert-Butoxycarbonyl-4-piperidyl)-3-methyl-(E)-acryloyl]-3-piperidylcarbonyl]-3(S)-ethynyl-β-alanine IR (Nujol): 1660 cm⁻¹; NMR (CDCl₃, δ): 1.15–1.60 (2H, m), 1.47 (9H, s), 1.60–2.45 (9H, m), 2.45–2.90 (5H, m), 2.90–3.25 (2H, m), 3.45–4.70 (6H, m), 4.90–5.20 (1H, m), 5.74 (1H, s); MASS (m/z): 476 (M⁺+1).

EXAMPLE 88

3-[(R)-1-[3-(1-tert-Butoxycarbonyl-4-piperidyl)-(E)-acryloyl]-3-piperidylcarbonyl]aminobenzoic Acid IR (Film): 3250, 3000, 2925, 2850, 1700, 1650 cm⁻¹; NMR (DMSO-d₆, δ): 1.09–1.49 (3H, m), 1.39 (9H, s), 1.38–1.81 (4H, m), 1.91–2.03 (1H, m), 2.20–2.46 (2H, m), 2.64–2.86 (3H, m), 2.97–3.15 (1H, m), 3.87–4.11 (3H, m), 4.13–4.53 (1H, m), 6.43–6.69 (2H, m), 7.42 (1H, t, J=7.9 Hz), 7.62 (1H, d, J=7.7 Hz), 7.82 (1H, d, J=8.0 Hz), 8.24 (1H, s), 10.17 (1H, s); MASS (m/z): 486 (M⁺+1).

EXAMPLE 89

4-[(R)-1-[3-(1-tert-Butoxycarbonyl-4-piperidyl)-(E)-acryloyl]-3-piperidylcarbonyl]aminobenzoic Acid IR (Film): 3000, 2925, 2850, 1700, 1670, 1650 cm⁻¹; NMR (DMSO-d₆, δ): 1.14–1.49 (3H, m), 1.39 (9H, s), 1.39–1.80 (5H, m), 1.91–2.03 (1H, m), 2.22–2.37 (1H, m), 2.63–2.84 (3H, m), 2.97–3.21 (1H, m), 3.87–4.12 (3H, m), 4.18–4.35 (1H, m), 6.42–6.69 (2H, m), 7.71 (2H, d, J=8.7 Hz), 7.79 (2H, d, J=8.7 Hz), 10.29 (1H, s), 12.41–12.60 (1H, br); MASS (m/z): 486 (M⁺+1).

EXAMPLE 90

2-[(R)-1-[3-(1-tert-Butoxycarbonyl-4-piperidyl)-(E)-acryloyl]-3-piperidylcarbonyl]aminobenzoic Acid IR (Film): 3000, 2930, 2860, 1720, 1660, 1600 cm⁻¹; NMR (DMSO-d₆, δ): 1.11–1.53 (5H, m), 1.39 (9H, s), 1.91–2.48 (4H, m), 2.60–3.10 (6H, m), 3.86–4.14 (4H, m), 6.46 (1H, d, J=7.1 Hz), 6.55–6.69 (1H, m), 7.15 (1H, t, J=7.1 Hz), 7.58 (1H, t, J=7.1 Hz), 7.98 (1H, d, J=8.1 Hz), 8.44 (1H, d, J=8.1 Hz), 11.30 (1H, br); MASS (m/z): 486 (M⁺+1).

EXAMPLE 91

N-[(R)-1-[3-(1-tert-Butoxycarbonyl- 4-piperidyl)-(E)-acryloyl]-3-piperidylcarbonyl]-2-benzyloxymethyl-β-alanine IR (Film): 3300, 2960, 2930, 2860, 1720, 1670, 1650 cm⁻¹; NMR (DMSO-d₆, δ): 1.10–1.33 (2H, m), 1.39 (9H, s), 1.39–1.83 (8H, m), 2.12–2.40 (2H, m), 2.57–2.84 (4H, m), 3.20–3.30 (1H, m), 3.57 (2H, d, J=6.1 Hz), 3.88–4.01 (3H, m), 4.18–4.41 (1H, m), 4.46 (2H, s), 6.42 (1H, d, J=15.2 Hz), 6.60 (1H, dd, J=15.2 and 6.4 Hz), 7.27–7.38 (5H, m), 7.93–8.00 (1H, m), 12.31 (1H, br); MASS (m/z): 558 (M⁺+1).

EXAMPLE 92

N-[(R)-1-[3-(1-tert-Butoxycarbonyl-4-piperidyl)-benzoyl]-3-piperidylcarbonyl]-3(S)-ethynyl-β-alanine IR (Film): 3380, 3000, 2930, 2860, 1720, 1650, 1620 cm⁻¹; NMR (DMSO-d₆, δ): 1.33–1.99 (8H, m), 1.41 (9H, s), 2.24–2.80 (2H, m), 2.55–2.80 (6H, m), 3.19 (1H, d, J=2.3 Hz), 3.40–3.63 (1H, m), 4.01–4.12 (2H, m), 4.27–4.45 (1H, m), 4.74–4.87 (1H, m), 7.13–7.21 (2H, m), 7.26–7.37 (2H, m), 8.33–8.46 (1H, m), 12.33–12.47 (1H, br); MASS (m/z): 512 (M⁺+1).

EXAMPLE 93

N-[(R)-1-[4-(1-tert-Butoxycarbonyl-4-piperidyl)-benzoyl]-3-piperidylcarbonyl]-3(S)-ethynyl-β-alanine IR (Film): 3350, 2925, 2850, 1720, 1655, 1605 cm⁻¹; NMR (DMSO-d₆, δ): 1.41 (9H, s), 1.41–1.91 (10H, m), 2.22–2.40 (1H, m), 2.51–3.00 (7H, m), 3.18 (1H, d, J=2.3 Hz), 4.01–4.12 (2H, m), 4.74–4.86 (1H, m), 7.30 (4H, s), 8.37–8.48 (1H, m), 12.35–12.41 (1H, br); MASS (m/z): 512 (M⁺+1).

EXAMPLE 94

N-[(R)-1-[3-(1-tert-Butoxycarbonyl-4-piperidyl)-propanoyl]-3-piperidylcarbonyl]-3(S)-methoxymethyl-β-alanine IR (Film): 2950, 2900, 1730, 1660, 1640 cm⁻¹; NMR (DMSO-d₆, δ): 0.87–1.08 (2H, m), 1.38 (9H, s), 1.26–1.83 (9H, m), 2.11–2.41 (6H, m), 2.55–2.74 (2H, m), 2.84–3.14 (2H, m), 3.24 (3H, s), 3.71–3.95 (4H, m), 4.13–4.35 (2H, m), 7.82–7.91 (1H, m), 12.06–12.29 (1H, br); MASS (m/z): 384(M⁺-Boc+1).

EXAMPLE 95

N-[(R)-1-[3-(1-tert-Butoxycarbonyl-4-piperidyl)-propanoyl]-3-piperidylcarbonyl]-3-cyclopropyl-β-alanine IR (Film): 3400, 3000, 2910, 2855, 1700, 1640, 1620 cm⁻¹; NMR (DMSO-d₆, δ): 0.11–0.46 (4H, m) 0.84–1.08 (3H, m), 1.23–1.44 (5H, m), 1.38 (9H, s), 1.53–1.82 (5H, m), 2.11–2.45 (5H, m), 2.51–2.75 (2H, m), 2.86–3.09 (1H, m), 3.56–3.80 (2H, m), 3.86–3.97 (2H, m), 4.13–4.39 (1H, m), 7.80–7.90 (1H, m); MASS (m/z): 480 (M⁺+1).

EXAMPLE 96

3-[(R)-1-[3-(1-tert-Butoxycarbonyl-4-piperidyl)-propanoyl]-3-piperidylcarbonyl]aminobenzoic Acid IR (Film): 3260, 3000, 2930, 2850, 1700, 1660, 1600 cm⁻¹; NMR (DMSO-d₆, δ): 0.84–1.07 (1H, m), 1.39 (9H, s), 1.37–1.50 (4H, m), 1.60–1.80 (5H, m), 1.91–1.99 (1H, m), 2.31–2.41 (2H, m), 2.51–2.79 (4H, m), 2.93–3.31 (1H, m), 3.79–4.00 (3H, m), 4.12–4.51 (1H, m), 7.42 (1H, d, J=7.6 Hz), 7.62 (1H, d, J=7.6 Hz), 7.76–7.85 (1H, m), 8.23 (1H, s), 10.16 (1H, d, J=3.7 Hz); MASS (m/z): 388 (M⁺-Boc+1).

EXAMPLE 97

4-[(R)-1-[3-(1-tert-Butoxycarbonyl-4-piperidyl)-propanoyl]-3-piperidylcarbonyl]aminobenzoic Acid IR (Film): 2930, 2850, 1760, 1600 cm⁻¹; NMR (DMSO-d₆, δ): 0.87–1.05 (1H, m), 1.38 (9H, s), 1.37–1.50 (5H, m), 1.60–1.80 (4H, m), 1.91–2.04 (1H, m), 2.31–2.40 (2H, m), 2.51–2.79 (4H, m), 2.95–3.22 (1H, m), 3.77–3.96 (3H, m), 4.12–4.49 (1H, m), 7.70 (2H, d, J=8.0 Hz), 7.89 (2H, d, J=8.4 Hz), 10.28 (1H, s); MASS (m/z): 388 (M⁺-Boc+1).

EXAMPLE 98

2-[(R)-1-[3-(1-tert-Butoxycarbonyl-4-piperidyl)-propanoyl]-3-piperidylcarbonyl]aminobenzoic Acid IR (Film): 2925, 2855, 1720, 1660, 1600 cm⁻¹; NMR (DMSO-d₆, δ): 0.83–1.09 (2H, m), 1.38 (9H, s), 1.38–1.78

(6H, m), 1.99–2.16 (1H, m), 2.26–2.41 (3H, m), 2.58–3.06 (5H, m), 3.68–4.56 (6H, m), 7.15 (1H, t, J=7.4 Hz), 7.51–7.60 (1H, m), 7.9 (1H, d, J=8.9 Hz), 8.41 (1H, t, J=7.3 Hz); MASS (m/z): 488 (M$^+$+1).

EXAMPLE 99

N-[(R)-1-[3-(1-tert-Butoxycarbonyl-4-piperidyl)-propanoyl]-3-piperidylcarbonyl]-2-benzyloxymethyl-β-alanine IR (Film): 3400, 2930, 2855, 1720, 1660, 1630 cm$^{-1}$; NMR (DMSO-d$_6$, δ): 0.83–1.09 (2H, m), 1.23–1.49 (8H, m), 1.38 (9H, s), 1.52–1.85 (4H, m), 2.25–2.37 (2H, m), 2.57–2.77 (4H, m), 2.93–3.11 (1H, m), 3.55–3.62 (2H, m), 3.69–3.97 (3H, m), 4.18–4.40 (1H, m), 4.46 (2H, s), 7.26–7.37 (5H, m), 7.89–7.99 (1H, m); MASS (m/z): 560 (M$^+$+1).

EXAMPLE 100

N-[(R)-1-[3-(1-tert-Butoxycarbonyl-4-piperidyl)-propanoyl]-3-piperidylcarbonyl]-2-hydroxymethyl-β-alanine IR (Film): 2930, 2860, 1720, 1660, 1620 cm$^{-1}$; NMR (DMSO-d$_6$, δ): 0.86–1.08 (2H, m), 1.38 (9H, s), 1.58–1.85 (11H, m), 2.13–2.37 (3H, m), 2.51–3.25 (5H, m), 3.53 (2H, d, J=5.1 Hz), 3.71–3.96 (4H, m), 4.13–4.39 (1H, m), 7.94–8.03 (1H, m); MASS (m/z): 470 (M$^+$+1).

EXAMPLE 101

N-[(R)-1-[3-(1-tert-Butoxycarbonyl-4-piperidyl)-propanoyl]-3-piperidylcarbonyl]-2-benzoylaminomethyl-β-alanine IR (Film): 3280, 3050, 2920, 2850, 1710, 1620 cm$^{-1}$; NMR (DMSO-d$_6$, δ): 0.84–1.05 (2H, m), 1.38 (9H, s), 1.35–1.46 (4H, m), 1.60–1.70 (4H, m), 1.76–1.86 (1H, m), 2.27–2.38 (2H, m), 2.51–3.15 (6H, m), 3.24–3.52 (4H, m), 3.74–3.95 (3H, m), 4.13–4.40 (1H, m), 7.43–7.54 (3H, m), 7.81–7.84 (2H, m), 8.00–8.11 (1H, m), 8.51–8.60 (1H, m); MASS (m/z): 573 (M$^+$+1).

EXAMPLE 102

N-[(R)-1-[3-(1-tert-Butoxycarbonyl-4-piperidyl)-propanoyl]-3-piperidylcarbonyl]-2-acetylaminomethyl-β-alanine IR (Film): 3325, 2920, 2850, 1720, 1640 cm$^{-1}$; NMR (DMSO-d$_6$, δ): 0.86–4.08 (2H, m), 1.17 (9H, s), 1.17–1.47 (4H, m), 1.60–1.71 (5H, m), 1.91 (3H, s), 2.28–2.40 (2H, m), 2.51–2.94 (6H, m), 3.14–3.44 (4H, m), 3.76–4.39 (4H, m), 7.89–8.03 (2H, m); MASS (m/z): 511 (M$^+$+1).

EXAMPLE 103

To a mixture of N-[(R)-1-[3-(1-tert-butoxycarbonyl-4-piperidyl)-(E)-acryloyl]-3-piperidylcarbonyl]-3(S)-ethynyl-β-alanine (0.6 g), n-pentylalcohol (0.16 ml) and N,N-dimethylaminopyridine (16 mg) in dichloromethane (6 ml) was added 1-ethyl-3-(3-dimethylaminopropyl)-carbodiimide hydrochloride (0.27 g) at 0° C. After stirring at room temperature for overnight, the solution was evaporated in vacuo. The residue was poured into water and extracted with ethyl acetate. The extract was washed with saturated aqueous sodium hydrogencarbonate, water and brine, dried over MgSO$_4$, and evaporated in vacuo, subsequently. The residue was purified by column chromatography on silica gel eluting with AcOEt:Hexane=(1:1) to give N-[(R)-1-[3-(1-tert-butoxycarbonyl-4-piperidyl)-(E)-acryloyl]-3-piperidylcarbonyl]-3(S)-ethynyl-β-alanine n-pentyl ester as a colorless oil (0.65 g, 94.0%).

IR (Film): 2900, 2825, 1710, 1640, 1600 cm$^{-1}$; NMR (DMSO-d$_6$, δ): 0.89–0.97 (3H, m), 1.26–1.40 (7H, m), 1.46 (9H, s), 1.61–1.79 (6H, m), 1.92–2.05 (1H, m), 2.28 (1H, d, J=2.3 Hz), 2.24–2.38 (2H, m), 2.68–2.83 (4H, m), 3.23–3.39 (2H, m), 3.64–4.26 (6H, m), 5.05–5.16 (1H, m), 6.22 (1H, d, J=15.2 Hz), 6.82 (1H, dd, J=15.2 and 6.6 Hz), 7.07–7.16 (1H, m); MASS (m/z): 532 (M$^+$+1).

The following compounds [Examples 104 to 107] were obtained according to a similar manner to that of Example 103.

EXAMPLE 104

N-[(R)-1-[3-(1-tert-Butoxycarbonyl-4-piperidyl)-(E)-acryloyl]-3-piperidylcarbonyl]-3(S)-ethynyl-β-alanine n-butyl Ester NMR (CDCl$_3$, δ): 0.96 (3H, t, J=7.3 Hz), 1.33 (2H, d, J=7.3 Hz), 1.36–1.45 (3H, m), 1.46 (9H, s), 1.56–1.77 (4H, s), 1.90–2.05 (2H, m), 2.20–2.31 (2H, m), 2.28 (1H, d, J=2.4 Hz), 2.60–2.81 (4H, m), 4.06–4.18 (5H, m), 5.05–5.13 (1H, m), 6.23 (1H, d, J=15.1 Hz), 6.82 (1H, dd, J=6.7 and 15.1 Hz); MASS (m/z): 518 (M$^+$+1).

EXAMPLE 105

N-[(R)-1-[3-(1-tert-Butoxycarbonyl-4-piperidyl)-(E)-acryloyl]-3-piperidylcarbonyl]-3(S)-ethynyl-β-alanine Phenethyl Ester IR (Film): 2930, 2850, 1730, 1650, 1600 cm$^{-1}$; NMR (CDCl$_3$, δ): 1.26–1.40 (2H, m), 1.46 (9H, s), 1.45–1.89 (8H, m), 1.95–2.04 (1H, m), 2.20–2.39 (1H, m), 2.25 (1H, d, J=2.4 Hz), 2.67–2.91 (4H, m), 2.97 (2H, t, J=7.0 Hz), 3.20–3.41 (1H, m), 4.07–4.17 (3H, m), 4.36 (2H, t, J=7.0 Hz), 5.01–5.13 (1H, m), 6.23 (1H, d, J=15.2 Hz), 6.82 (1H, dd, J=15.2 and 6.7 Hz), 7.21–7.51 (6H, m); MASS (m/z): 566 (M$^+$+1).

EXAMPLE 106

N-[(R)-1-[3-(1-tert-Butoxycarbonyl-4-piperidyl)-(E)-acryloyl]-3-piperidylcarbonyl]-β-alanine n-butyl Ester IR (Film): 2920, 2855, 1725, 1680, 1650, 1600 cm$^{-1}$; NMR (CDCl$_3$, δ): 0.94 (3H, t, J=7.2 Hz), 1.27–1.79 (12H, m), 1.46 (9H, s), 1.90–2.01 (1H, m), 2.23–2.36 (2H m), 2.52 (2H, t, J=6.1 Hz), 2.70–2.81 (2H, m), 3.29 (1H, dd, J=13.5 and 9.3 Hz), 3.65–3.76 (3H, m), 4.10 (2H, t, J=6.6 Hz), 4.00–4.20 (3H, m), 6.22 (1H, d, J=15.2 Hz), 6.55–6.68 (1H, m), 681 (1H, dd, J=15.2 and 6.7 Hz); MASS (m/z): 494 (M$^+$+1).

EXAMPLE 107

N-[(R)-1-[3-(1-tert-Butoxycarbonyl-4-piperidyl) propanoyl]-3-piperidylcarbonyl]-2(S)-acetylamino-β-alanine n-pentyl Ester IR (Film): 2910, 2850, 1720, 1640 cm$^{-1}$; NMR (CDCl$_3$, δ): 0.91 (3H, t, J=6.6 Hz), 1.00–1.22 (2H, m), 1.31–1.36 (4H, m), 1.45 (9H, s), 1.40–1.77 (13H, m), 2.04–2.09 (3H, m), 2.34–2.51 (3H, m), 2.60–2.74 (2H, m), 3.20–3.49 (2H, m), 3.57–3.75 (2H, m), 4.02–4.25 (5H, m), 4.57–4.80 (1H, m), 6.88–7.20 (1H, m); MASS (m/z): 467 (M$^+$-Boc+1).

EXAMPLE 108

To a solution of N-[(R)-1-[3-(1-tert-butoxycarbonyl-4-piperidyl)-(E)-acryloyl]-3-piperidylcarbonyl]-3(S)-ethynyl-β-alanine (0.5 g) in dimethylformamide (5 ml) was added K$_2$CO$_3$ (75 mg) under stirring at 0° C., stirred for 15 minutes, and pivalic acid iodomethyl ester (0.61 g) in dimethylformamide (3 ml) was added to the mixture. After stirring at room temperature for 1 hour, the mixture was poured into water and extracted with ethyl acetate. The extract was washed with water and brine, dried over MgSO$_{41}$ and evaporated in vacuo, subsequently. The residue was purified by column chromatography on silica gel eluting with CHCl$_3$:MeOH=(98:2) to give N-[(R)-1-[3-(1-tert-butoxycarbonyl-4-piperidyl)-(E)-acryloyl]-3-piperidylcarbonyl]-3(S)-ethynyl-β-alanine pivaloyloxymethyl ester as a colorless oil (0.37 g, 59.3%).

IR (Film): 2960, 2920, 2850, 1745, 1650, 1600 cm$^{-1}$; NMR (CDCl$_3$, δ): 1.22 (9H, s), 1.32–1.60 (3H, m), 1.46 (9H, s), 1.69–1.80 (3H, m), 1.89–2.03 (2H, m), 2.16–2.40 (5H, m), 2.28 (1H, d, J=2.4 Hz), 2.70–2.85 (4H, m), 3.33–3.51 (1H, m), 4.04–4.18 (3H, m), 5.04–5.17 (1H, m), 5.77 (2H, s), 6.24 (1H, d, J=15.1 Hz), 6.83 (1H, dd, J=15.1 and 6.6 Hz); MASS (m/z): 576 (M$^+$+1).

The following compound was obtained according to a similar manner to that of Example 108.

EXAMPLE 109

N-[(R)-1-[3-(1-tert-Butoxycarbonyl-4-piperidyl)-(E)-acryloyl]-3-piperidylcarbonyl]-β-alanine Pivaloyloxymethyl Ester IR (Film): 2960, 2930 2855, 1750, 1670, 1650, 1600 cm$^{-1}$; NMR (CDCl$_3$, δ): 1.21 (9H, s), 1.21–2.05 (8H, m), 1.46 (9H, s), 2.21–2.39 (2H, m), 2.58 (2H, t, J=6.1 Hz), 2.70–2.83 (2H, m), 3.23–3.78 (5H, m), 4.07–4.20 (3H, m), 5.76 (2H, d, J=2.4 Hz), 6.22 (1H, d, J=15.2 Hz), 6.65–6.79 (1H, m), 6.81 (1H, dd, J=15.2 and 6.7 Hz); MASS (m/z): 552 (M$^+$+1).

EXAMPLE 110

To a solution of N-[(R)-1-[3-(1-tert-butoxycarbonyl-4-piperidyl)-(E)-acryloyl]-3-piperidylcarbonyl]-2-hydroxymethyl-β-alanine (0.24 g) in ethyl acetate (2 ml) was added 4N HCl in ethyl acetate (1.3 ml) at 0° C., and the reaction mixture was stirred for 2 hours at room temperature. The precipitates were filtered and washed with diethyl ether to give N-[(R)-1-[3-(4-piperidyl)-(E)-acryloyl]-3-piperidylcarbonyl]-2-hydroxymethyl-β-alanine hydrochloride (0.17 g, 82.0%).

IR (KBr pellet): 3440, 2947, 2866, 1728, 1659 cm$^{-1}$; NMR (D$_2$O, δ): 1.40–1.83 (7H, m), 1.92–2.08 (4H, m), 2.40–2.69 (4H, m), 2.78–2.92 (2H, m), 2.99–3.29 (3H, m), 3.38–3.55 (3H, m), 3.78 (2H, d, J=5.9 Hz), 3.92–4.18 (1H, m), 4.25–4.37 (1H, m), 6.46 (1H, dd, J=15.8 Hz), 6.58–6.71 (1H, m); MASS (m/z): 368 (M$^+$ free+1).

The following compounds [Examples 111 to 124] were obtained according to a similar manner to that of Example 110.

EXAMPLE 111

N-[1-[3-(4-Piperidyl)-(E)-acryloyl]-3-piperidylcarbonyl]-3(S)-ethynyl-β-alanine Hydrochloride IR (KBr pellet): 2954, 2729, 2360, 2337, 1724, 1655 cm$^{-1}$; NMR (D$_2$O, δ): 1.52–1.75 (4H, m), 1.84–1.93 (2H, m), 2.01–2.07 (2H, m), 2.51–2.68 (2H, m), 2.74 (1H, d, J=2.3 Hz), 2.85 (2H, dd, J=7.0 and 2.9 Hz), 3.00–3.25 (3H, m), 3.40–3.51 (2H, m), 4.08–4.20 (1H, m), 4.39–4.49 (1H, m), 4.64–4.98 (3H, m), 6.46 (1H, d, J=15.6 Hz), 6.64 (1H, dd, J=15.6 and 6.2 Hz); MASS (m/z): 362 (M$^+$ free+1); $[\alpha]_D^{25}$=−37.97° (C=1.0, MeOH).

EXAMPLE 112

3-[(R)-1-[3-(4-Piperidyl)-(E)-acryloyl]-3-piperidylcarbonyl]aminobenzoic Acid Hydrochloride IR (KBr pellet): 2951, 2862, 2729, 1711, 1655 cm$^{-1}$; NMR (D$_2$O, δ): 1.50–2.10 (10H, m), 2.36–2.76 (2H, m), 2.91–3.70 (5H, m), 3.84–4.49 (2H, m), 6.46 (1H, dd, J=15.5 and 2.2 Hz), 6.56–6.72 (1H, m), 7.48 (1H, td, J=7.9 and 2.2 Hz), 7.66 (1H, d, J=8.3 Hz), 7.79 (1H, d, J=6.6 Hz), 8.01 (1H, d, J=1.8 Hz); MASS (m/z): 386 (M$^+$ free+1).

EXAMPLE 113

4-[(R)-1-[3-(4-Piperidyl)-(E)-acryloyl]-3-piperidylcarbonyl]aminobenzoic Acid Hydrochloride IR (KBr pellet): 3425, 2947, 2862, 2729, 1691, 1655 cm$^{-1}$; NMR (D$_2$O, δ): 1.47–2.10 (8H, m), 2.29–2.79 (3H, m), 2.89–4.46 (8H, m), 6.39–6.72 (2H, m), 7.56 (2H, d, J=8.7 Hz), 7.97 (2H, dd, J=8.8 and 2.1 Hz); MASS (m/z): 386 (M$^+$ free+1); $[\alpha]_D^{25}$=−34.70° (C=1.0, MeOH).

EXAMPLE 114

2-[(R)-1-[3-(4-Piperidyl)-(E)-acryloyl]-3-piperidylcarbonyl]aminobenzoic Acid Hydrochloride IR (KBr pellet): 3425, 2947, 2862, 2821, 2727, 1682, 1657 cm$^{-1}$; NMR (D$_2$O, δ): 1.51–2.16 (9H, m), 2.40–2.80 (2H, m), 2.95–3.50 (6H, m), 3.62–4.08 (2H, m), 6.44–6.69 (2H, m), 7.26–7.36 (1H, m), 7.53–7.66 (1H, m), 7.87–8.03 (2H, m); MASS (m/z): 386 (M$^+$ free+1). $[\alpha]D^{25}$=−7.53° (C=1.0, MeOH).

EXAMPLE 115

N-[(R)-1-[3-(4-Piperidyl)benzoyl]-3-piperidylcarbonyl]-3(S)-ethynyl-β-alanine

IR (KBr pellet): 2721, 1728, 1655, 1599, 1579 cm$^{-1}$; NMR (D$_2$O, δ): 1.32–1.47 (1H, m), 1.54–1.99 (8H, m), 2.33–2.46 (1H, m), 2.54–2.65 (3H, m), 2.80–3.07 (5H, m), 3.19 (1H, d, J=2.0 Hz), 3.30–3.40 (2H, m), 4.23–4.44 (1H, m), 4.73–4.87 (1H, m), 7.21–7.45 (4H, m), 8.49–8.57 (1H, m); MASS (m/z): 412 (M$^+$ free+1); $[\alpha]D^{25}$=−40.47° (C=1.0, MeOH).

EXAMPLE 116

N-[(R)-1-[4-(4-Piperidyl)benzoyl]-3-piperidylcarbonyl]-3(S)-ethynyl-β-alanine

IR (KBr pellet): 2929, 1728, 1649, 1605 cm$^{-1}$; NMR (D$_2$O, δ): 1.30–1.97 (9H, m), 2.25–2.41 (1H, m), 2.54–2.64 (2H, m), 2.82–3.08 (5H, m), 3.19 (1H, d, J=2.3 Hz), 3.29–3.41 (2H, m), 4.24–4.44 (1H, m), 4.75–4.87 (1H, m), 7.29 (2H, d, J=8.3 Hz), 7.35 (2H, d, J=8.3 Hz), 8.43–8.51 (1H, m), 8.95–9.11 (2H, br); MASS (m/z): 412 (M$^+$ free+1); $[\alpha]D^{25}$=49.77° (C=1.0, MeOH).

EXAMPLE 117

N-[(R)-1-[3-(4-Piperidyl)-(E)-acryloyl]-3-piperidylcarbonyl]-3(S)-ethynyl-β-alanine Phenethyl Ester Hydrochloride IR (KBr pellet): 3412, 3278, 3028, 2951, 2864, 2725, 1734, 1655 cm$^{-1}$; NMR (D$_2$O, δ): 1.46–2.27 (9H, m), 2.41–3.43 (12H, m), 3.56–3.72 (2H, m), 4.10–4.64 (4H, m), 6.53–6.88 (2H, m), 7.25–7.35 (5H, m); MASS (m/z): 466 (M$^+$ free+1).

EXAMPLE 118

N-[(R)-1-[3-(4-Piperidyl)-(E)-acryloyl]-3-piperidylcarbonyl]-β-alanine n-butyl Ester Hydrochloride IR (KBr pellet): 3415, 3059, 2956, 2870, 2725, 1730, 1653 cm$^{-1}$; NMR (D$_2$O, δ): 0.90 (3H, t, J=7.3 Hz), 1.25–1.85 (10H, m), 1.93–2.09 (3H, m), 2.39–2.69 (2H, m), 2.57 (2H, t, J=6.4 Hz), 2.92–3.27 (2H, m), 3.10 (2H, td, J=12.7 and 2.8 Hz), 3.32–3.53 (4H, m), 3.93–4.40 (2H, m), 4.12 (2H, t, J=6.5 Hz), 6.48 (1H, d, J=15.5 Hz), 6.66 (1H, dd, J=15.5 and 5 6.2 Hz); MASS (m/z): 394 (M$^+$ free+1).

EXAMPLE 119

N-[(R)-1-[3-(4-Piperidyl)-(E)-acryloyl]-3-piperidylcarbonyl]-β-alanine 1-(cyclohexyloxycarbonyl)ethyl Ester Hydrochloride IR (KBr pellet): 3425, 3377, 3271, 3070, 2941, 2862, 2810, 2729, 1757, 1653 cm$^{-1}$; NMR (D$_2$O, δ): 1.19–2.08 (18H, m), 1.50 (3H, d, J=5.3 Hz), 2.34–2.62 (5H, m), 2.80–2.93 (1H, m), 3.03–3.15 (3H, m), 3.25–3.63 (4H, m), 4.00–4.49 (2H, m), 4.56–4.66 (1H, m), 6.49 (1H, d, J=15.6 Hz), 6.66 (1H, dd, J=15.6 and 6.2 Hz), 6.61–6.71 (1H, m); MASS (m/z): 508 (M$^+$ free+1).

EXAMPLE 120

(–)-N-[(R)-1-[3-(4-Piperidyl)propanoyl]-3-piperidylcarbonyl]-3-cyclopropyl-β-alanine Hydrochloride IR (KBr pellet): 3444, 3392, 3076, 3008, 2949, 2866, 2731, 1732, 1716, 1649, 1622 cm$^{-1}$; NMR (D$_2$O, δ): 0.24–0.34 (2H, m), 0.93–1.09 (1H, m), 1.36–1.84 (9H, m), 1.91–2.03 (3H, m), 2.32–2.82 (9H, m), 2.92–3.03 (3H, m), 3.11–3.46 (2H, m), 3.53–3.65 (1H, m), 3.76–3.93 (1H, m), 4.08–4.27 (1H, m); MASS (m/z): 380 (M$^+$ free+1).

EXAMPLE 121

3-[(R)-1-[3-(4-Piperidyl)propanoyl]- 3-piperidylcarbonyl]aminobenzoic Acid Hydrochloride IR (KBr pellet): 3444, 2949, 2866, 2731, 1713, 1684, 1653, 1614 cm$^{-1}$; NMR (D$_2$O, δ): 1.23–1.69 (7H, m), 1.81–2.11 (6H, m), 2.42–2.75 (3H, m), 2.85–3.31 (3H, m), 3.37–3.56 (2H, m), 3.79–4.36 (2H, m), 7.48 (1H, td, J=7.9 and 2.9 Hz), 7.64–7.69 (1H, m), 7.76–7.80 (1H, m), 8.02 (1H, s); MASS (m/z): 388 (M$^+$+1).

EXAMPLE 122

4-[(R)-1-[3-(4-Piperidyl)propanoyl]-3-piperidylcarbonyl]aminobenzoic Acid Hydrochloride IR (KBr pellet): 3101, 2947, 2862, 1691 cm$^{-1}$; NMR (D$_2$O, δ): 1.28–1.69 (6H, m), 1.77–2.09 (5H, m), 2.40–2.78 (4H, m), 2.84–2.98 (2H, m), 3.11–3.46 (4H, m), 3.78–4.31 (2H, m), 7.58 (2H, dd, J=8.7 and 1.4 Hz), 8.00 (2H, dd, J=8.7 and 1.8 Hz); MASS (m/z): 388 (M$^+$ free+1); [α]$_D^{25}$=–24.4° (C=1.0, MeOH).

EXAMPLE 123

2-[(R)-1-[3-(4-Piperidyl)propanoyl]-3-piperidylcarbonyl]aminobenzoic Acid Hydrochloride IR (KBr pellet): 3417, 2947, 2862, 2731, 1686, 1609 cm$^{-1}$; NMR (D$_2$O, δ): 1.28–2.09 (11H, m), 2.49–2.76 (2H, m), 2.86–3.49 (6H, m), 3.51–4.40 (4H, m), 7.30 (1H, t, J=7.5 Hz), 7.62 (1H, t, J=7.9 Hz), 7.89–30 8.02 (2H, m); MASS (m/z): 388 (M$^+$ free+1); [α]$_D^{25}$=–8.85° (C=1.0, MeOH).

EXAMPLE 124

N-[(R)-1-[3-(4-Piperidyl)propanoyl]- 3-piperidylcarbonyl]-2-hydroxymethyl-β-alanine Hydrochloride IR (KBr pellet): 3419, 3064, 2945, 2866, 1726, 1643, 1620 cm$^{-1}$; NMR (D$_2$O, δ): 1.36–2.09 (13H, m), 2.38–2.53 (3H, m), 2.81–3.03 (4H, m), 3.12–3.52 (5H, m), 3.78 (2H, d, J=5.9 Hz), 3.86–3.93 (1H, m), 4.11–4.30 (1H, m); MASS (m/z): 370 (M$^+$+1).

EXAMPLE 125

To a solution of N-[(R)-1-[3-(1-tert-butoxycarbonyl-4-piperidyl)-(E)-acryloyl]-3-piperidylcarbonyl]-3(R)-(3,4-dimethoxyphenethyl)-β-alanine (1.33 g) in ethyl acetate (10 ml) was added 4N HCl in 1,4-dioxane (5.53 ml) at 0° C., and the reaction mixture was stirred for 3 hours at room temperature. The precipitates were filtered, washed with diethyl ether and resolved in water, neutralized with saturated aqueous NaHCO$_3$, desalted by using the resin of HP-20 eluting with isopropanol:H$_2$O=(1:1), then freeze-dried to give N-[(R)-1-[3-(4-piperidyl)-(E)-acryloyl]-3-piperidylcarbonyl]-3(R)-(3,4-dimethoxyphenethyl)-β-alanine as a white powder (0.88 g, 79.4%).

IR (Nujol): 3400, 1635, 1600 cm$^{-1}$; NMR (D$_2$O, δ): 1.41–2.05 (10H, m), 2.18–2.68 (4H, m), 2.40 (2H, d, J=7.3 Hz), 2.97–3.12 (4H, m), 3.23–3.50 (3H, m), 3.82 (3H, s), 3.85 (3H, s), 3.87–4.20 (3H, m), 6.38–6.68 (2H, m), 6.80–6.98 (3H, m); MASS (m/z): 502 (M$^+$+1). [α]$_D^{20}$=–48.7° (C=1.0, MeOH).

The following compounds [Examples 126 to 143] were obtained according to a similar manner to that of Example 125.

EXAMPLE 126

N-[(R)-1-[3-(4-Piperidyl)-(E)-acryloyl]-3-piperidylcarbonyl]-3(R)-(4-methoxyphenethyl)-β-alanine IR (Nujol): 3445, 1645, 1600 cm$^{-1}$; NMR (D$_2$O, δ): 1.41–2.05 (10H, m), 2.18–2.68 (4H, m), 2.40 (2H, d, J=7.3 Hz), 2.97–3.12 (4H, m), 3.23–3.50 (3H, m), 3.82 (3H, s), 3.85 (3H, s), 3.87–4.20 (3H, m), 6.38–6.68 (2H, m), 6.80–6.98 (3H, m); MASS (m/z): 472 (M$^+$+1); Elemental Analysis Calcd. for C$_{26}$H$_{37}$N$_3$O$_5$.0.3H$_2$O: C, 65.47, H, 7.94, N, 8.81; Found: C, 65.36, H, 7.92, N, 8.92.

EXAMPLE 127

N-[(R)-1-[3-(4-Piperidyl)-(E)-acryloyl]-3-piperidylcarbonyl]-3(S)-methoxymethyl-β-alanine IR (KBr pellet): 2939, 2862, 1652 cm$^{-1}$; NMR (D$_2$O, δ): 1.45–1.88 (6H, m), 1.93–2.12 (3H, m), 2.26–2.67 (4H, m), 2.92–3.23 (3H, m), 3.36 (3H, s), 3.31–3.49 (4H, m), 3.90–4.20 (2H, m), 4.27–4.39 (2H, m), 6.47 (1H, d, J=15.7 Hz), 6.59–6.72 (1H, m); MASS (m/z): 382 (M$^+$+1).

EXAMPLE 128

(−)-N-[(R)-1-[3-(4-Piperidyl)-(E)-acryloyl]-3-piperidylcarbonyl]-3-cyclopropyl-β-alanine IR (KBr pellet): 3444, 3392, 3082, 3012, 2949, 2862, 1653 cm$^{-1}$; NMR (D$_2$O, δ): 0.20–0.32 (2H, m), 0.39–0.59 (2H, m), 0.93–1.01 (1H, m), 1.45–2.08 (9H, m), 2.40–2.67 (4H, m), 2.96–3.65 (7H,.m), 3.88–4.27 (2H, m), 6.48 (1H, d, J=15.7 Hz), 6.65 (1H, dt, J=15.7 and 5.89 Hz); MASS (m/z): 378 (M$^+$+1). [α]$_D^{20}$=−73.6° (C=1.0, MeOH); Elemental Analysis Calcd. for C$_{20}$H$_{31}$N$_3$O$_4$.0.2H$_2$O: C, 58.09, H, 8.53, N, 10.16; Found: C, 58.32, H, 8.45, N, 10.16.

(+)-N-[(R)-1-[3-(4-Piperidyl)-(E)-acryloyl]-3-piperidylcarbonyl]-3-cyclopropyl-β-alanine IR (KBr pellet): 3471, 3412, 3365, 3802, 3007, 2949, 2862, 1653 cm$^{-1}$; NMR (D$_2$O, δ): 0.18–0.35 (2H, m), 0.38–0.58 (2H, m), 0.90–1.08 (1H, m), 1.42–2.12 (9H, m), 2.33–2.69 (4H, m), 3.01–3.66 (7H, m), 4.00–4.32 (2H, m), 6.47 (1H, d, J=15.6 Hz), 6.59–6.72 (1H, m); MASS (m/z): 378 (M$^+$+1); [α]$_D^{20}$=−38.5° (C=1.0, MeOH); Elemental Analysis Calcd. for C$_{20}$H$_{31}$N$_3$O$_4$.2.3H$_2$O: C, 57.34, H, 8.57, N, 10.03; Found: C, 57.26, H, 8.73, N, 9.86.

EXAMPLE 129

N-[(R)-1-[3-(4-Piperidyl)-(E)-acryloyl]-3-piperidylcarbonyl]-3(R)-ethynyl-β-alanine IR (KBr pellet): 3415, 3271, 3051, 2947, 2860, 2748, 1655 cm$^{-1}$; NMR (D$_2$O, δ): 1.41–1.87 (6H, m), 1.95–2.09 (3H, m), 2.39–2.70 (5H, m), 3.02–3.29 (4H, m), 3.40–3.50 (3H, m), 3.92–4.34 (2H, m), 6.47 (1H, d, J=15.6 Hz), 6.59–6.71 (1H, m); MASS (m/z): 362 (M$^+$+1); [α]$_D^{25}$=−29.27° (C=1.0, MeOH); Elemental Analysis Calcd. for C$_{19}$H$_{27}$N$_3$O$_4$.1.5H$_2$O: C, 58.75, H, 7.78, N, 10.82; Found: C, 58.79, H, 7.96, N, 10.56.

EXAMPLE 130

N-[(S)-1-[3-(4-Piperidyl)-(E)-acryloyl]-3-piperidylcarbonyl]-3(S)-ethynyl-β-alanine IR (KBr pellet): 3444, 3275, 2947, 2862, 1653 cm$^{-1}$; NMR (D$_2$O, δ): 1.43–1.85 (6H, m), 1.93–2.10 (3H, m), 2.42–2.70 (5H, m), 3.03–3.51 (7H, m), 3.90–4.36 (2H, m), 6.48 (1H, d, J=15.6 Hz), 6.59–6.72 (1H, m); MASS (m/z): 362 (M$^+$+1); [α]$_D^{25}$=25.4° (C=1.0, MeOH); Elemental Analysis Calcd. for C$_{19}$H$_{27}$N$_3$O$_4$.1.9H$_2$O: C, 57.68, H, 7.85, N, 10.62; Found: C, 57.61, H, 8.10, N, 10.41.

N-[(S)-1-[3-(4-Piperidyl)-(E)-acryloyl]-3-piperidylcarbonyl]-3(R)-ethynyl-β-alanine IR (KBr pellet): 3439, 3259, 3049, 2945, 2860, 1655 cm$^{-1}$; NMR (D$_2$O, δ): 1.41–1.89 (6H, m), 1.99–2.09 (3H, m), 2.39–2.67 (5H, m), 3.01–3.15 (3H, m), 3.17–3.50 (4H, m), 3.92–4.37 (2H, m), 6.46 (1H, d, J=15.7 Hz), 6.59–6.67 (1H, m); MASS (m/z): 362 (M$^+$+1); [α]$_D^{25}$=79.23° (C=1.0, MeOH); Elemental Analysis Calcd. for C$_{19}$H$_{27}$N$_3$O$_4$.1.6H$_2$O: C, 58.21, H, 7.82, N, 10.72; Found: C, 58.35, H, 8.23, N, 10.48.

EXAMPLE 131

N-[(R)-1-[3-(4-Piperidyl)-(E)-acryloyl]-3-piperidylcarbonyl]-2-benzyloxymethyl-β-alanine IR (KBr pellet): 3514, 3433, 3317, 3265, 2939, 2860, 1657 cm$^{-1}$; NMR (D$_2$O, δ): 1.37–2.09 (8H, m), 2.26–2.43 (1H, m), 2.45–2.63 (1H, m), 2.69–2.81 (1H, m), 2.85–3.28 (4H, m), 3.35–3.50 (4H, m), 3.56–3.78 (2H, m), 3.85–4.00 (1H, m), 4.08–4.33 (2H, m), 4.55 (2H, s), 6.35–6.70 (2H, m), 7.44 (5H, s); MASS (m/z): 458 (M$^+$+1).

EXAMPLE 132

N-[(R)-1-[3-(4-Piperidyl)-(E)-methacryloyl]-3-piperidylcarbonyl]-3(S)-ethynyl-β-alanine IR (Nujol): 1750, 1670 cm$^{-1}$; NMR (D$_2$O, δ): 1.05–1.90 (8H, m), 1.56 (3H, s), 2.05–3.05 (8H,m), 2.37 (1H, d, J=2.2 Hz), 3.05–3.25 (2H, m), 3.35–3.80 (2H, m), 3.80–4.05 (1H, m), 5.13 (1H, d, J=7.6 Hz); MASS (m/z): 376 (M$^+$+1).

EXAMPLE 133

N-[(R)-1-[3-(4-Piperidyl)-(E)-acryloyl]-3-piperidylcarbonyl]-3,3-dimethyl-β-alanine NMR (CDCl$_3$, δ): 1.25–2.15 (12H, m), 1.39 (6H, s), 2.20–2.60 (5H, m), 2.75–3.10 (3H, m), 3.10–3.55 (3H, m), 3.75–4.00 (1H, m), 4.05–4.35 (1H, m); MASS (m/z): 368 (M$^+$+1).

EXAMPLE 134

N-[(R)-1-[2-(4-Piperidyl)-(1R*,2S*)-cyclopropan-1-yl-carbonyl]-3-piperidylcarbonyl]-3(S)-ethynyl-β-alanine IR (Nujol): 1600 cm$^{-1}$; NMR (D$_2$O, δ): 0.45–0.70 (1H, m), 0.70–1.05 (3H, m), 1.05–1.85 (9H, m), 1.85–2.45 (4H, m), 2.45–2.75 (3H, m), 2.75–3.05 (1H, m), 3.05–3.25 (3H, m), 3.70–4.10 (2H, m); MASS (m/z): 376 (M$^+$+1).

EXAMPLE 135

N-[(R)-3-(4-Piperidyl)-3-methyl-(E)-acryloyl]- 3-piperidylcarbonyl]-3(S)-ethynyl-β-alanine IR (Nujol): 1640 cm$^{-1}$; NMR (D$_2$O, δ): 1.35–2.15 (9H, m), 1.76 (3H, s), 2.20–2.55 (2H, m), 2.55–2.75 (3H, m), 2.85–3.60 (6H, m), 3.65–4.00 (1H, m), 4.05–4.35 (1H, m), 5.88 (1H, m); MASS (m/z): 376 (M$^+$+1).

EXAMPLE 136

N-[(R)-1-[3-(4-Piperidyl)-(E)-acryloyl]-3-piperidylcarbonyl]-3(S)-ethynyl-β-alanine Ethyl Ester IR (KBr pellet): 3427, 3269, 3049, 2941, 2862, 2742, 1732, 1655 cm$^{-1}$; NMR (D$_2$O, δ): 1.10 (3H, t, J=7.2 Hz), 1.32–1.68 (6H, m), 1.75–1.89 (3H, m), 2.23–2.54 (3H, m), 2.59–3.14 (6H, m), 3.23–3.30 (3H, m), 3.37–4.19 (2H, m), 4.03 (2H, q, J=7.2 Hz), 4.76–4.86 (1H, m), 6.30 (1H, d, J=15.6 Hz), 6.43–6.57 (1H, m); MASS (m/z): 390 (M$^+$+1); Elemental Analysis Calcd. for C$_{21}$H$_{31}$N$_3$O$_4$.2.7H$_2$O: C, 57.57, H, 8.37, N, 9.59; Found: C, 57.89, H, 8.13, N, 9.19.

EXAMPLE 137

N-[(R)-1-[3-(4-Piperidyl)-(E)-acryloyl]-3-piperidylcarbonyl]-3(S)-ethynyl-β-alanine n-butyl Ester NMR (D$_2$O, δ): 0.92 (3H, t, J=7.2 Hz), 1.24–1.41 (5H, m), 1.59–1.76 (2H, m), 2.18–2.30 (2H, m), 2.58–2.82 (5H, m), 3.11–3.18 (2H, m), 3.83 (2H, d, J=7.2 Hz), 5.16–5.19 (1H, m), 6.15 (1H, d, J=15.4 Hz), 6.25–6.40 (1H, m); MASS (m/z): 418 (M$^+$+1).

EXAMPLE 138

N-[(R)-1-[3-(4-Piperidyl)propanoyl]- 3-piperidylcarbonyl]-2-benzyloxymethyl-β-alanine IR (KBr pellet): 3398, 2937, 2862, 1635 cm$^{-1}$; NMR (D$_2$O, δ): 1.25–2.00 (12H, m), 2.24–2.50 (3H, m), 2.69–3.03 (4H, m), 3.08–3.32 (1H, m), 3.32–3.47 (4H, m), 3.56–3.88 (3H, m), 4.11–4.27 (1H, m), 4.50 (2H, s), 7.42 (5H, s); MASS (m/z): 460 (M$^+$+1).

EXAMPLE 139

N-[(R)-1-[3-(4-Piperidyl)propanoyl]-3-piperidylcarbonyl]-3(S)-methoxymethyl-β-alanine IR (KBr pellet): 3074, 2935, 2862, 1624 cm$^{-1}$; NMR (D$_2$O, δ): 1.31–1.86 (9H, m), 1.93–2.05 (3H, m), 2.26–2.54 (5H, m), 2.76–3.05 (3H, m), 3.15–3.50 (2H, m), 3.37 (3H, s), 3.48 (2H, d, J=6.3 Hz), 3.79–3.97 (1H, m), 4.15–4.44 (2H, m); MASS (m/z): 384 (M$^+$+1).

EXAMPLE 140

N-[(R)-1-[3-(4-Piperidyl)propanoyl]-3-piperidylcarbonyl]-2-benzoylaminomethyl-β-alanine IR (KBr pellet): 3381, 3311, 3064, 2937, 2862, 1643 cm$^{-1}$; NMR (D$_2$O, δ): 1.27–1.99 (12H, m), 2.35–2.57 (3H, m), 2.72–3.08 (4H, m), 3.13–3.49 (5H, m), 3.56 (2H, d, J=6.7 Hz), 3.80–4.31 (3H, m), 7.50–7.63 (3H, m), 7.75–7.79 (2H, m); MASS (m/z): 473 (M$^+$+1).

EXAMPLE 141

N-[(R)-1-[3-(4-Piperidyl)propanoyl]-3-piperidylcarbonyl]-2-acetylaminomethyl-β-alanine IR (KBr pellet): 3444, 3086, 2939, 2862, 1647 cm$^{-1}$; NMR (D$_2$O, δ): 1.30–1.94 (11H, m), 2.06 (3H, s), 2.36–2.70 (4H, m), 2.77–3.04 (3H, m), 3.13–3.45 (7H, m), 3.83–4.00 (2H, m), 4.15–4.38 (2H, m); MASS (m/z): 411 (M$^+$+1).

EXAMPLE 142

N-[(R)-1-[3-(4-Piperidyl)propanoyl]-3-piperidylcarbonyl]-3,3-dimethyl-β-alanine

NMR (D$_2$O, δ): 1.25–1.90 (8H, m), 1.39 (6H, s), 1.90–2.10 (3H, m)) 2.20–2.65 (5H, m), 2.70–3.10 (3H, m), 3.10–3.55 (3H, m), 3.70–4.05 (1H, m), 4.15–4.40 (1H, m); MASS (m/z): 368 (M$^+$+1).

EXAMPLE 143

N-[(R)-1-[3-(1,2,3,6-Tetrahydro-4-pyridyl)propanoyl]-3-piperidylcarbonyl]-3(S)-ethynyl-β-alanine Ethyl Ester NMR (D$_2$O, δ): 1.24 (3H, t, J=7.1 Hz), 1.55–1.94 (5H, m), 2.24–2.65 (5H, m), 2.74 (1H, d, J=2.4 Hz), 2.80–3.00 (6H, m), 3.30–3.42 (3H, m), 3.64 (1H, br), 3.83–3.90 (1H, m), 4.12–4.28 (1H, m), 4.17 (2H, q, J=7.1 Hz), 5.48 (1H, br); MASS (m/z): 390 (M$^+$+1).

EXAMPLE 144

To a solution of N-[(R)-1-[3-(1-tert-butoxycarbonyl-4-piperidyl)-(E)-acryloyl]-3-piperidylcarbonyl]-3(S)-ethynyl-β-alanine n-pentyl ester (0.65 g) in ethyl acetate (6 ml) was added 4N HCl in 1,4-dioxane (3.06 ml) at 0° C., and the reaction mixture was stirred for 2 hours at room temperature. The precipitates were filtered, washed with ether and dissolved in water, neutralized with saturated aqueous NaHCO$_3$, desalted by using the resin of HP-20 eluting with isopropanol:H$_2$O=(1:1), and 1N aqueous HCl was added, then freeze-dried to give N-[(R)-1-[3-(4-piperidyl)-(E)-acryloyl]-3(R)-piperidylcarbonyl]- 3(S)-ethynyl-β-alanine n-pentyl ester hydrochloride (184 mg, 32.2%).

IR (KBr pellet): 3417, 3294, 3035, 2958, 2939, 2864, 2727, 1734, 1655 cm$^{-1}$; NMR (D$_2$O, δ): 0.76–0.83 (3H, m), 1.18–1.32 (4H, m), 1.39–1.76 (7H, m), 1.88–2.00 (3H, m), 2.31–2.58 (2H, m), 2.67 (1H, d, J=2.4 Hz), 2.75–3.20 (4H, m), 3.29–3.42 (3H, m), 3.80–4.27 (2H, m), 4.07 (2H, d, J=6.5 Hz), 4.55–4.93 (2H, m), 6.38 (1H, d, J=15.2 Hz), 6.51–6.63 (1H, m); MASS (m/z): 432 (M$^+$ free+1).

The following compound was obtained according to a similar manner to that of Example 144.

EXAMPLE 145

N-[(R)-1-[3-(4-Piperidyl)propanoyl]-3-piperidylcarbonyl]-2(S)-acetylamino-β-alanine n-pentyl Ester Hydrochloride IR (KBr pellet): 3439, 3390, 3359, 3064, 2956, 2941, 2864, 2731, 1738, 1653, 1622 cm$^{-1}$; NMR (D$_2$O, δ): 0.85–0.93 (3H, m), 1.30–1.38 (3H, m), 1.43–1.88 (9H, m), 1.95–2.05 (6H, m), 2.34–2.54 (2H, m), 2.85–3.08 (2H, m), 3.14–3.46 (8H, m), 4.10–4.38 (2H, m), 4.54–5.01 (7H, m); MASS (m/z): 467 (M$^+$ free+1).

EXAMPLE 146

A mixture of N-[(R)-1-[3-(1-benzyloxycarbonyl-4-piperidyl)propanoyl]-3-piperidylcarbonyl]-2(S)-acetylamino-β-alanine (0.5 g) 1N HCl (0.94 ml) and 10% Pd—C (0.1 g) in tetrahydrofuran (5 ml) was hydrogenated at atmospheric pressure for 2 hours. After the catalyst was removed by filtration, the filtrate was concentrated in vacuo. The residue was resolved in water, and neutralized with saturated aqueous NaHCO$_3$, desalted by using the resin of HP-20 eluting with isopropanol:H$_2$O=(1:1), then freeze-dried to give N-[(R)-1-[3-(4-piperidyl)propanoyl]-3-piperidylcarbonyl]-2(S)-acetylamino-β-alanine (0.34 g, 91.0%).

IR (KBr pellet): 2943, 2862, 1608 cm$^{-1}$; NMR (D$_2$O, δ): 1.31–1.88 (8H, m), 1.94–2.03 (4H, m), 2.03 (3H, s), 2.39–2.54 (3H, m), 2.80–3.05 (3H, m), 3.19–3.48 (5H, m), 3.63–3.74 (1H, m), 3.81–3.95 (1H, m), 4.18–4.34 (1H, m), 4.35–4.41 (1H, m); Elemental Analysis Calcd. for C$_{19}$H$_{32}$N$_4$O$_5$.1.6H$_2$O: C, 53.66, H, 8.34, N, 13.17; Found: C, 53.63, H, 8.56, N, 13.03.

The following compounds [Examples 147 to 148] were obtained according to a similar manner to that of Example 146.

EXAMPLE 147

N-[(R)-1-[3-(4-Piperidyl)propanoyl]-3-piperidylcarbonyl]-2(S)-benzoylamino-β-alanine IR (KBr pellet): 2943, 2862, 1643 cm$^{-1}$; NMR (DMSO-d, δ): 1.20–1.96 (13H, m), 2.22–2.45 (3H, m), 2.70–3.02 (3H, m), 3.08–3.27 (1H, m), 3.35–3.46 (2H, m), 3.58–3.80 (3H, m), 4.13–4.19 (1H, m), 4.57–4.70 (1H, m), 7.51–7.70 (3H, m), 7.78–7.86 (2H, m); Elemental Analysis Calcd. for C$_{24}$H$_{34}$N$_4$O$_5$.1.1H$_2$O: C, 60.26, H, 7.63, N, 11.71; Found: C, 60.22, H, 7.64, N, 11.65.

EXAMPLE 148

N-[(R)-1-[3-(4-Piperidyl)propanoyl]-3-piperidylcarbonyl]-2(S)-(4-methoxybenzoylamino)-β-alanine IR (KBr pellet): 2943, 2860, 1632, 1608 cm$^{-1}$; NMR (DMSO-d$_6$, δ): 1.19–1.59 (7H, m), 1.65–2.00 (6H, m), 2.20–2.29 (1H, m), 2.37–2.45 (2H, m), 2.71–3.04 (3H, m), 3.12–3.25 (1H, m), 3.35–3.49 (2H, m), 3.60–3.82 (3H, m), 3.89 (3H, s), 4.08–4.20 (1H, m), 4.55–4.66 (1H, m), 7.09 (2H, dd, J=8.9 and 2.9 Hz), 7.80 (2H, dd, J=8.8 and 1.9 Hz); Elemental Analysis Calcd. for C$_{25}$H$_{36}$N$_4$O$_6$·1.4H$_2$O: C, 58.44, H, 7.61, N, 10.90; Found: C, 58.43, H, 7.73, N, 10.85.

EXAMPLE 149

A solution of 3-[(R)-1-[3-(4-piperidyl)propanoyl]-3-piperidylcarbonyl]aminobenzoic acid hydrochloride (1 g) was neutralized by saturated aqueous NaHCO$_3$, desalted by using the resin of HP-20 eluting with H$_2$O: isopropanol= (1:1), then freeze-dried to give 3-[(R)-1-[3-(4-piperidyl)propanoyl]-3-piperidylcarbonyl]aminobenzoic acid (732 mg 80.1%).

IR (KBr pellet): 2860, 1678, 1616 cm$^{-1}$; NMR (D$_2$O, δ): 1.20–1.69 (6H, m), 1.77–2.09 (5H, m), 2.32–2.50 (2H, m), 2.56–2.94 (3H, m), 3.14–3.38 (4H, m), 3.53–3.93 (2H, m), 4.16–4.23 (1H, m), 7.47 (1H, t, J=7.8 Hz), 7.62–7.72 (2H, m), 7.84–7.87 (1H, m); MASS (m/z): 388 (M$^+$+1); [α]$_D^{25}$=−18.63° (C=1.0, MeOH); Elemental Analysis Calcd. for C$_{21}$H$_{29}$N$_3$O$_4$·1.7H$_2$O: C, 60.33, H, 7.81, N, 10.05; Found: C, 60.42, H, 8.35, N, 9.97.

The following compounds [Examples 150 to 152] were obtained according to a similar manner to that of Example 149.

EXAMPLE 150

3-[(R)-1-[3-(4-Piperidyl)-(E)-acryloyl]-3-piperidylcarbonyl]aminobenzoic Acid

IR (KBr pellet): 2860, 1676, 1655, 1608 cm$^{-1}$; NMR (D$_2$O, δ): 1.35–1.96 (8H, m), 2.26–2.76 (3H, m), 2.87–3.21 (3H, m), 3.28–3.53 (2H, m), 3.68–3.98, 4.38–4.44 (total 3H, m), 6.41 (1H, dd, J=15.4 and 4.8 Hz), 6.60 (1H, td, J=15.4 and 6.1 Hz), 7.46 (1H, t, J=7.9 Hz), 7.62–7.71 (2H, m), 7.77–7.84 (1H, m); MASS (m/z): 386 (M$^+$+1); [α]$_D^{25}$=−19.97° (C=1.0, MeOH); Elemental Analysis Calcd. for C$_{21}$H$_{27}$N$_3$O$_4$·1.9H$_2$O: C, 60.10, H, 7.40, N, 10.01; Found: C, 60.05, H, 7.73, N, 9.85.

EXAMPLE 151

4-[(R)-1-[3-(4-Piperidyl)-(E)-acryloyl]-3-piperidylcarbonyl]aminobenzoic Acid

IR (Nujol): 1660, 1650, 1600 cm$^{-1}$; NMR (D$_2$O, δ): 1.36–1.74 (4H, m), 1.83–2.09 (4H, m), 2.19–2.34 (1H, m), 2.50–2.70 (1H, m), 2.77–3.49 (6H, m), 3.59–3.68 (1H, m), 3.81–4.00 (2H, m), 6.44–6.60 (2H, m), 7.51 (2H, d, J=8.5 Hz), 7.88 (2H, d, J=8.6 Hz); MASS (m/z): 386 (M$^+$+1); [α]$_D^{25}$=−46.0° (C=0.2, MeOH); Elemental Analysis Calcd. for C$_{21}$H$_{27}$N$_3$O$_4$·2.4H$_2$O: C, 58.84, H, 7.48, N, 9.80; Found: C, 58.90, H, 7.66, N, 9.61.

EXAMPLE 152

4-[(R)-1-[3-(4-Piperidyl)propanoyl]-3-piperidylcarbonyl]aminobenzoic Acid

IR (KBr pellet): 3477, 3051, 2943, 2862, 1680, 1624, 1603 cm$^{-1}$; NMR (D$_2$O, δ): 1.27–1.73 (6H, m), 1.81–2.10 (5H, m), 2.45–2.54 (2H, m), 2.72–2.93 (3H, m), 3.29–3.54 (4H, m), 3.69–4.20 (3H, m), 7.54 (2H, d, J=8.6 Hz), 7.89 (2H, d, J=8.6 Hz); MASS (m/z): 388 (M$^+$+1); [α]$_D^{25}$=−28.8° (C=1.0, MeOH); Elemental Analysis Calcd. for C$_{21}$H$_{29}$N$_3$O$_4$·2.1H$_2$O: C, 59.31, H, 7.87, N, 9.88; Found: C, 59.21, H, 8.20, N, 9.72.

EXAMPLE 153

To a solution of N-[(R)-1-[3-(4-piperidyl)-(E)-acryloyl]-3-piperidylcarbonyl]-2(S)-trifluoroacetylamino-β-alanine trifluoroacetate in water (4 ml) was added Pd/C (10% dry, 16 mg) and the mixture was stirred at room temperature under hydrogen at atmospheric pressure for 4 hours. Catalyst was filtered off and filtrate was evaporated in vacuo to give N-[(R)-1-[3-(4-piperidyl)propanoyl]-3-piperidylcarbonyl]-2(S)-trifluoroacetylamino-β-alanine trifluoroacetate as a colorless oil (45 mg, 54.9%).

IR (Neat): 1720 cm$^{-1}$; NMR (D$_2$O, δ): 1.20–2.15 (11H, m), 2.35–2.65 (3H, m), 2.45–3.10 (3H, m), 3.05–3.30 (1H, m), 3.30–3.50 (2H, m), 3.60–4.00 (3H, m), 4.05–4.40 (1H, m), 4.50–4.70 (1H, m);

The following compounds [Examples 154 to 155] were obtained according to a similar manner to that of Example 153.

EXAMPLE 154

N-[(R)-1-[3-(4-Piperidyl)propanoyl]-2(S)-[4-trifluoromethyl)benzoylamino]-β-alanine IR (Nujol): 1610 cm$^{-1}$; NMR (D$_2$O, δ): 1.20–2.10 (11H, m), 2.20–2.60 (3H, m), 2.65–3.55 (6H, m), 3.55–3.95 (3H, m), 4.00–4.25 (1H, m), 4.50–4.75 (2H, m), 7.84–7.97 (4H, m); MASS (m/z): 527 (M$^+$+1).

EXAMPLE 155

N-[(R)-1-[3-(4-Piperidyl)propanoyl]-3-piperidylcarbonyl]-3(S)-trifluoroacetylaminomethyl)-β-alanine Trifluoroacetate IR (Nujol): 1710 cm$^{-1}$; NMR (D$_2$O, δ): 1.20–2.05 (12H, m), 2.25–2.85 (6H, m), 2.85–3.10 (3H, m), 3.10–3.55 (5H, m), 3.70–3.95 (1H, m), 4.05–4.30 (1H, m), 4.30–4.60 (1H, m); MASS (m/z): 465 (M$^+$+1).

EXAMPLE 156

To a stirred solution of N-[(R)-1-[3-(4-piperidyl)-(E)-acryloyl]-3-piperidylcarbonyl]-2(S)-trifluoroacetylamino-β-alanine ethyl ester (334 mg, 0.58 mmol) in ethyl acetate (1.5 ml) was added a solution of 4N-hydrogen chloride in ethyl acetate (1.0 ml, 4 mmol). After the solution was stirred for 2 hours at ambient temperature, the solvent was evaporated in vacuo. The residue was dissolved in 0.1M phosphate buffer (pH=7.3, 200 ml). To the solution was added Porcine liver esterase (0.5 ml), and the solution was stirred for 7 days at ambient temperature. Solvent was evaporated, and the residue was purified by HPLC to give N-[(R)-1-[3-(4-piperidyl)-(E)-acryloyl]-3-piperidylcarbonyl]-2(S)-trifluoroacetylamino-β-alanine trifluoroacetate as a colorless oil (220 mg, 67.5%).

IR: 1720 cm$^{-1}$; NMR (D$_2$O, δ): 1.35–1.90 (5H, m), 1.90–2.15 (3H, m), 2.35–2.70 (2H, m), 2.80–3.15 (3H, m), 3.15–3.40 (1H, m), 3.40–3.55 (2H, m), 3.60–4.05 (4H, m), 4.05–4.45 (1H, m), 6.49 (1H, d, J=15.6 Hz), 6.55–5 6.75 (1H, m);

The following compounds [Examples 157 to 158] were obtained according to a similar manner to that of Example 156.

EXAMPLE 157

N-[(R)-1-[3-(3-Azetidinyl)-(E)-acryloyl]-3-piperidylcarbonyl]-3(S)-ethynyl-β-alanine Trifluoroacetate IR (Nujol): 1650 cm$^{-1}$; NMR (D$_2$O, δ): 1.35–1.65 (1H, m), 1.65–1.90 (2H, m), 1.90–2.15 (1H, m), 2.35–2.60 (1H, m), 2.73 (1H, d, J=2.5 Hz), 2.75–2.95 (2H, m), 2.95–3.50 (2H, m), 3.70–4.00 (2H, m), 4.00–4.40 (5H, m), 4.85–5.15 (1H, m), 6.54 (1H, d, J=15.4 Hz), 6.79 (1H, dd, J=15.4 and 7.4 Hz); MASS (m/z): 334 (M$^+$+1).

EXAMPLE 158

N-[(R)-1-[4-(3-Azetidinyl)-(E)-2-butenoyl]-3-piperidylcarbonyl]-3(S)-ethynyl-β-alanine Trifluoroacetate IR (Neat): 1720 cm$^{-1}$; NMR (D$_2$O, δ): 1.35–2.10 (5H, m), 2.30–2.55 (1H, m), 2.59 (2H, t, J=6.8 Hz), 2.73 (1H, d, J=2.3 Hz), 2.75–3.50 (5H, m), 3.80–4.35 (6H, m), 4.85–5.00 (1H, m), 6.42–6.65 (2H, m); MASS (m/z): 348 (M$^+$+1).

EXAMPLE 159

To a solution of N-[(R)-1-[3-(1-tert-butoxycarbonyl-4-piperidyl)-(E)-acryloyl]-3-piperidylcarbonyl]-3(S)-ethynyl-β-alanine pivaloyloxymethyl ester (0.39 g) in ethyl acetate (4 ml) was added 4N HCl in ethyl acetate (1.61 ml) at 0° C., and the reaction mixture was stirred for 3 hours at room temperature. The precipitates were filtered and washed with diethyl ether, and dissolved with water. The solution was purified by HPLC eluting with 0.1% aqueous trifluoroacetic acid:CH$_3$CN=(67:33) to give N-[(R)-1-[3-(4-piperidyl)-(E)-acryloyl]-3-piperidylcarbonyl]-3(S)-ethynyl-β-alanine pivaloyloxymethyl ester trifluoroacetate (301.4 mg, 81.2%).

IR (KBr pellet): 3373, 3049, 2981, 2943, 2870, 2536, 1757, 1674, 1659, 1601 cm$^{-1}$; NMR (D$_2$O, δ): 1.19 (9H, s), 1.46–1.86 (6H, m), 1.93–2.11 (3H, m), 2.39–2.66 (2H, m), 2.77 (1H, d, J=2.4 Hz), 2.90–2.95 (2H, m), 3.00–3.30 (4H, m), 3.40–3.52 (3H, m), 3.90–4.13 (2H, m), 5.78 (2H, s), 6.45 (1H, d, J=15.7 Hz), 6.64 (1H, dd, J=15.5 and 6.2 Hz); MASS (m/z): 476 (M$^+$ free+1).

The following compounds [Examples 160 to 161] were obtained according to a similar manner to that of Example 159.

EXAMPLE 160

N-[(R)-1-[3-(4-Piperidyl)-(E)-acryloyl]-3-piperidylcarbonyl]-β-alanine Pivaloyloxymetyl Ester Trifluoroacetate IR (KBr pellet): 3325, 2978, 2870, 2750, 1757, 1657, 1603 cm$^{-1}$; NMR (D$_2$O, δ): 1.19 (9H, s), 1.40–2.12 (10H, m), 2.37–2.59 (2H, m), 2.66 (2H, t, J=6.4 Hz), 2.95–3.34 (3H, m), 3.43–3.52 (4H, m), 3.92–4.35 (2H, m), 5.76 (2H, s), 6.46 (1H, d, J=15.5 Hz), 6.64 (1H, dd, J=15.5 and 6.2 Hz); MASS (m/z): 452 (M$^+$ free+1).

EXAMPLE 161

N-[(R)-1-[3-(4-Piperidyl)-(E)-acryloyl]-3-piperidylcarbonyl]-3(S)-trifluoroacetylaminomethyl-β-alanine Trifluoroacetate IR (Nujol): 1720, 1650 cm$^{-1}$; NMR (D$_2$O, δ): 1.35–2.15 (9H, m), 2.30–2.80 (4H, m), 2.80–3.60 (9H, m), 3.75–4.05 (1H, m), 4.05–4.25 (1H, m), 4.35–4.60 (1H, m), 6.43 (1H, d, J=14.9 Hz), 6.55–6.70 (1H, m); MASS (m/z): 463 (M$^+$+1).

EXAMPLE 162

1N aqueous LiOH (3.0 ml) was added to a solution of N-[(R)-1-[3-(1-tert-butoxycarbonyl-4-piperidyl)-(Z)-acryloyl]-3-piperidylcarbonyl]-3(S)-ethynyl-β-alanine ethyl ester (1.0 g) in tetrahydrofuran (5 ml)-EtOH (5 ml) at 0° C. The reaction mixture was stirred for 2 hours at room temperature, then water was added, and the whole was washed with diethyl ether. The aqueous layer was made acidic with 20% aqueous KHSO$_4$, and extracted with ethyl acetate. The organic layer was dried over MgSO$_4$, evaporated in vacuo. The residue was dissolved in ethyl acetate (10 ml) and 4N HCl in ethyl acetate (5.1 ml) was added. The reaction mixture was stirred for 2 hours and diethyl ether was added. The precipitates were collected with filtration and dissolved with water. The solution was neutralized with saturated aqueous NaHCO$_3$ and purified by HP-20 resin eluting with isopropanol/water=(0–30%) to give N-[(R)-1-[3-(4-piperidyl)-(Z)-acryloyl]-3-piperidylcarbonyl]-3(S)-ethynyl-β-alanine (0.5 g, 67.8%).

NMR (D$_2$O, δ): 1.10–1.58 (8H, m), 2.06–2.32 (5H, m), 2.58–2.75 (2H, m), 2.80–2.89 (1H, m), 3.00–3.11 (2H, m), 3.40–3.55 (1H, m), 3.73–3.86 (1H, m), 4.45–4.52 (2H, m), 5.39–5.52 (1H, m), 5.77 (1H, dd, J=2.4 and 11.6 Hz); MASS (m/z): 362 (M$^+$+1).

The following compounds [Examples 163 to 164] were obtained according to a similar manner to that of Example 162.

EXAMPLE 163

N-[(R)-1-[1,2,3,4-Tetrahydroisoquinolin-6-yl)-carbonyl]-3-piperidylcarbonyl]-3(S)-ethynyl-β-alanine IR (Nujol): 1660 cm$^{-1}$; NMR (D$_2$O, δ): 1.40–2.35 (5H, m), 2.35–2.80 (1H, m), 2.45 (1H, dd, J=7.0 and 4.1 Hz), 2.64 (1H, d, J=7.6 Hz), 3.05–3.50 (2H, m), 3.17 (2H, t-like), 3.50–3.85 (2H, m), 3.56 (2H, t, J=6.2 Hz), 7.20–7.50 (3H, m); MASS (m/z): 384 (M$^+$+1).

EXAMPLE 164

N-[(R)-1-[1,2,3,6-Tetrahydro-4-pyridyl)propanoyl]-3-piperidylcarbonyl]-3(S)-ethynyl-β-alanine Hydrochloride NMR (D$_2$O, δ): 1.51–1.96 (5H, m), 2.26–2.50 (5H, m), 2.60–2.68 (6H, m), 2.86–3.07 (1H, m), 3.18–3.44 (3H, m), 3.65 (1H, br), 3.83–3.95 (1H, m), 4.09–4.30 (1H, m), 5.49 (1H, br); MASS (m/z): 362 (M$^+$+1).

EXAMPLE 165

1N aqueous LiOH (0.9 ml) was added to a solution of N-[(R)-1-[3-(1-tert-butoxycarbonyl-1,2,3,6-tetrahydro-4-pyridyl)-(E)-acryloyl]-3-piperidylcarbonyl]-3(S)-ethynyl-β-alanine ethyl ester (0.33 g) in tetrahydrofuran (1.5 ml)-EtOH (1.5 ml) at 0° C. The reaction mixture was stirred for 2 hours at room temperature, then water was added, and the whole was washed with diethyl ether. The aqueous layer was made acidic with 20% aqueous KHSO$_4$, and extracted with ethyl acetate. The organic layer was dried over MgSO$_4$ and evaporated in vacuo. The residue was dissolved in ethyl acetate (5 ml) and 4N HCl in ethyl acetate (2.5 ml) was added. The reaction mixture was stirred for 2 hours and diethyl ether was added. The precipitates were collected with filtration and washed with diethyl ether to give N-[(R)-1-[3-(1,2,3,6-tetrahydro-4-pyridyl)-(E)-acryloyl]-3-piperidylcarbonyl]-3(S)-ethynyl-β-alanine hydrochloride (0.12 g, 44.6%).

NMR (D$_2$O, d): 1.20–1.38 (2H, m), 1.40–1.78 (4H, m), 2.20–2.35 (3H, m), 2.43 (1H, d, J=2 Hz), 2.55–2.60 (3H, m), 2.75–3.14 (4H, m), 3.56–3.75 (2H, m), 3.90–4.02 (1H, m), 5.86 (1H, br), 6.23 (1H, d, J=15 Hz), 6.88 (1H, dd, J=2 and 15 Hz); MASS (m/z): 360 (M$^+$ free+1).

The following compounds [Examples 166 to 169] were obtained according to a similar manner to that of Example 165.

EXAMPLE 166

N-[(R)-1-[3-(4-Piperidyl)-(E)-acryloyl]-3-piperidylcarbonyl]-3(S)-(3-methyl-5-isoxazolyl)-β-alanine Hydrochloride NMR (D$_2$O, δ): 1.55–1.79 (5H, m), 1.92–2.09 (4H, m), 2.26 (3H, s), 2.56–2.60 (2H, m), 2.93–3.29 (5H, m), 3.44–3.50 (2H, m), 3.93–4.27 (2H, m), 5.42–5.48 (1H, m), 6.25 (1H, s), 6.45 (1H, d, J=15.5 Hz), 6.57–6.72 (1H, m); MASS (m/z): 419 (M$^+$).

EXAMPLE 167

N-[(R)-1-[3-(4-Piperidyl)-(E)-acryloyl]-3-piperidylcarbonyl]-2(S)-[4-(trifluoromethyl)benzoylamino]-β-alanine IR (Nujol): 1740, 1680 cm$^{-1}$; NMR (D$_2$O, δ): 1.20–1.85 (5H, m), 1.85–2.15 (3H, m), 2.35–2.65 (2H, m), 2.85–3.35 (6H, m), 3.35–4.00 (3H, m), 4.00–4.40 (1H, m), 4.55–4.70 (2H, m), 6.35 (1H, dd, J=19.0 and 16.0 Hz), 6.50–6.66 (1H, m), 7.85 (2H, d, J=9.0 Hz), 7.93 (2H, d, J=9.0 Hz); MASS (m/z): 525 (M$^+$+1).

EXAMPLE 168

N-[(R)-1-[4-(3-Piperidyl)-(E)-2-butenoyl]-3-piperidylcarbonyl]-3(S)-ethynyl-β-alanine NMR (D$_2$O, δ): 1.10–2.10 (8H, m), 2.28 (1H, t, J=6.8 Hz), 2.35–3.55.(10H, m), 2.67 (1H, d, J=2.3 Hz), 2.65–4.40 (2H, m), 4.70–4.95 (2H, m), 6.40–6.55 (1H, m), 6.58–6.65 (1H, m); MASS (m/z): 476 (M$^+$+1).

EXAMPLE 169

N-[(R)-1-[3-(1,2,3,6-Tetrahydro-4-pyridyl)propanoyl]-3-piperidylcarbonyl]-3(S)-(3-methyl-5-isoxazolyl)-β-alanine Hydrochloride NMR (D$_2$O, δ): 1.28–1.66 (5H, m), 2.06 (3H, s), 2.06–2.09 (4H, m), 2.19–2.39 (3H, m), 2.62–2.84 (5H, m), 3.04–3.10 (3H, m), 3.37 (2H, br), 5.17–5.24 (1H, m), 5.99 (1H, br); MASS (m/z): 419 (M$^+$+1).

EXAMPLE 170

LiOH (40 mg, 1.66 mmol) was added to a solution of N-[(R)-1-[4-(1-tert-butoxycarbonyl-3-azetidinyl)butanoyl]-3-piperidylcarbonyl]-3(S)-ethynyl-β-alanine ethyl ester (663 mg, 1.39 mmol) in tetrahydrofuran (6.0 ml)-EtOH (6.0 ml)-H$_2$O (6.0 ml). The reaction mixture was stirred for 2 hours at room temperature. Solvent was evaporated in vacuo, then water was added, and the whole was washed with diethyl ether. The aqueous layer was made acidic with 5% aqueous KHSO$_4$, and extracted with ethyl acetate. The organic layer was washed with brine, dried over MgSO$_4$ and evaporated in vacuo. Trifluoroacetic acid (2 ml) was added to the residue. The reaction mixture was stirred for 1 hour at room temperature. Solvent was evaporated in vacuo. The residue was purified by HPLC eluting with 0.1% aqueous trifluoroacetic acid:CH$_3$CN=(14:86) to give N-[(R)-1-[4-(3-azetidinyl)butanoyl]-3-piperidylcarbonyl]-3(S)-ethynyl-β-alanine trifluoroacetate (250 mg, 38.8%).

IR (Neat): 1720, 1640 cm$^{-1}$; NMR (D$_2$O, δ): 1.30–2.15 (8H, m), 2.25–2.60 (3H, m), 2.73 (1H, d, J=2.3 Hz), 2.90–3.45 (5H, m), 3.65–3.95 (3H, m), 4.00–4.30 (3H, m); MASS (m/z): 350 (M$^+$+1).

EXAMPLE 171

Trifluoroacetic acid (3 ml) was added to N-[(R)-1-[3-(1-tert-butoxycarbonyl-3-azetidinyl)propanoyl]-3-piperidylcarbonyl]-3(S)-ethynyl-β-alanine (1.11 g, 2.55 mmol). The reaction mixture was stirred for 1 hour at room temperature. Solvent was evaporated in vacuo. The residue was purified by HPLC to give N-[(R)-1-[3-(3-azetidinyl)propanoyl]-3-piperidylcarbonyl]-3(S)-ethynyl-β-alanine trifluoroacetate (270 mg, 23.6%).

IR (Nujol): 1650 cm$^{-1}$; NMR (CDCl$_3$, δ): 1.30–2.15 (7H, m), 2.20–2.60 (3H, m), 2.73 (1H, d, J=2.3 Hz), 2.80–3.50 (6H, m), 3.65–3.95 (3H, m), 3.95–4.35 (4H, m), 4.85–5.00 (1H, m); MASS (m/z): 336 (M$^+$+1).

EXAMPLE 172

Trifluoroacetic acid (3 ml) was added to N-[(R)-1-[3-(1-tert-butoxycarbonyl-4-piperidyl)propanoyl]-3-piperidylcarbonyl]-3(S)-acetylaminomethyl-β-alanine tert-butyl ester. The solvent was evaporated in vacuo. The residue was neutralized with saturated aqueous NaHCO$_3$ and purified by HP-20 resin eluting with isopropanol/water (0–50% to give N-[(R)-1-[3-(4-piperidyl)propanoyl]-3-piperidylcarbonyl]-3(S)-acetylaminomethyl-β-alanine (120 mg, 50.0%).

IR (Nujol): 1640, 1600 cm$^{-1}$; NMR (D$_2$O, δ): 1.20–1.70 (8H, m), 1.70–2.15 (7H, m), 1.98 (3H, s), 2.40–2.65 (3H, m), 2.65–3.10 (2H, m), 3.10–3.50 (6H, m), 3.70–4.05 (1H, m), 4.05–4.25 (2H, m); MASS (m/z): 411 (M$^+$+1).

The following compound was obtained according to a similar manner to that of Example 172.

EXAMPLE 173

N-[(R)-1-[3-(4-Piperidyl)propanoyl]-3-piperidylcarbonyl]-3(S)-benzoylaminomethyl-β-alanine IR (Nujol): 1620 cm$^{-1}$; NMR (D$_2$O, δ): 1.35–2.35 (13H, m), 2.35–2.65 (3H, m), 2.70–3.05 (2H, m), 2.10–3.65 (5H, m), 3.65–4.25 (2H, m), 4.25–4.40 (1H, m), 7.49–7.62 (3H, m), 7.75–7.79 (2H, m); MASS (m/z): 473 (M$^+$+1).

The following compound was obtained according to a similar manner to that of Example 35.

EXAMPLE 174

N-[[2-[3-(1-tert-Butoxycarbonyl- 4-piperidyl)-(E)-acryloyl]-1,2,3,4-tetrahydroisoquinolin-4-yl]carbonyl-3(S)-ethynyl-β-alanine Ethyl Ester MASS (m/z): 538 (M$^+$+1).

The following compound was obtained according to a similar manner to that of Example 170.

EXAMPLE 175

N-[(2-[3-(4-Piperidyl)-(E)-acryloyl]-1,2,3,4-tetrahydroisoquinolin-4-yl]carbonyl]-3(S)-ethynyl-β-alanine Trifluoroacetate IR (Neat): 1740 cm$^{-1}$; NMR (D$_2$O, δ) 1.50–1.80 (2H, m), 2.00–2.20 (2H, m), 2.45–2.90 (4H, m), 3.00–3.25 (2H, t-like), 3.35–3.55 (2H, m), 3.65–3.85 (1H, m), 3.85–4.00 (1H, m), 4.30–4.65 (1H, m), 4.65–5.30 (3H, m), 6.40–6.55 (1H, m), 6.65–6.80 (1H, m), 7.20–7.45 (4H, m); MASS (m/z): 9:40 (M$^+$+1).

The following compound was obtained according to a similar manner to that of Examples 35, 75 and 110.

EXAMPLE 176

N-[(R)-1-[3-(4-Piperidyl)-(E)-acryloyl]-3-piperidylcarbonyl]-3(S)-(2H-1,2,3-triazol-4-yl)-β-alanine Trifluoroacetate NMR (D$_2$O, δ): 1.56–2.07 (9H, m), 2.50–2.64 (2H, m), 3.02–3.50 (7H, s), 3.85–4.27 (2H, m), 5.53–5.57 (1H, m), 6.45 (1H, d, J=15.5 Hz), 6.56–6.63 (1H, m), 7.86 (1H, d, J=5.0 Hz); MASS (m/z): 405 (M$^+$+1).

What is claimed is:

1. A compound of the formula:

wherein
- R$^1$ is tetrahydroisoquinolyl or tetrahydroisoquinolyl having an amino protective group;
- R$^2$ is carboxy or protected carboxy;
- A$^1$ is lower alkylene, lower alkanyl-ylidene, lower alkenylene, cyclo(lower)alkylene or arylene;
- A$^2$ is lower alkylene which is optionally substituted or arylene;

is piperidinediyl or tetrahydroisoquinolinediyl; and
m is an integer of 0 or 1, or a pharmaceutically-acceptable salt thereof.

2. The compound of claim 1, wherein
A$^2$ is lower alkylene which is optionally substituted by 1 to 3 substituents, which are lower alkyl, lower alkynyl, aryl, or ar(lower)alkyl which is optionally substituted by 1 to 3 lower alkoxy, lower alkanoylamino which is optionally substituted by 1 to 3 halogen, aroylamino which is optionally substituted by 1 to 3 halo(lower)alkyl, 5 or 6-membered heteromonocyclic group containing 1 to 2 oxygen atom(s) and 1 to 3 nitrogen atoms, 5 or 6-membered heteromonocyclic group containing 1 to 4 nitrogen atom(s), both of which heteromonocyclic groups are optionally substituted by 1 to 3 lower alkoxy, lower alkoxy(lower)alkyl, cyclo(lower)alkyl, hydroxy(lower)alkyl, ar(lower)alkoxy(lower)alkyl, lower alkanoylamino-(lower)alkyl optionally substituted by halogen, or aroylamino(lower)alkyl; or A$^2$ is arylene.

3. The compound of claim 1, wherein
A$^1$ is lower alkenylene;
A$^2$ is lower alkylene which is optionally substituted by 1 to 3 groups, which are lower alkyl, lower alkynyl, aryl, ar(lower)alkyl which is optionally substituted by 1 to 3 lower alkoxy, lower alkanoylamino which is optionally substituted by 1 to 3 halogen, aroylamino which is optionally substituted by 1 to 3 halo(lower)alkyl, isoxazolyl optionally substituted by lower alkyl, lower alkoxy(lower)alkyl, cyclo(lower)alkyl, hydroxy(lower)alkyl, ar(lower)alkoxy(lower)alkyl, or lower alkanoylamino(lower)alkyl which is optionally substituted by halogen, or A$^2$ is arylene;

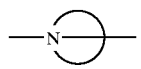

is piperidinediyl or tetrahydroisoquinolinediyl; and
m is an integer of 1.

4. The compound of claim 1, wherein
A$^2$ is lower alkylene which is optionally substituted with one substituent which is lower alkyl, lower alkynyl, aryl, ar(lower)alkyl which is optionally substituted by 1 or 2 lower alkoxy, lower alkanoylamino which is optionally substituted by 3 halogens, aroylamino which is optionally substituted by one tri-halo(lower)alkyl, 5 or 6-membered heteromonocyclic group containing 1 to 2 oxygen atom(s) which is optionally substituted by one lower alkyl, 5 or 6-membered heteromonocyclic group containing 1 to 4 nitrogen atom(s), lower alkoxy (lower)alkyl, cyclo(lower)alkyl, hydroxy(lower)alkyl, ar(lower)alkoxy(lower)alkyl, or lower alkanoylamino (lower)alkyl which is optionally substituted by halogen, or A$^2$ is phenylene; and

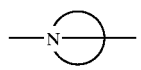

is piperidinediyl or tetrahydroisoquinolinediyl.

5. The compound of claim 1, wherein
A$^2$ is lower alkylene which is optionally substituted by one substituent which is lower alkyl, lower alkynyl, phenyl, phenyl(lower)alkyl which is optionally substituted by 1 or 2 lower alkoxy, lower alkanoylamino, benzoylamino which is optionally substituted by tri-halo(lower)alkyl, isoxazolyl which is optionally substituted by lower alkyl, triazolyl or phenyl(lower) alkoxy(lower) alkyl; and

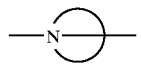

is piperidinediyl.

6. The compound of claim 1, wherein
R$^2$ is pentyloxycarbonyl, isopentyloxycarbonyl, isohexyloxycarbonyl, phenethyloxycarbonyl, phenyloxycarbonyl or indanyloxycarbonyl;
A$^1$ is lower alkylene;
A$^2$ is lower alkylene which has one substituent which is lower alkynyl or lower alkanoylamino;

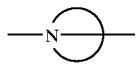

is piperidinediyl; and
m is an integer of 1.

7. The compound of claim 1, wherein
A¹ is lower alkylene;
A² is lower alkylene which is optionally substituted by a 5 or 6-membered heteromonocyclic group containing 1 to 2 oxygen atom(s) and 1 to 3 nitrogen atom(s) substituted by lower alkyl, phenyl(lower)alkoxy(lower)alkyl, hydroxy(lower)alkyl, lower alkoxy(lower)alkyl, cyclo(lower)alkyl, benzoylamino(lower)alkyl, lower alkanoylamino(lower)alkyl, or tri-halo(lower)alkanoylamino, benzoylamino substituted by tri-halo(lower)alkyl, tri-halo(lower)-alkanoylamino(lower)alkyl; or A² is phenylene;

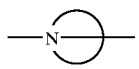

is piperidinediyl; and
m is an integer of 1.

8. The compound of claim 1, wherein
R² is carboxy;
A¹ is lower alkylene; and
A² is lower alkylene which is optionally substituted by one substituent which is isoxazolyl optionally substituted by lower alkyl, tri-halo(lower)alkylbenzoylamino, benzoylamino(lower)alkyl, or tri-halo(lower)alkanoylamino(lower)alkyl.

9. The compound of claim 1, wherein
A¹ is lower alkylene;
A² is lower alkylene which is optionally substituted by one substituent which is lower alkynyl, or 5 or 6-membered heteromonocyclic group containing 1 to 2 oxygen atom(s) and 1 to 3 nitrogen atom(s) which is substituted by lower alkyl,

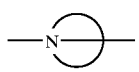

is piperidinediyl; and
m is an integer of 1.

10. The compound of claim 1, wherein
R² is carboxy;
A¹ is lower alkylene; and
A² is lower alkylene which is optionally substituted by one substituent which is lower alkynyl or isoxazolyl optionally substituted by lower alkyl.

11. A process for preparing the compound of claim 1, or the pharmaceutically-acceptable salt thereof, which comprises the step of:

(i) reacting a compound of the formula:

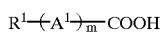

wherein R¹, A¹, and m are each as defined in claim 1, or a reactive compound thereof at the carboxy group, or a salt thereof, with a compound of the formula:

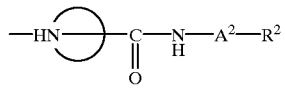

wherein R², A² and

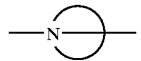

are each as defined in claim 1,
or a reactive compound thereof at the amino group,
or a salt thereof, or (ii) reacting a compound of the formula:

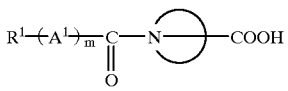

wherein R¹, A¹,

and m are each as defined in claim 1,
or a reactive compound thereof at the carboxy group,
or a salt thereof, with a compound of the formula:

wherein R² and A² are each as defined in claim 1,
or a reactive compound thereof at the amino group,
or a salt thereof, or (iii) reacting a compound of the formula:

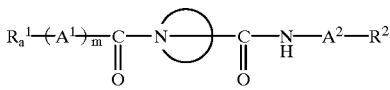

wherein R², A¹, A²,

m are each as defined in claim 1, and
$R_a^1$ is tetrahydroisoquinolyl having an amino protective group,
or a salt thereof, to an elimination reaction of the amino protective group, to give a compound of the formula:

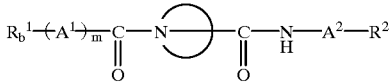

wherein $R^2$, $A^1$, $A^2$,

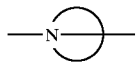

and m are each as defined in claim 1, and $R_b^1$ is tetrahydroisoquinolyl,
or a salt thereof, or
(iv) subjecting a compound of the formula:

wherein $R^1$, $A^1$, $A^2$,

and m are each as defined in claim 1, and $R_a^2$ is protected carboxy,
or a salt thereof, to an elimination reaction of the carboxy protective group, to give a compound of the formula:

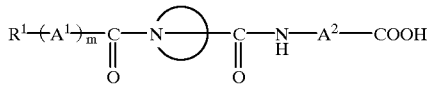

wherein $R^1$, $A^1$, $A^2$,

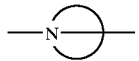

and m are each as defined above,
or a salt thereof, or
(v) subjecting a compound of the formula:

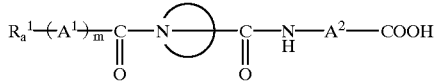

wherein $R_a^1$ is as defined above, and $A^1$, $A^2$,

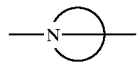

and m are each as defined in claim 1,
or a reactive compound thereof at the carboxy group or a salt thereof, to a protecting reaction of the carboxy, to give a compound of the formula:

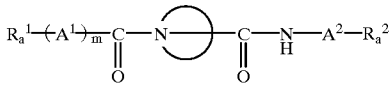

wherein $R_a^1$ and $R_a^2$ are each as defined above, and $A^1$, $A^2$,

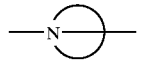

and m are each as defined in claim 1,
or a salt thereof, and further optionally forming the pharmaceutically-acceptable salt of said compound of claim 1.

12. A pharmaceutical composition which comprises, as an active ingredient, an effective amount of one or more compounds of claim 1, or a pharmaceutically acceptable salt thereof, in admixture with a pharmaceutically acceptable carrier.

13. A method for the treatment of diseases caused by thrombus formation, restenosis of reocculusion, the thrombus formation in case of vascular surgery, valve replacement, extracorporeal circulation or transplantation, disseminated intravascular coagulation, thrombotic thrombocytopenic, essential thrombocytosis, inflammation, immune diseases, or metastasis, or for the adjuvant therapy with thrombolytic drug or anticoagulant, which comprises administering an effective amount of one or more compounds of claim 1, or a pharmaceutically acceptable salt thereof, to a mammal in need thereof.

14. The method of claim 13, wherein the mammal is a human.

* * * * *